United States Patent [19]

Levitt

[11] Patent Number: 4,892,946

[45] Date of Patent: Jan. 9, 1990

[54] AGRICULTURAL SULFONAMIDES

[75] Inventor: George Levitt, Wilmington, Del.

[73] Assignee: E. I. Du Pont De Nemours and Company, Wilmington, Del.

[21] Appl. No.: 209,307

[22] Filed: Nov. 24, 1980

Related U.S. Application Data

[63] Continuation-in-part of Ser. No. 171,355, Jul. 23, 1980, Pat. No. 4,305,884, and a continuation-in-part of Ser. No. 98,781, Nov. 30, 1979, Pat. No. 4,394,506.

[51] Int. Cl.$^4$ .................. C07D 239/28; C07D 239; C07D 30
[52] U.S. Cl. ........................................ 544/321; 71/88; 71/90; 71/92; 71/93; 544/112; 544/113; 544/114; 544/185; 544/211; 544/326; 544/327; 544/328; 544/322; 544/329; 544/331; 544/332
[58] Field of Search ................................ 544/322, 321

[56] References Cited

U.S. PATENT DOCUMENTS 3,639,474  2/1972  Harrington et al. ............ 424/321 X

FOREIGN PATENT DOCUMENTS 853374  10/1977  Belgium .
0001515  10/1978  European Pat. Off. .
1468747  10/1967  France .

OTHER PUBLICATIONS

Logemann et al., Chem. Abst., vol. 53 (1959), 18052g.
Wojciechowski, J., Acta. Polon. Pharm., vol. 19 (1962), pp. 121–125.

Primary Examiner—Catherine L. Mills

[57] ABSTRACT

N-(heterocyclicaminocarbonyl)arylsulfonamides in which the aryl radical is substituted in the 2-position by a carboxy radical, ester, thioester, or amide thereof; e.g. N-[(4,6-dimethylpyrimidin-2-yl)aminocarbonyl]-2-methoxycarbonylbenzenesulfonamide or N-[(4,6-dimethoxy-1,3,5-triazin-2-yl)aminocarbonyl]-2-methoxycarbonylbenzenesulfonamide; are useful for the regulation of plant growth and as pre-emergence and post-emergence herbicides.

50 Claims, No Drawings

AGRICULTURAL SULFONAMIDES

CROSS-REFERENCE TO RELATED APPLICATION

This application is continuation-in-part of Ser. No. 171,355, filed Jul. 23, 1980, now U.S. Pat. No. 4,305,884 which is a continuation-in-part of my copending application Ser. No. 098,781, filed Nov. 30, 1979, now U.S. Pat. No. 4,394,506.

BACKGROUND OF THE INVENTION

This invention relates to novel N-(heterocyclicaminocarbonyl)arylsulfonamides in which the aryl radical is substituted by a carboxyl radical, ester, thioester or amide thereof. The compounds of this invention and their agriculturally suitable salts, are useful as agricultural chemicals, e.g. plant growth regulants and herbicides.

Netherlands Pat. No. 121,788, published September 15, 1966, discloses the preparation of compounds of the following Formula and their use as general or selective herbicides:

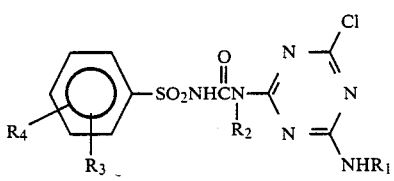

wherein $R_1$ and $R_2$ may independently be alkyl of 1–4 carbon atoms; and $R_3$ and $R_4$ may independently be hydrogen, chlorine or alkyl of 1–4 carbon atoms.

U.S. Pat. No. 3,637,366 discloses compounds having the formula:

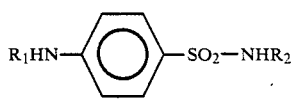

wherein $R_1$ is hydrogen or lower saturated aliphatic acyl and $R_2$ is hydrogen, 2-pyrimidinyl, pyridyl, amidino, acetyl or carbamoyl.

The disclosed compounds are said to provide control of crabgrass, cress, endive, clover and Poa annua.

French Pat. No. 1,468,747 discloses the following para-substituted phenylsulfonamides as being useful as antidiabetic agents:

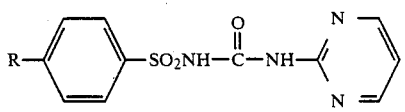

wherein R=H, halogen, $CF_3$ or alkyl.

Logemann et al. Chem Ab., 53, 18052 g (1959), disclose a number of sulfonamides, including uracil derivatives and those having the formula:

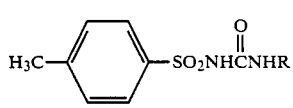

wherein

R is butyl, phenyl, or

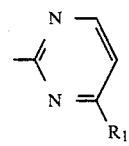

and $R_1$ is hydrogen or methyl.

When tested for hypoglycemic effect in rats (oral doses of 25 mg/100 g), the compounds in which R is butyl and phenyl were most potent. The others were of low potency or inactive.

Wojciechowski, J. Acta. Polon. Pharm 19, p. 121–5 (1962) [Chem. Ab., 59 1633 e] describes the synthesis of N-[(2,6-dimethoxypyrimidin-4-yl)aminocarbonyl]-4-methylbenzenesulfonamide:

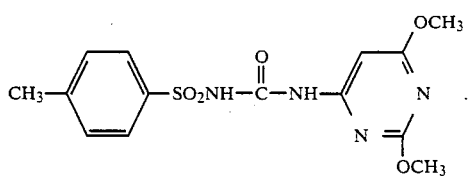

Based upon similarity to a known compound, the author speculated that the foregoing compound might have a hypoglycemic activity.

Substituted-pyrimidinyl sulfonylureas of the following formula, which are also para-substituted on the phenyl ring, are disclosed in Farmco Ed. Sci., 12, 586 (1957) [Chem. Ab., 53, 18052 g (1959)]:

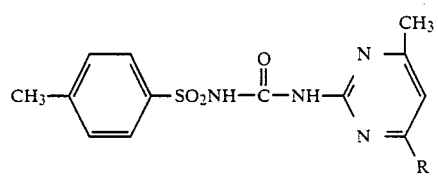

wherein R=H or $CH_3$.

The presence of undesired vegetation causes substantial damage to useful crops, especially agricultural products that satisfy man's basic food and fiber needs, such as cotton, rice, corn, wheat, and the like. The current population explosion and concomitant world food and fiber shortage demand improvements in the efficiency of producing these crops. Preventing or minimizing loss of a portion of such valuable crops by killing, or inhibiting the growth of undesired vegetation is one way of improving this efficiency. A wide variety of materials useful for killing or inhibiting (controlling) the growth of undesired vegetation is available; such materials are commonly referred to as herbicides. The need still exists however, for more effective herbicides.

SUMMARY OF THE INVENTION

According to this invention, there are provided novel compounds of Formula I and their agriculturally suitable salts, e.g. Na, K, alkyl ammonium, trichloroacetic acid, suitable agricultural compositions containing them and methods of using them as herbicides and as plant growth regulants.

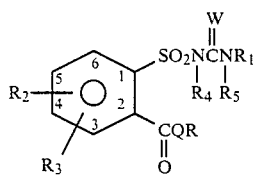

wherein
Q is O, S or

when Q is O or S then R is $C_1$–$C_{12}$ alkyl, $C_3$–$C_{10}$ alkenyl; $C_3$–$C_{10}$ alkynyl; $C_2$–$C_6$ alkyl substituted with one to four substituents selected from 0–3 atoms of F, Cl, Br, 0–2 methoxy groups and 0–1 cyano groups; —$CH_2CN$;

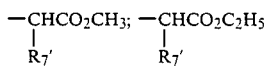

where $R_7'$ is H or $CH_3$; $C_3$–$C_6$ alkenyl substituted with 1–3 atoms of F, Cl, Br; $C_3$–$C_6$ alkynyl substituted with one of F, Cl or Br; $C_5$–$C_8$ cycloalkyl; $C_5$–$C_8$ cycloalkenyl; $C_5$–$C_6$ cycloalkyl substituted with $OCH_3$, alkyl of $C_2$–$C_4$, F, Cl or Br or one to four methyl groups; $C_4$–$C_{10}$ cycloalkylalkyl; $C_4$–$C_8$ cycloalkylalkyl with 1–2 $CH_3$; $C_7$–$C_{10}$ bicycloalkyl; $C_7$–$C_{10}$ bicycloalkenyl; $C_{10}$ tricycloalkyl, $C_{10}$ tricycloalkenyl;

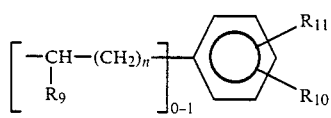

where $R_9$ is $C_1$–$C_3$ alkyl or hydrogen, $R_{10}$ and $R_{11}$ are independently hydrogen, $C_1$–$C_3$ alkyl, Cl, Br, —$OCH_3$, —$OC_2H_5$ or $R_{10}$ and $R_{11}$ may be taken together to form a 5 or 6 member ring:

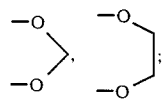

and n is 0, 1, 2 or 3 provided the total number of carbon atoms is ≦12;

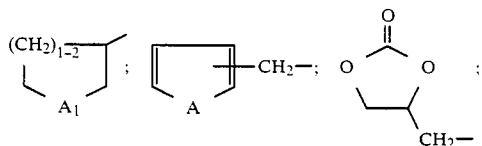

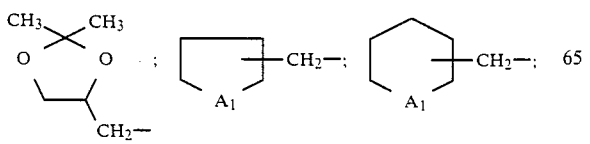

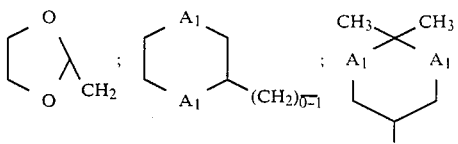

A is O, S;
$A_1$ is O, S, $SO_2$;
when Q is O, then R is H, M, —$CH_2CH_2OR_7$;

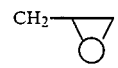

—$CH_2CH_2CH_2OR_7$,

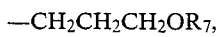

where $R_7$ is —$CH_2CH_3$, —$CH(CH_3)_2$, phenyl, —$CH_2CH_2Cl$, —$CH_2CCl_3$; $CH_2OR_8'$ where $R_8'$ is —$CH_3$, —$CH_3CH_2$, —$CH(CH_3)_2$, —$CH_2CH_2Cl$, —$CH_2CCl_3$, phenyl,

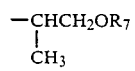

—$CH_2CH_2OCH_3$, —$CH_2CH_2OCH_2CH_3$; —(-$CH_2CH_2O$)$_{n'}R_8$,

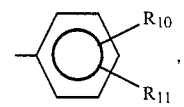

where $R_8$ is —$CH_3$, —$CH_2CH_3$, —$CH(CH_3)_2$, phenyl, —$CH_2CH_2Cl$, —$CH_2CCl_3$ and n' is 2 or 3;

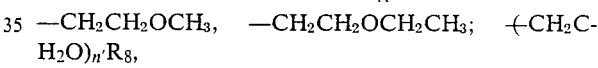

where $R_{12}$ is —$CH_3$, —$CH_2CH_3$, —$CH(CH_3)_2$, or phenyl; and
provided R has a total number of carbon atoms ≦13; when Q is

then R is hydrogen; $C_1$–$C_{12}$ alkyl; —(-$CH_2CH_2O$-)$_{n'''}R_{12}$, —$CH_2CH_2CH_2OR_{12}$ where $R_{12}$ is as defined above and n''' is 1–3; $C_3$–$C_{10}$ alkenyl; $C_3$–$C_6$ alkynyl; $C_3$–$C_8$ cycloalkyl; $C_5$–$C_6$ cycloalkenyl; $C_5$–$C_8$ cycloalkyl substituted with 1 to 3 substituents selected from 0–2 —$OCH_3$, 0–3 —$CH_3$ or —$C_2H_5$; trifluoromethylcyclohexyl; $C_4$–$C_{10}$ cycloalkylalkyl; $C_4$–$C_8$ cycloalkylalkyl substituted with 1–2 —$CH_3$; —$CH_2CN$; —$CH_2CH_2CN$;

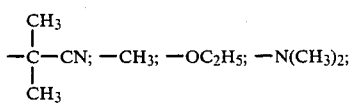

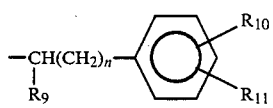

where n, R$_9$, R$_{10}$ and R$_{11}$ are as defined above;

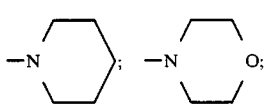

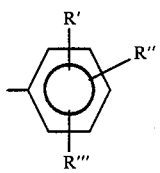

where R' is hydrogen, C$_1$-C$_4$ alkyl, —OCH$_3$, F, Br, Cl, —CF$_3$, CN, NO$_2$, —SO$_2$CH$_3$, —SCH$_3$, —N(CH$_3$)$_2$; R" is hydrogen, C$_1$-C$_4$ alkyl, —OCH$_3$, F, Br, Cl; R''' is hydrogen, —CH$_3$, Cl, F or Br;
R$_6$ is hydrogen, C$_1$-C$_6$ alkyl, allyl, —CH$_2$CN; or —CH$_2$CH$_2$CN; or R$_6$ and R can be taken together to form —(CH$_2$)$_4$—, —(CH$_2$)$_5$—, —(CH$_2$)$_6$—, —CH$_2$CH$_2$OCH$_2$CH$_2$—;

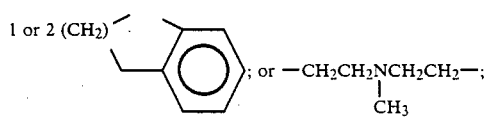

with the proviso that when R is —OCH$_3$ or —OC$_2$H$_5$ then R$_6$ is H or —CH$_3$; when R$_6$ is —CH$_2$CH$_2$CN or —CH$_2$CN then R is —CH$_2$CH$_2$CN or CH$_2$CN; and R and R$_6$ have a total number of carbon atoms $\leq 13$; and further provided that when QR is other than

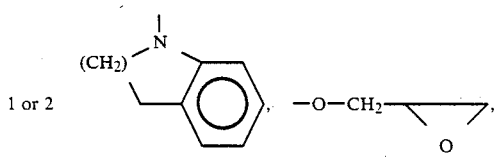

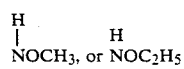

then R$_2$ must be NCO,

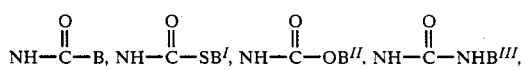

CF$_3$SO$_2$NH or CH$_3$SO$_2$NH;

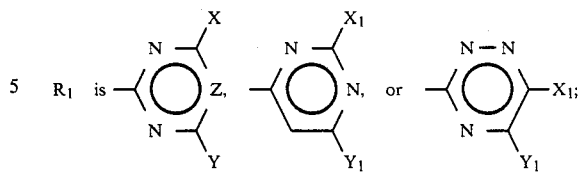

R$_2$ is H, Cl, Br, F, C$_1$-C$_3$ alkyl, —NO$_2$, —SO$_2$CH$_3$, —OCH$_3$, —SCH$_3$, —CF$_3$, —N(CH$_3$)$_2$, —NH$_2$, —CN, —NCO,

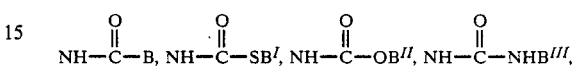

CF$_3$SO$_2$NH or CH$_3$SO$_2$NH;
B is C$_1$-C$_4$ alkyl optionally substituted with 1-3 atoms of F, Cl, Br or a single OCH$_3$ group; C$_2$-C$_4$ alkenyl;
B$^I$ is C$_1$-C$_4$ alkyl or C$_3$-C$_4$ alkenyl;
B$^{II}$ is C$_1$-C$_4$ alkyl optionally substituted with CH$_3$OCH$_2$CH$_2$, CH$_3$CH$_2$OCH$_2$CH$_2$ or 1-3 atoms of F, Cl or Br; C$_3$-C$_4$ alkenyl;
B$^{III}$ is C$_1$-C$_4$ alkyl optionally substituted with Cl or OCH$_3$; C$_3$-C$_4$ alkenyl;
R$_3$ is H, Cl, Br, F or CH$_3$;
R$_4$ is H, or —CH$_3$;
R$_5$ is H, —CH$_3$, or —OCH$_3$;
M is an alkali metal;
W is oxygen or sulfur;
X is H, Cl, —CH$_3$, —OCH$_3$, —OCH$_2$CH$_3$, —OCH$_2$CH$_2$OCH$_3$, CH$_2$OCH$_3$ or CH$_2$OCH$_2$CH$_3$;
Y is H; F; Cl; Br; C$_1$-C$_4$ alkyl;

C$_1$-C$_4$ alkyl substituted with —OCH$_3$, —OC$_2$H$_5$, —CN,

or 1 to 3 atoms of F, Cl, Br; C$_3$-C$_4$ alkenyl; —CH$_2$C≡CR$_{13}$ where R$_{13}$ is H, —CH$_3$, —CH$_2$Cl; —A—(CH$_2$)$_{n'}$A$_1$ —(C$_1$-C$_3$ alkyl), and n', A and A$_1$ are as previously defined;

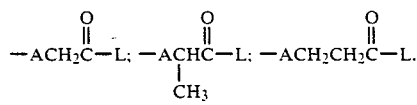

where L is —NH$_2$, OH,

—NH(C$_1$-C$_4$ alkyl), —N(C$_1$-C$_4$ alkyl)$_2$, C$_1$-C$_6$ alkoxy; —SCN; —N$_3$; NR$_{16}$R$_{17}$ where R$_{16}$ is H or CH$_3$ and R$_{17}$ is H, —OCH$_3$, C$_1$-C$_6$ alkyl, C$_1$-C$_4$ alkyl substituted with —CN,

$C_3$-$C_4$ alkenyl; $C_3$-$C_6$ cycloalkyl; or $C_2$-$C_3$ alkyl substituted with —$OCH_3$, $OC_2H_5$; or $R_{16}$ and $R_{17}$ can be taken together to form —$CH_2CH_2CH_2CH_2$—, —$CH_2CH_2OCH_2CH_2$—; —O—$R_{14}$ where $R_{14}$ is $C_1$-$C_4$ alkyl; $C_2$-$C_4$ alkyl substituted with 1-3 atoms of F, Cl or Br; $C_1$-$C_4$ alkyl substituted with cyano; $C_3$-$C_4$ alkenyl, —$CH_2C\equiv CR_{13}$; where $R_{13}$ is as previously defined;

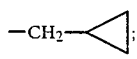

—$SR_{15}$ where $R_{15}$ is $C_1$-$C_4$ alkyl, $C_1$-$C_2$ alkyl substituted with CN, allyl, propargyl; with the provision that when Y is $\leq 4$ carbon atoms, R is $\leq 4$ carbon atoms, when X is Cl, then Y is Cl, and when X and Y are both H, then R is $\leq 4$ carbon atoms. Z is N or CH; $Y_1$ is H, —$OCH_3$, —$CH_3$ or $OCH_2CH_3$; $X_1$ is H, Cl, —$OCH_3$, —$OCH_2CH_3$, —$CH_3$; providing that $X_1$ and $Y_1$ are not both simultaneously hydrogen and when $R_1$ is

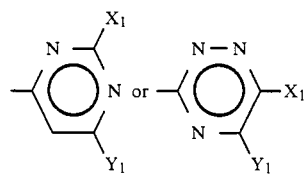

then $R_4$ and $R_5$ are both H and R is $\leq 5$ carbon atoms.

Preferred for higher activity and/or lower cost and/or greater ease at synthesis are:

1. Compounds of the generic scope in which W is O; $R_3$, $R_4$ and $R_5$ are H; $R_2$ is —NCO,

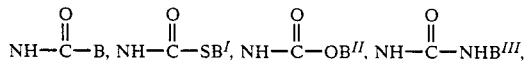

$CF_3SO_2NH$ or $CH_3SO_2NH$; and Q is O;

2. Compounds of the generic scope in which W is O; $R_3$, $R_4$ and $R_5$ are H; and QR is

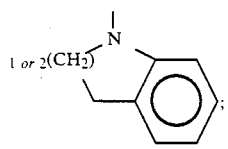

3. Compounds of the generic scope in which W is O; $R_3$, $R_4$ and $R_5$ are H; and QR is

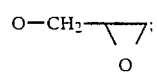

4. Compounds of the generic scope in which W is O; $R_3$ $R_4$ and $R_5$ are H; and QR is

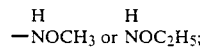

More preferred for reasons of even higher activity and/or even lower cost and/or even greater ease of synthesis are:

5. Compounds of preferred 1 in which $R_2$ is in the 5-position of the benzene ring;
6. Compounds of preferred 1 in which $R_1$ is

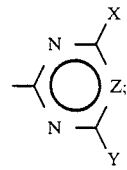

7. Compounds of preferred 6 in which $R_2$ is in the 5-position at the benzene ring;
8. Compounds of preferred 7 where R is $C_1$-$C_4$ alkyl, $C_3$-$C_4$ alkenyl; $C_2$-$C_3$ alkyl substituted with Cl; $CH_2CH_2$—O$+CH_3$, $CH_2CH_3$);

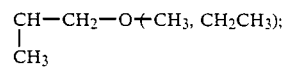

or $CH_2CH_2CH_2$—O$+CH_3$, $CH_2CH_3$);

9. Compounds of preferred 8 in which X is $CH_3$, $OCH_3$, or $CH_2OCH_3$;
10. Compounds of preferred 9 in which Y is $CH_3$, $CH_3CH_2$, $C_1$-$C_4$ alkoxy or $CH_3S$;
11. Compounds of preferred 10 in which Y is $CH_3$, $CH_3O$, or $SCH_3$;
12. Compounds of preferred 11 in which R is $CH_3$;
13. Compounds of preferred 11 in which B, $B^I$, $B^{II}$ are $C_1$-$C_4$ alkyl and $B^{III}$ is $C_1$-$C_4$ alkyl optionally substituted with an atom of F, Cl or Br;
14. Compounds of preferred 13 in which X and Y are independently $CH_3$ or $CH_3O$;
15. Compounds of preferred 14 in which R is $CH_3$;
16. Compounds of preferred 15 in which $R_2$ is

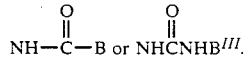

Also more preferred for reasons of even higher activity and/or even lower cost and/or even greater ease of synthesis are:

17. Compounds of preferred 2 in which $R_2$ is H, F, Cl, Br, $CH_3$, $CH_3O$ or $CF_3$;
18. Compounds of preferred 17 in which $R_1$ is

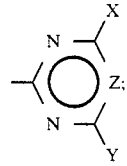

19. Compounds of preferred 18 in which X is $CH_3$, $CH_3O$, or $CH_2OCH_3$; and Y is $CH_3$, $CH_3O$ or $CH_3S$;
20. Compounds of preferred 19 in which $R_2$ is H; X and Y are independently $CH_3$ or $CH_3O$.

21. Compounds of preferred 20 in which QR is

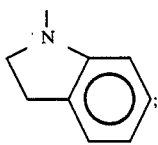

Also more preferred and in increasing order for reasons of even higher activity and/or even lower cost and/or even greater ease of synthesis are:

22. Compounds of preferred 3 in which $R_2$ is H, F, Cl, Br, $CH_3$, $CH_3O$ or $CF_3$;
23. Compounds of preferred 22 in which $R_1$ is

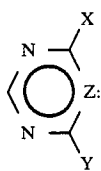

24. Compounds of preferred 23 in which X and Y are independently $CH_3$ or $CH_3O$;
25. Compounds of preferred 24 in which $R_2$ is H;

Specifically preferred for reasons of highest activity and/or lowest cost and/or greatest ease of synthesis are:

Methyl 2-[[(4,6-dimethylpyrimidin-2-yl)aminocarbonyl]aminosulfonyl]-5-[(methylamino)carbonylamino]benzoate;

Methyl 2-[[(4-methoxy-6-methylpyrimidin-2-yl)aminocarbonyl]aminosulfonyl]-5-[(methylamino)carbonylamino]benzoate;

Methyl 2-[[(4-methoxy-6-methyl-1,3,5-triazin-2-yl)aminocarbonyl]aminosulfonyl]-5-[(methylamino)carbonylamino]benzoate;

Methyl 5-[(1,1-dimethylethylamino)carbonylamino]-2-[[(4-methoxy-6-methylpyrimidin-2-yl)aminocarbonyl]aminosulfonyl]benzoate;

Methyl 5-[(1,1-dimethylethylamino)carbonylamino]-2-[[(4-methoxy-6-methyl-1,3,5-triazin-2-yl)aminocarbonyl]aminosulfonyl]benzoate;

Methyl 5-[(1,1-dimethylethylamino)carbonylamino]-2-[[(4-methoxy-6-methyl-1,3,5-triazin-2-yl)aminocarbonyl]aminosulfonyl]benzoate;

Methyl 5-[(1-methylethylamino)carbonylamino]-2-[[(4-methoxy-6-methyl-1,3,5-triazin-2-yl)aminosulfonyl]benzoate;

Methyl 2-[[(4,6-dimethoxypyrimidin-2-yl)aminocarbonyl]aminosulfonyl]-4-[(methylamino)carbonylamino]benzoate;

Methyl 4-(acetylamino)-2-[[(4,6-dimethoxypyrimidin-2-yl)aminocarbonyl]aminosulfonyl]benzoate;

Methyl 4-[(2-chloroethylamino)carbonylamino]-2-[[(4,6-dimethoxypyrimidin-2-yl)aminosulfonyl]benzoate;

1-[2-[[(4,6-dimethoxypyrimidin-2-yl)aminocarbonyl]aminosulfonyl]benzooyl]-2,3-dihydro-1H-indole;

1-[2-[[(4,6-dimethylpyrimidin-2-yl)aminocarbonyl]aminosulfonyl]benzoyl]-2,3-dihydro-1H-indole;

1-[2-[[(4-methoxy-6-methylpyrimidin-2-yl)aminocarbonyl]aminosulfonyl]benzoyl]-2,3-dihydro-1H-indole;

1-[2-[[(4,6-dimethoxy-1,3,5-triazin-2-yl)aminocarbonyl]aminosulfonyl]benzoyl]-2,3-dihydro-1H-indole;

1-[2-[[(4,6-dimethyl-1,3,5-triazin-2-yl)aminocarbonyl]aminosulfonyl]benzoyl]-2,3-dihydro-1H-indole;

1-[2-[[(4-methoxy-6-methyl-1,3,5-triazin-2-yl)aminocarbonyl]aminosulfonyl]benzoyl]-2,3-dihydro-1H-indole;

2-oxiranylmethyl 2-[[(4,6-dimethylpyrimidin-2-yl)aminocarbonyl]aminosulfonyl]benzoate;

2-oxiranylmethyl 2-[[(4,6-dimethoxypyrimidin-2-yl)aminocarbonyl]aminosulfonyl]benzoate;

2-oxiranylmethyl 2-[[(4,6-dimethoxypyrimidin-2-yl)aminocarbonyl]aminosulfonyl]benzoate;

2-oxiranylmethyl 2-[[(4-methoxy-6-methylpyrimidin-2-yl)aminocarbonyl]aminosulfonyl]benzoate;

2-oxiranylmethyl 2-[[(4,6-dimethoxy-1,3,5-triazin-2-yl)aminocarbonyl]aminosulfonyl]benzoate;

2-oxiranylmethyl 2-[[(4,6-dimethyl-1,3,5-triazin-2-yl)aminocarbonyl]aminosulfonyl]benzoate;

2-oxiranylmethyl 2-[[(4-methoxy-6-methyl-1,3,5-triazin-2-yl)aminocarbonyl]aminosulfonyl]benzoate; and Methyl 2-[[(4-methoxymethyl-6-methylthio-1,3,5-triazin-2yl)aminocarbonyl]aminosulfonyl]benzoate.

SYNTHESIS

Many of the compounds of Formula I where QR is

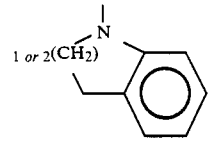

can be prepared from the corresponding esters by reaction with the dialkylaluminum-N-alkyl-amide derivatives according to Equation 1.

Equation 1

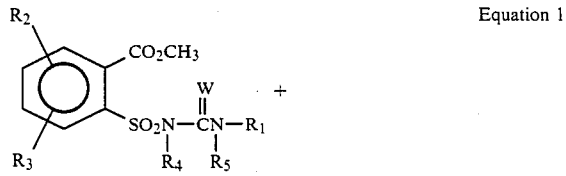

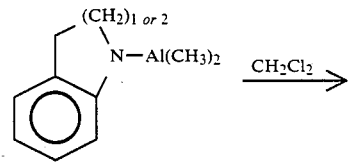

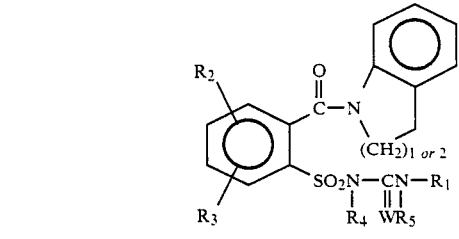

The intermediate alkylaminoaluminum compounds prepared according to A. Basha, M. Lipton and S. W. Weinreb, *Tetrahedron Letters*, 4171 (1977), are comingled with a suspension of the esters in methylene chloride and the mixture is refluxed for 12 to 24 hours. The product can be isolated by addition of aqueous hydrochloric acid to decompose the residual reaction mass and the product is dissolved in the methylene chloride. Evaporation of the methylene chloride yields the desired product which may be purified by crystallization or column chromatography.

The preparation of esters of Formula II is described in European patent application No. 7687.

Compounds of Formula IV, which are useful intermediates in Equation 3, are prepared as shown in Equation 2.

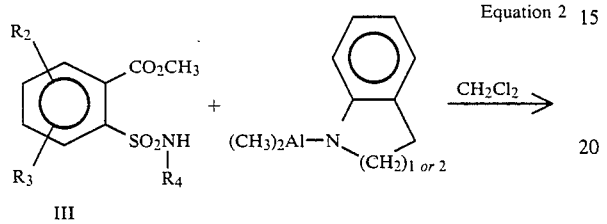

Equation 2

III

IV

The conditions described for Equation 1 are suitable for the conversion of the esters of Formula III to the amides IV as shown in Equation 2.

The amides of Formula IV are especially useful for the preparation of compounds of Formula I wherein Y has an ester substituent $CO_2(C_1-C_6)$, by the route described in Equation 3.

Equation 3

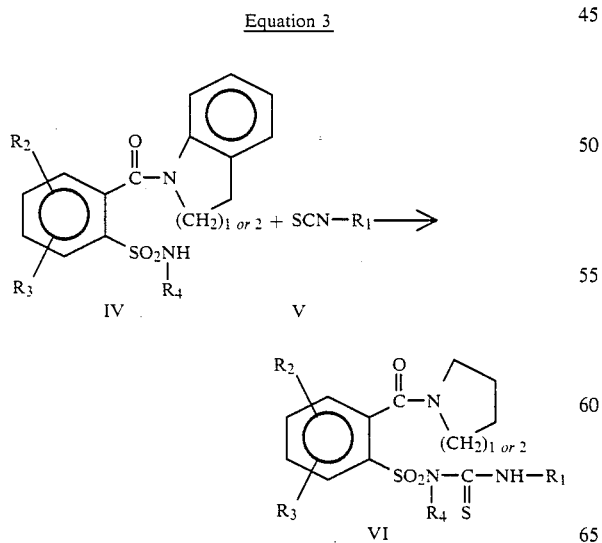

IV V

VI

The procedure of Equation 3 and the preparation of the heterocyclic isothiocyanates which are used in Equation 3 are described in European Patent Application No. 7687.

As shown in Equation 4, compounds of Formula I can be prepared by the reaction of an appropriately substituted sulfonyl N-methylcarbonyl chloride or sulfonyl N-methylthiocarbonyl chloride of Formula VII with an appropriate aminopyrimidine or aminotriazine of Formula VIII.

Equation 4

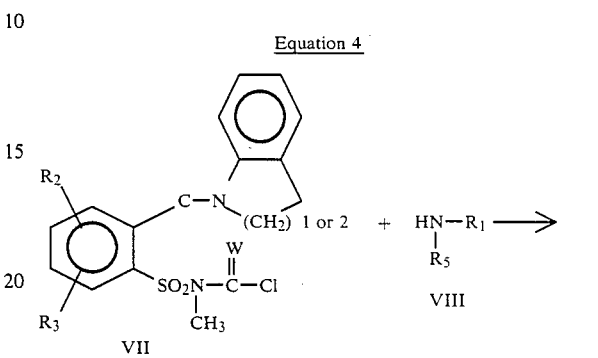

VII VIII

IX

The procedure of Equation 4 and the preparation of the chlorides of Formula VII are described in European Patent Application No. 7687.

Compounds wherein R is

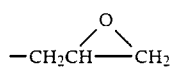

can be prepared by the reaction of salts of the parent acid (R=H) with the corresponding halogen compounds as shown in Equation 5.

Equation 5

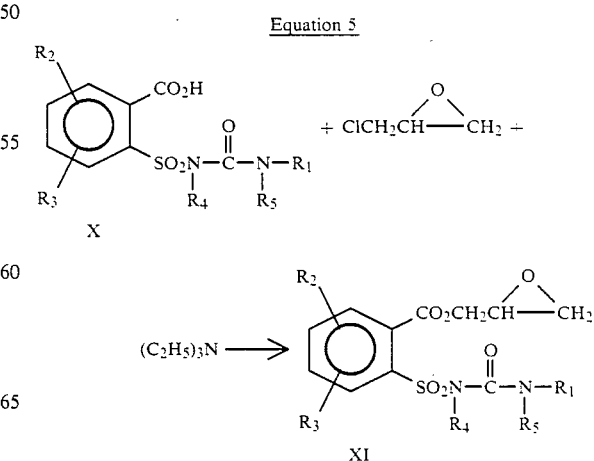

X

XI

The procedure of Equation 5 and the preparation of compounds of Formula X are described in European Patent Application No. 7687.

Compounds of Formula I wherein $R_2$ is isocyanate can be prepared by combining an appropriate 2-aminopyrimidine or 2-aminotriazine with an appropriately substituted isocyanatobenzenesulfonyl isocyanate.

Equation 6

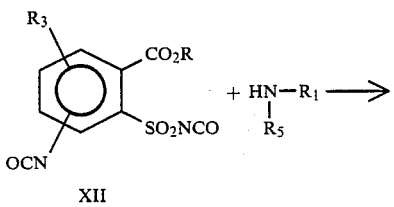

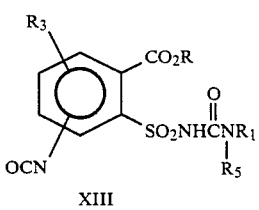

The compounds of Formula XII can be prepared from the corresponding o-carbonyl substituted aminobenzenesulfonamide by the action of phosgene as shown in Equation 7.

Equation 7

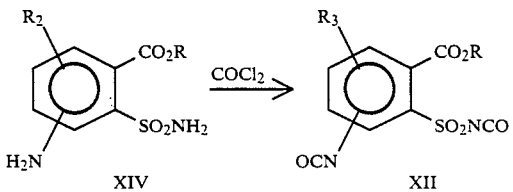

The procedures of Equations 6 and 7 are described in European Patent Application No. 1515.

The isocyanate substituent in compound XIII can be converted readily to the carbamates (XIIIa), thiolcarbamates (XIIIb), or urea derivatives (XIIIc) of this invention by reaction thereof respectively with the appropriate alcohol (Equation 8), thiol (Equation 9) or amine (Equation 10).

Equation 8

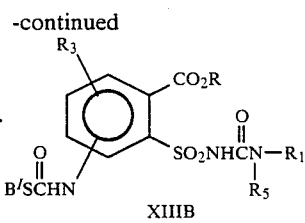

Equation 9

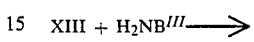

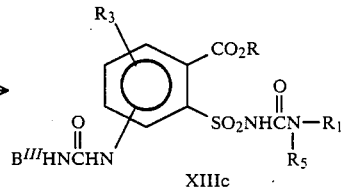

Equation 10

$$XIII + H_2NB^{III} \longrightarrow$$

The reactions of Equations 8, 9 and 10 can be carried out in situ with isocyanate compound (XIII), or isocyanate compound (XIII) can first be isolated and added to the alcohol, thiol or amine neat or in a non-reactive solvent. In any event, the reactions of Equations 8, 9 and 10 proceed readily and are mildly exothermic; however, in some cases, the addition of a catalyst such as dibutyl tin dilaurate or 1,4-diazabicyclooctane may be used.

Alternative procedures of preparation of compounds XIIa, XIIb and XIIc respectively from the appropriate chlorocarbonate, chlorothiocarbonate and isocyanate is described in European Patent Application No. 1515.

Compounds of Formula I in which $R_2$ is $$-NHCB,$$

$HNO_2SCF_3$ or $-HNO_2SCH_3$ are prepared from the corresponding amino compound. The amino substituent in compound XIV can be converted readily to the amide (XIVa) or sulfonamide (XIVb) of this invention by reaction thereof respectively with the appropriate acid chloride (Equation 11) or sulfonyl chloride (Equation 12).

Equation 11

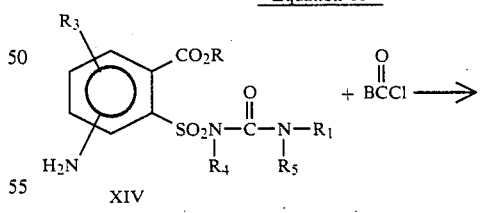

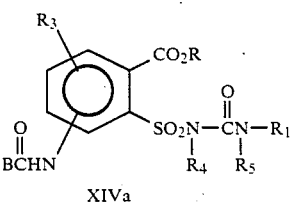

Equation 12

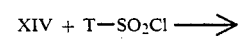

-continued

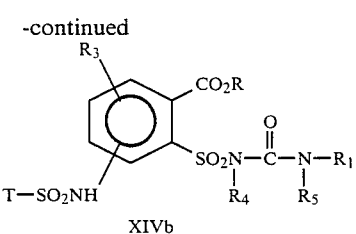

XIVb

T = CH₃ or CF₃

Compounds of Formula XIV can be prepared from the corresponding nitro compounds by catalytic hydrogenation as shown in Equation 13.

Equation 13

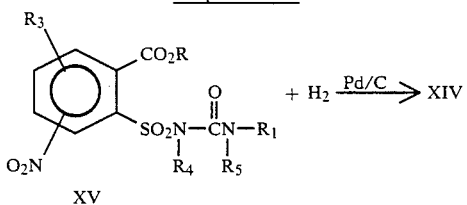

The procedures of Equations 11, 12 and 13 are described in European Patent Application No. 1515.

The synthesis of heterocyclic amines has been reviewed in "The Chemistry of Heterocyclic Compounds" a series published by Interscience Publ., New York and London. 2-Aminopyrimidines are described by D. J. Brown in "The Pyrimidines", Vol. XVI of this series. The 2-amino-1,3,5-triazines are reviewed by K. R. Huffman and in "The Triazines" of this same series. The synthesis of triazines are also described by F. C. Schaefer, U.S. Pat. No. 3,154,547 and K. R. Huffman and F. C. Schaeffer, J. Org. Chem. 28, 1816–1821 (1963).

The preparation of agriculturally suitable salts of the compounds of Formula I, as well as starting materials and intermediates for said compounds, not otherwise described herein, is disclosed in my application Ser. Nos. 824,805, filed August 15, 1977 and 840,389, filed October 6, 1977, the contents of which are incorporated herein by reference.

The compounds of this invention and their preparation are further illustrated by the following examples wherein temperatures are given in degrees centigrade and parts by weight unless otherwise indicated.

EXAMPLE 1

1-{2-{[(4,6-dimethoxypyrimidin-2-yl)aminocarbonyl]aminosulfonyl}benzoyl}-2,3-dihydro-1H-indole To 1.44 g of trimethylaluminum in 100 ml of methylene chloride was added 2.4 g of indoline with stirring at ambient temperature. To this mixture was added 3.0 g of N-[(4,6-dimethoxypyrimidin-2-yl)aminocarbonyl]-2-methoxycarbonylbenzenesulfonamide and the solution refluxed for 18 hours. The reaction mixture was treated with aqueous hydrochloric acid and the precipitated product (0.7 g) was found to be pure by thin layer chromatography (TLC) on silica gel with an eluting solvent of ethyl acetate and hexane, 1:1; m.p. 224°–225° C.; IR: 3200 cm⁻¹ NH, 1740 cm⁻¹ sulfonylurea carbonyl, 1640 cm⁻¹ amide carbonyl.

NMR: in trifluoroacetic acid-D, 3.1 ppm, T, 2H, methylene next to nitrogen in indoline ring, 4.1 ppm S, 6H, OCH₃ on pyrimidine ring, 6.3 ppm S, 1H, pyrimidine hydrogen in position 5, methylene of indoline ring next to aromatic ring under OCH₃ peak, 7.2–8.6 ppm, M, 8H, aromatic.

EXAMPLE 2

Methyl 2-{[(4,6-dimethoxypyrimidin-2-yl)aminocarbonyl]aminosulfonyl}-5-[(1,1-dimethylethylamino)carbonylamino]benzoate To 0.5 g of methyl 4-amino-2-{[(4,6-dimethoxypyrimidin-2-yl)aminocarbonyl]aminosulfonyl}benzoate in 50 ml of methylene chloride was added 4 ml of t-butyl isocyanate. The solution was stirred at ambient temperature for 18 hours. Evaporation of solvent and chromatography of the residue on silica gel with CH₂Cl₂/hexane 1:1 as eluents gave 0.1 g of pure product, m.p. 186°–8° C. IR, 3400 cm⁻¹ NH, 1730 cm⁻¹ and 1680 cm⁻¹ sulfonylurea carbonyl and urea carbonyl. NMR, 1.4 ppm, t-butyl-, S; 3.9 ppm OCH₃ of ester, S; 4.0 ppm, OCH₃ of pyrimidine, S; 5.8 ppm, CH of pyrimidine ring, S; 7.6–8.3 ppm, aromatic protons, M.

EXAMPLE 3

2-Oxiranylmethyl 2-[[(4,6-dimethoxypyrimidin-2-yl)aminocarbonyl]aminosulfonyl]benzoate To 1.75 g of 2-(4,6-dimethoxypyrimidin-2-ylaminocarbonylsulfonyl)benzoic acid is added 0.51 g of triethylamine in 10 ml of tetrahydrofuran and 0.48 g of epichlorohydrin in 10 ml of tetrahydrofuran. The mixture is heated to reflux for 1.5 hours, filtered, and the tetrahydrofuran evaporated in vacuo. The residue is dissolved in ethyl acetate and washed with water and aqueous sodium bicarbinate. The organic phase was dried over magnesium sulfate, filtered and the solvent evaporated in vacuo. The resultant product is recrystallized from a methylene chloride and 1-chlorobutane mixture.

EXAMPLE 4

N-[(4,6-dimethylpyrimidin-2-yl)aminocarbonyl]-2-ethoxyaminocarbonylbenzenesulfonamide To 2.9 g of trimethylaluminum in 100 ml of methylene chloride is added 2.0 g of ethoxyamine hydrochloride with stirring at ambient temperature. To this mixture is added 3.0 g of N-[(4,6-dimethylpyrimidin-2-yl)aminocarbonyl]-2-methoxycarbonylbenzenesulfonamide and the solution is refluxed for 18 hours. The reaction mixture is treated with aqueous hydrochloric acid and the resulting precipitated product is purified by chromatography.

EXAMPLE 5

2-Methoxycarbonyl-5-isocyanato-N-[(4-methoxy-6-methyl-1,3,5-triazin-2-yl)aminocarbonyl]benzenesulfonamide To 27 g of 2-methoxycarbonyl-5-isocyanatobenzenesulfonylisocyanate in 250 ml of anhydrous acetonitrile is added in small portions at ambient temperatures, 14 g of 2-amino-4-methoxy-6-methyl-1,3,5-triazine, the mixture is then stirred at ambient temperature for 16 hours. The resultant product, a white precipitate is removed by filtration and dried in vacuo.

EXAMPLE 6

Methyl 2-[[(4-methoxymethyl-6-methylthio-1,3,5-triazin-2-yl)aminocarbonyl]aminosulfonyl]benzoate To a solution of 0.8 g of 4-methoxymethyl-6-methylthio-2-amino-1,3,5-triazine in 15 ml of anhydrous methylene chloride was added 1.5 g of 2-methoxycarbonylbenzenesulfonylisocyanate. The mixture was heated for one hour and then stirred at ambient temperature for 18 hours. Solvent was removed in vacuo and the residue was triturated with 1-chlorobutane (50 ml) and filtered to give 1.7 g of the desired product, m.p. 147°–149° C. mmr: 2.6 ppm δ, 3H; 3.4 ppm δ, 3H; 3.85 ppm δ, 3H; 4.45 δ, 2H; 7.65–8.5 broad, 4H.

EXAMPLE 7

4-Methoxymethyl-6-methylthio-2-amino-1,3,5-triazine

Methoxyacetonitrile (35.5 g), sodium methoxide (25 g) and methanol (250 ml) were stirred at ambient temperature for 18 hours. Ammonium chloride (30 g) was added and the mixture stirred for one hour. The solvent was removed and the residue triturated with ether (150 ml) and then redissolved in methanol (250 ml). Sodium methoxide (26 g) in methanol (250 ml) was added to the mixture which was then rapidly filtered. The filtrate was added to dimethyl N-cyanocarbonimidodithioate (73 g) with stirring. After 3 hours of stirring at ambient temperature the solvent was removed and the residue washed with water and 1-chlorobutane. The solid (45 g) was an equal mixture of the desired methylthio compound and the corresponding methoxy compound. Isolation of the desired methylthio compound was achieved by preparative liquid chromatography (20 g). m.p. 134°–136° C. mmγ (DMSO-$d_6$) 2.4 ppm δ, 3H; 3.3 ppm δ, 3H; 4.14 ppm δ, 2H.

By application of one or more of the procedures of Examples 1–7 and/or the methods described above, with the appropriate reactants, the compounds of Tables I to VIII can be prepared.

TABLE I

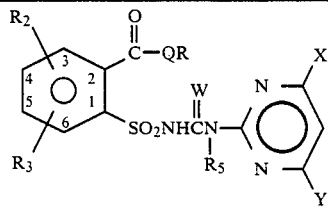

| QR | $R_2$ | $R_3$ | W | $R_5$ | X | Y | m.p. (°C.) |
|---|---|---|---|---|---|---|---|
| OCH₂CHCH₂ (epoxide) | H | H | O | H | CH₃ | H | |
| OCH₂CHCH₂ (epoxide) | 5-F | H | O | H | H | Cl | |
| OCH₂CHCH₂ (epoxide) | 5-Cl | H | O | H | OCH₃ | OCH₃ | |
| OCH₂CHCH₂ (epoxide) | 5-Br | H | O | H | CH₃ | OCH₃ | |
| OCH₂CHCH₂ (epoxide) | 5-NO₂ | H | O | H | CH₃ | OCH₃ | |
| OCH₂CHCH₂ (epoxide) | 5-OCH₃ | H | O | H | CH₃ | OCH₃ | |
| OCH₂CHCH₂ (epoxide) | 5-CH₃ | H | O | H | CH₃ | CH₃ | |
| OCH₂CHCH₂ (epoxide) | 5-i-C₃H₇ | H | O | H | CH₃ | OC₂H₅ | |
| OCH₂CHCH₂ (epoxide) | 5-SCH₃ | H | O | H | CH₃ | OCH₃ | |
| OCH₂CHCH₂ (epoxide) | 5-Cl | 3-Cl | O | H | CH₃ | OCH₃ | |
| OCH₂CHCH₂ (epoxide) | 5-Cl | 3-CH₃ | O | H | CH₃ | OCH₃ | |

TABLE I-continued

Structure: benzene ring with R2 at position 3/4/5, R3 at position 6, C(=O)-QR at position 2, SO2NHC(=W)N(R5)- linked to pyrimidine with X and Y substituents.

| QR | R2 | R3 | W | R5 | X | Y | m.p. (°C.) |
|---|---|---|---|---|---|---|---|
| OCH2CHCH2 (epoxide) | 5-F | 3-Cl | O | H | CH3 | OCH3 | |
| OCH2CHCH2 (epoxide) | 5-NO2 | 3-Cl | O | H | CH3 | OCH3 | |
| OCH2CHCH2 (epoxide) | 5-Br | 3-Br | O | H | CH3 | OCH3 | |
| OCH2CHCH2 (epoxide) | 6-Cl | H | S | H | CH3 | CH2OCH3 | |
| OCH2CHCH2 (epoxide) | H | H | O | H | CH3 | OCH2CH2OC2H5 | |
| OCH2CHCH2 (epoxide) | H | H | O | H | CH3 | OCH2CH2CH2OCH3 | |
| OCH2CHCH2 (epoxide) | H | H | O | H | CH3 | OCH(CH3)CO2CH3 | |
| OCH2CHCH2 (epoxide) | H | H | O | H | CH3 | OCH2CH2CO2CH3 | |
| OCH2CHCH2 (epoxide) | H | H | O | H | CH3 | OCH2CO2C2H5 | |
| OCH2CHCH2 (epoxide) | H | H | O | CH3 | OCH3 | OCH3 | |
| OCH2CHCH2 (epoxide) | H | H | O | CH3 | OCH3 | OCH3 | |
| OCH2CHCH2 (epoxide) | 5-Cl | H | O | CH3 | OCH3 | CH3 | |
| OCH2CHCH2 (epoxide) | 6-Cl | H | O | CH3 | OCH3 | OC2H5 | |
| OCH2CHCH2 (epoxide) | 3-CH3 | H | O | CH3 | OCH3 | OCH3 | |
| OCH2CHCH2 (epoxide) | H | H | O | H | CH3 | SCH2COOCH3 | |
| OCH2CHCH2 (epoxide) | H | H | O | H | CH3 | S(CH2)2OC2H5 | |
| OCH2CHCH2 (epoxide) | H | H | O | H | CH3 | S(CH2)2COOC2H5 | |

TABLE I-continued

| QR | R₂ | R₃ | W | R₅ | X | Y | m.p. (°C.) |
|---|---|---|---|---|---|---|---|
| OCH₂CHCH₂ (epoxide) | H | H | O | H | CH₃ | CH₃ | |
| OCH₂CHCH₂ (epoxide) | H | H | O | H | CH₃ | OCH₃ | |
| OCH₂CHCH₂ (epoxide) | H | H | O | H | OCH₃ | OCH₃ | |
| —N(indoline) | H | H | O | H | —CH₃ | SCH(CH₃)—CO₂CH₃ | |
| —N(indoline) | H | H | O | H | —CH₃ | OCH₂CO₂C₂H₅ | |
| —N(indoline) | H | H | O | H | —CH₃ | SCH₂CO₂C₂H₅ | |
| —N(indoline) | H | H | O | H | —CH₃ | —OCH₂CH₂OC₂H₅ | |
| —N(indoline) | H | H | O | H | —CH₃ | —SCH₂CH₂SCH₃ | |
| —N(indoline) | H | H | O | H | —CH₃ | —SCH₂CH₂S(O)₂CH₃ | |

TABLE I-continued

| QR | R2 | R3 | W | R5 | X | Y | m.p. (°C.) |
|---|---|---|---|---|---|---|---|
| indolinyl | H | H | O | H | —CH₃ | —SCH₂CH₃ | |
| indolinyl | H | H | O | H | —CH₃ | —SCH₂C≡CH | |
| indolinyl | 5-CF₃ | H | O | H | —CH₃ | OCH₃ | |
| indolinyl | 5-N(CH₃)₂ | H | O | H | —CH₃ | OCH₃ | |
| indolinyl | 5-SO₂CH₃ | H | O | H | —CH₃ | OCH₃ | |
| indolinyl | 5-CN | H | O | H | CH₃ | OCH₃ | |
| indolinyl | 5-NH₂ | H | O | H | CH₃ | OCH₃ | |

TABLE I-continued
[Structure diagram shown at top of table]
| QR | R₂ | R₃ | W | R₅ | X | Y | m.p. (°C.) |
|---|---|---|---|---|---|---|---|
| 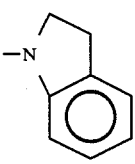 | 4-Cl | 5-Cl | O | H | OCH₃ | CH₃ | |
| 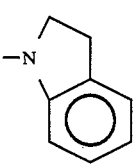 | 4-Cl | 5-Cl | O | H | OCH₃ | OCH₃ | |
| 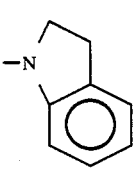 | 4-F | H | O | H | OCH₃ | CH₃ | |
| 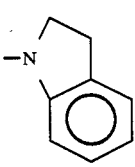 | 4-Br | H | O | H | OCH₃ | CH₃ | |
| 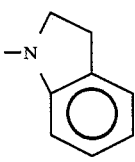 | H | H | O | H | CH₃ | OCH₂CF₃ | |
| 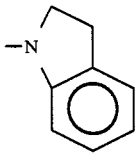 | H | H | O | H | CH₃ | OCHCO₂CH₃<br>\|<br>CH₃ | |
| 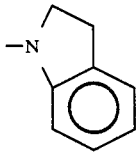 | H | H | O | H | CH₃ | OCH₂CO₂CH₃ | |

TABLE I-continued
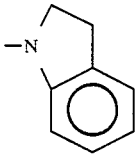
| QR | R₂ | R₃ | W | R₅ | X | Y | m.p. (°C.) |
|---|---|---|---|---|---|---|---|
| 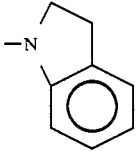 | H | H | O | H | CH₃ | CH₂OCH₃ | |
| 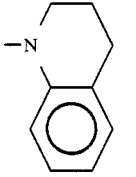 | H | H | O | CH₃ | CH₃ | CH₃ | |
| 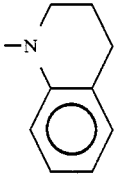 | H | H | O | H | OCH₂CH₂OCH₃ | OCH₂CH₂OCH₃ | |
| 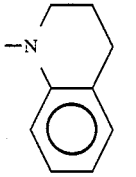 | H | H | O | H | —OCH₃ | n-C₄H₉ | |
| 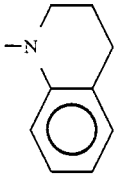 | H | H | O | H | —OCH₃ | —CH₂CH₂CH₂OCH₃ | |
| 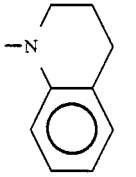 | H | H | O | H | —OCH₃ | —CH₂CH₂CN | |
| 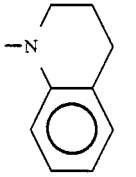 | H | H | O | H | —OCH₃ | —CH₂CO₂CH₃ | |

TABLE I-continued

|QR|R2|R3|W|R5|X|Y|m.p. (°C.)|
|---|---|---|---|---|---|---|---|
|−N(tetrahydroquinoline)|H|H|O|H|−OCH$_3$|−CCl$_3$||
|−N(tetrahydroquinoline)|H|H|O|H|−OCH$_3$|−CH(CH$_3$)−CO$_2$CH$_3$||
|−N(tetrahydroquinoline)|H|H|O|H|CH$_3$|−(CH$_2$)$_3$CH$_2$Cl||
|−N(tetrahydroquinoline)|H|H|O|H|−OCH$_3$|−CH$_2$C≡C−CH$_3$||
|−N(tetrahydroquinoline)|H|H|O|H|−OCH$_3$|−CH$_2$C≡C−CH$_2$Cl||
|−N(tetrahydroquinoline)|H|H|O|H|−OCH$_3$|−NH−n-C$_4$H$_9$||
|−N(tetrahydroquinoline)|H|H|O|H|−OCH$_3$|−N(CH$_3$)−(CH$_2$)$_2$CN||

TABLE I-continued
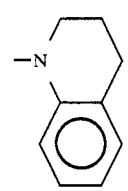
| QR | R₂ | R₃ | W | R₅ | X | Y | m.p. (°C.) |
|---|---|---|---|---|---|---|---|
| 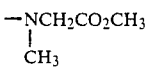 | H | H | O | H | —OCH₃ | —N(CH₃)CH₂CO₂CH₃ | |
| 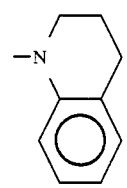 | H | H | O | H | —OCH₃ | —NH(CH₂)₂CO₂CH₃ | |
| 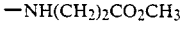 | H | H | O | H | —CH₃ | —N(H)CH₂CH₂OCH₃ | |
| 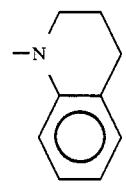 | H | H | O | H | —OCH₃ | 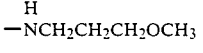 | |
| 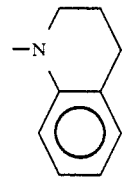 | H | H | O | H | —CH₃ | —O(CH₂)₃CH₃ | |
| 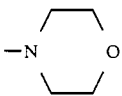 | H | H | O | H | —CH₃ | —OCH₂CH₂Br | |

TABLE I-continued

[Structure shown: benzene ring with R2 at position 3-4-5, R3 at position 5-6, C(=O)-QR at position 2, and SO2NHC(=W)N(R5)-pyrimidine (with X and Y substituents) at position 1]

| QR | R2 | R3 | W | R5 | X | Y | m.p. (°C.) |
|---|---|---|---|---|---|---|---|
| [1,2,3,4-tetrahydroquinolin-1-yl] | H | H | O | H | —CH₃ | —OCH₂CCl₃ | |
| [1,2,3,4-tetrahydroquinolin-1-yl] | H | H | O | H | —CH₃ | —OCH₂CH₂CH₂CN | |
| [1,2,3,4-tetrahydroquinolin-1-yl] | H | H | O | H | —CH₃ | —OCH₂CH=CH₂ | |
| [1,2,3,4-tetrahydroquinolin-1-yl] | H | H | O | H | CH₃ | CH₃ | |
| [1,2,3,4-tetrahydroquinolin-1-yl] | H | H | O | H | CH₃ | OCH₃ | |
| [1,2,3,4-tetrahydroquinolin-1-yl] | H | H | O | H | OCH₃ | OCH₃ | |
| [indolin-1-yl] | 5-NO₂ | H | O | H | CH₃ | CH₃ | |

TABLE I-continued
| QR | R2 | R3 | W | R5 | X | Y | m.p. (°C.) |
|---|---|---|---|---|---|---|---|
| 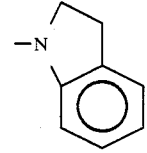 | 5-NO2 | H | O | H | CH3 | OCH3 | |
| 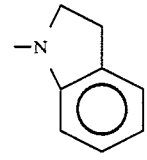 | 5-NO2 | H | O | H | OCH3 | OCH3 | |
| 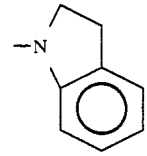 | 5-NH2 | H | O | H | CH3 | OCH3 | |
| 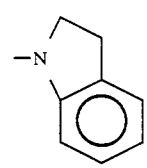 | 5-NH2 | H | O | H | OCH3 | OCH3 | |
| 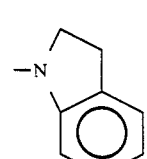 | 5-NH2 | H | O | H | CH3 | CH3 | |
| 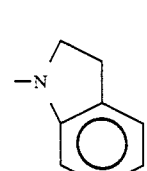 | 5-Cl | H | O | H | OCH3 | OCH3 | |
| 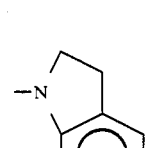 | 5-Cl | H | O | H | OCH3 | CH3 | |

TABLE I-continued

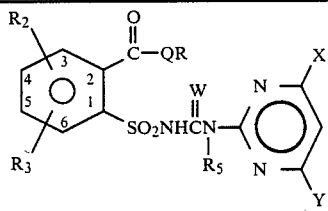

| QR | R₂ | R₃ | W | R₅ | X | Y | m.p. (°C.) |
|---|---|---|---|---|---|---|---|
| ![indoline]  | 5-Cl | H | O | H | $CH_3$ | $CH_3$ | |
| ![indoline] | H | H | O | H | $OCH_2CH_3$ | $OCH_2CH_3$ | |
| ![indoline] | H | H | O | H | $OCH_3$ | $OCH_3$ | 224–225° |
| ![indoline] | H | H | O | H | $CH_3$ | $OCH_3$ | |
| ![indoline] | H | H | O | H | $CH_3$ | $CH_3$ | |
| H NOCH₃ | H | H | O | H | $CH_3$ | $CH_3$ | |
| H NOCH₃ | 5-Cl | H | O | H | $OCH_3$ | $OCH_3$ | |
| H NOCH₃ | 4-Cl | Cl | O | H | $CH_3$ | $OCH_3$ | |
| H NOCH₃ | H | H | O | H | $OCH_3$ | $OCH_3$ | |
| H NOCH₃ | 5-$NO_2$ | H | O | H | $OCH_3$ | $OCH_3$ | |
| H NOCH₃ | 5-$CF_3$ | H | O | H | $OCH_3$ | $OCH_3$ | |
| H NOCH₃ | 5-$SO_2CH_3$ | H | O | H | $OCH_3$ | $CH_3$ | |
| H NOC₂H₅ | 5-Cl | H | O | H | $CH_3$ | $CH_3$ | |

TABLE I-continued

Structure: benzene ring (positions 1-6) with R₂ at 3, R₃ at 5, C(=O)-QR at position 2 (carboxylate), and SO₂NHC(=W)N(R₅)-pyrimidine at position 1; pyrimidine bears X and Y.

| QR | R₂ | R₃ | W | R₅ | X | Y | m.p. (°C.) |
|---|---|---|---|---|---|---|---|
| H, NOC₂H₅ | H | H | O | H | OCH₃ | OCH₃ | |
| H, NOC₂H₅ | H | H | O | H | OCH₃ | CH₃ | |
| H, NOC₂H₅ | 5-NH₂ | H | O | H | OCH₃ | CH₂OCH₃ | |
| H, NOC₂H₅ | 5-NH₂ | H | O | H | CH₃ | OCH₂CO₂CH₃ | |
| OCH₂CHCH₂ (epoxide) | H | H | O | H | CH₃ | F | |
| OCH₂CHCH₂ (epoxide) | H | H | O | H | CH₃ | Br | |
| OCH₂CHCH₂ (epoxide) | H | H | O | H | CH₃ | CO₂CH₃ | |
| OCH₂CHCH₂ (epoxide) | H | H | O | H | OCH₃ | CH₂CO₂CH₃ | |
| OCH₂CHCH₂ (epoxide) | H | H | O | H | OCH₃ | CH₂CO₂H | |
| OCH₂CHCH₂ (epoxide) | H | H | O | H | OCH₃ | CH₂CO₂—n-C₄H₉ | |
| OCH₂CHCH₂ (epoxide) | H | H | O | H | OCH₃ | (CH₂)₃CO₂—i-C₃H₇ | |
| OCH₂CHCH₂ (epoxide) | H | H | O | H | OCH₃ | CH₂CO₂—n-C₆H₁₃ | |
| OCH₂CHCH₂ (epoxide) | H | H | O | H | CH₃ | NH(CH₂)₂CO₂—i-C₃H₇ | |
| OCH₂CHCH₂ (epoxide) | H | H | O | H | CH₃ | NHCH₂C(=O)N(CH₃)₂ | |
| OCH₂CHCH₂ (epoxide) | H | H | O | H | CH₃ | NHCH₂C(=O)N(OCH₃)(CH₃) | |
| OCH₂CHCH₂ (epoxide) | H | H | O | H | CH₃ | CH₃N—CH(CH₃)—C(=O)—NH—t-C₄H₉ | |
| OCH₂CHCH₂ (epoxide) | H | H | O | H | CH₃ | CH₃N—CH₂—C(=O)—N(C₂H₅)₂ | |

TABLE I-continued

[Structure: benzene ring with R2 at position 3, R3 at position 6, C(=O)-QR at position 2, SO2NHC(=W)N(R5)- linked to pyrimidine with X and Y substituents]

| QR | R₂ | R₃ | W | R₅ | X | Y | m.p. (°C.) |
|---|---|---|---|---|---|---|---|
| OCH₂CHCH₂ (epoxide) | H | H | O | H | CH₃ | CH₃N(−)—CH₂CO—n-C₄H₉ (with C=O) | |
| OCH₂CHCH₂ (epoxide) | H | H | O | H | CH₃ | CH₃N(−)—n-C₆H₁₃ | |

TABLE II

[Structure: benzene ring with R2, R3, C(=O)-QR, SO2N(R4)C(=W)N(R5)- linked to triazine with X and Y]

| QR | R₂ | R₃ | W | R₄ | R₅ | X | Y | m.p. (°C.) |
|---|---|---|---|---|---|---|---|---|
| OCH₂CHCH₂ (epoxide) | H | H | O | H | H | CH₃ | CH₃ | |
| OCH₂CHCH₂ (epoxide) | H | H | O | H | CH₃ | OCH₃ | OCH₃ | |
| OCH₂CHCH₂ (epoxide) | H | H | O | H | H | H | H | |
| OCH₂CHCH₂ (epoxide) | H | H | S | H | H | CH₃ | OCH₃ | |
| OCH₂CHCH₂ (epoxide) | 3-Cl | H | O | H | H | CH₃ | OCH₃ | |
| OCH₂CHCH₂ (epoxide) | 3-CH₃ | H | O | H | H | OCH₃ | OCH₃ | |
| OCH₂CHCH₂ (epoxide) | 3-Cl | 5-Cl | O | H | H | OC₂H₅ | OCH₃ | |
| OCH₂CHCH₂ (epoxide) | 5-NO₂ | H | O | H | H | OC₂H₅ | OCH₃CH₂OCH₃ | |
| OCH₂CHCH₂ (epoxide) | H | H | O | H | H | OCH₃ | OCH₂CH₂CH₂OCH₃ | |
| OCH₂CHCH₂ (epoxide) | 3-Cl | 6-Cl | O | H | H | CH₃CH₂O | CH₃O | |
| OCH₂CHCH₂ (epoxide) | H | H | O | H | H | CH₃O | CF₃ | |

TABLE II-continued

| QR | R₂ | R₃ | W | R₄ | R₅ | X | Y | m.p. (°C.) |
|---|---|---|---|---|---|---|---|---|
| OCH₂CHCH₂ (epoxide) | 3-OCH₃ | H | S | H | H | CH₃ | OC₂H₅ | |
| OCH₂CHCH₂ (epoxide) | 5-SCH₃ | H | O | H | H | CH₃ | O(CH₂)₂OC₂H₅ | |
| OCH₂CHCH₂ (epoxide) | 5-F | H | O | H | H | OCH₃ | O(CH₂)₂COOC₂H₅ | |
| OCH₂CHCH₂ (epoxide) | 5-CH₃ | H | O | H | CH₃ | OCH₃ | OCH₃ | |
| OCH₂CHCH₂ (epoxide) | 5-F | H | O | H | CH₃ | CH₃ | OCH₃ | |
| OCH₂CHCH₂ (epoxide) | 3-Cl | H | O | H | CH₃ | OCH₃ | N(CH₃)₂ | |
| OCH₂CHCH₂ (epoxide) | 5-CH₃ | H | O | H | H | CH₃ | OCH₃ | |
| OCH₂CHCH₂ (epoxide) | 5-CN | H | O | H | H | OCH₃ | OCH₃ | |
| OCH₂CHCH₂ (epoxide) | 5-CF₃ | H | O | H | H | OCH₃ | OCH₃ | |
| OCH₂CHCH₂ (epoxide) | 5-SO₂CH₃ | H | O | H | H | OCH₃ | OCH₃ | |
| OCH₂CHCH₂ (epoxide) | 5-N(CH₃)₂ | H | O | H | H | OCH₃ | OCH₃ | |
| OCH₂CHCH₂ (epoxide) | 5-NH₂ | H | O | H | H | OCH₃ | OCH₃ | |
|  | H | H | O | H | H | OCH₃ | SCH₃ | |
| 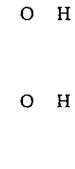 | H | H | O | H | H | OCH₃ | SCH₂COOCH₃ | |

TABLE II-continued

[Structure: benzene ring with positions 1-6, substituents R2 (position 3), R3 (position 5), with C(=O)-QR at position 2, and SO2NHC(=W)N(R4)(R5)- at position 1, attached to a triazine ring with X and Y substituents]

| QR | R2 | R3 | W | R4 | R5 | X | Y | m.p. (°C.) |
|---|---|---|---|---|---|---|---|---|
| -N(indoline) | H | H | O | H | H | OCH3 | S(CH2)2OC2H5 | |
| -N(indoline) | 4-Cl | 5-Cl | O | H | H | OCH3 | OCH3 | |
| -N(indoline) | 4-F | H | O | H | H | OCH3 | OCH3 | |
| -N(indoline) | 4-Cl | 5-Cl | O | H | H | OCH3 | CH3 | |
| -N(indoline) | 4-F | H | O | H | H | OCH3 | CH3 | |
| -N(indoline) | 4-Br | H | O | H | H | OCH3 | CH3 | |
| -N(indoline) | 4-Cl | H | O | H | H | OCH3 | OCH3 | |

TABLE II-continued

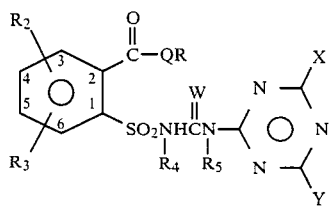

| QR | R₂ | R₃ | W | R₄ | R₅ | X | Y | m.p. (°C.) |
|---|---|---|---|---|---|---|---|---|
| -N(indoline-like bicyclic) | H | H | O | H | H | CH₃ | N(CH₃)₂ | |
| -N(indoline-like bicyclic) | H | H | O | H | H | OCH₃ | OCH₂CF₃ | |
| -N(indoline-like bicyclic) | H | H | O | H | H | OCH₃ | OCH₂CH₂OCH₃ | |
| -N(indoline-like bicyclic) | H | H | O | H | H | OCH₃ | OCH₂CH₂OCH₂CH₃ | |
| -N(indoline-like bicyclic) | H | H | O | H | H | Cl | Cl | |
| -N(indoline-like bicyclic) | H | H | O | H | H | —OCH₂CH₂OCH₃ | —OCH₂CH₂OCH₃ | |
| -N(indoline-like bicyclic) | H | H | O | H | H | —OCH₃ | —CH₂CH₂OCH₃ | |

TABLE II-continued
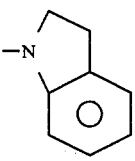
| QR | R₂ | R₃ | W | R₄ | R₅ | X | Y | m.p. (°C.) |
|---|---|---|---|---|---|---|---|---|
| 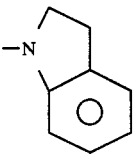 | H | H | O | H | H | —CH₃ | —CH₂CH₂OCH₃ | |
| 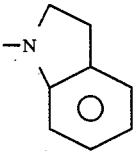 | H | H | O | H | H | —CH₃ | —CH₂CH₂CH₂OCH₃ | |
| 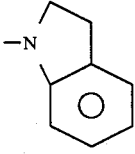 | H | H | O | H | H | —CH₃ | —OCH₂CO₂CH₃ | |
| 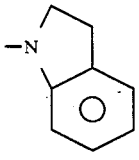 | H | H | O | H | H | —CH₃ | —OCH₂CH₂OCH₃ | |
| 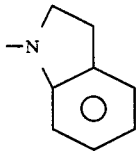 | H | H | O | H | H | —CH₃ | —OCH₂CF₃ | |
| 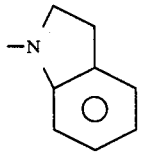 | H | H | O | H | H | —CH₃ | —OCH₂CH₂OCH₂CH₃ | |
|  | H | H | O | H | H | —CH₃ | —OCH₂CH₃ | |

TABLE II-continued
| QR | R2 | R3 | W | R4 | R5 | X | Y | m.p. (°C.) |
|---|---|---|---|---|---|---|---|---|
| 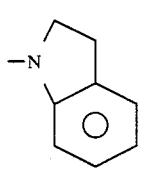 | H | H | O | H | H | —CH₃ | —OCHCO₂CH₃<br>\|<br>CH₃ | |
| 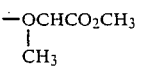 | H | H | O | H | H | CH₃ | CH₃ | |
| 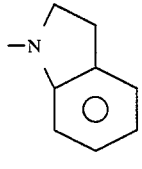 | H | H | O | H | H | CH₃ | OCH₃ | |
| 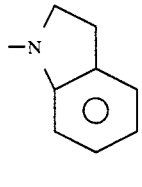 | H | H | O | H | H | OCH₃ | OCH₃ | |
| 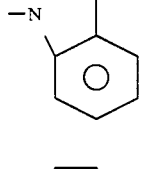 | H | H | O | H | H | —CH₃ | —OCH(CH₃)₂ | |
| 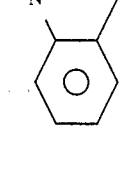 | H | H | O | H | H | —CH₃ | —OCH₂CH₂Cl | |
| 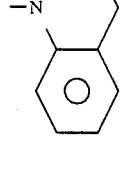 | H | H | O | H | H | —CH₃ | —OCH₂CCl₃ | |

TABLE II-continued
| QR | R₂ | R₃ | W | R₄ | R₅ | X | Y | m.p. (°C.) |
|---|---|---|---|---|---|---|---|---|
| 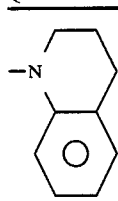 | H | H | O | H | H | —CH₃ | —OCH₂CH₂CN | |
| 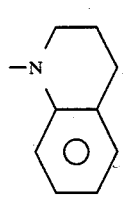 | H | H | O | H | H | —CH₃ | —OCH₂CH=CH₂ | |
| 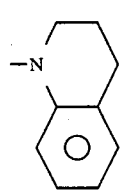 | H | H | O | H | H | —CH₃ | —OCH₂C≡CCH₃ | |
| 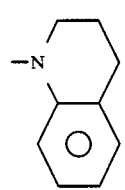 | H | H | O | H | H | CH₃ | OCH₃ | |
| 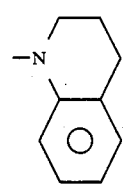 | H | H | O | H | H | OCH₃ | OCH₃ | |
| 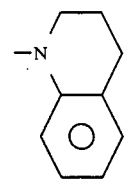 | H | H | O | H | H | —CH₃ | —OCH₂-⊲ | |
| 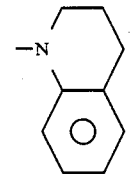 | H | H | O | H | H | —CH₃ | CH₃ | |

TABLE II-continued
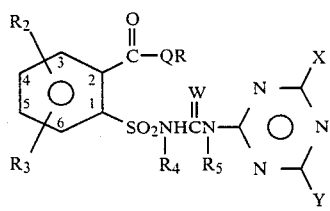
| QR | R₂ | R₃ | W | R₄ | R₅ | X | Y | m.p. (°C.) |
|---|---|---|---|---|---|---|---|---|
| (1,2,3,4-tetrahydroquinolin-1-yl) | H | H | O | H | H | —CH₃ | —SCH(CH₃)CO₂CH₃ | |
| (1,2,3,4-tetrahydroquinolin-1-yl) | H | H | O | H | H | CH₃ | —O(CH₂)₂OC₂H₅ | |
| (1,2,3,4-tetrahydroquinolin-1-yl) | H | H | O | H | H | CH₃ | —SCH₂CH₂SCH₃ | |
| (1,2,3,4-tetrahydroquinolin-1-yl) | H | H | O | H | H | CH₃ | —SCH₂CH₂S(O)₂CH₃ | |
| (1,2,3,4-tetrahydroquinolin-1-yl) | H | H | O | H | H | CH₃ | —OCH₂CH₂SC₂H₅ | |
| (1,2,3,4-tetrahydroquinolin-1-yl) | H | H | O | H | H | CH₃ | —OCH₂CH₂SCH₃ | |

TABLE II-continued
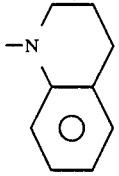
| QR | R₂ | R₃ | W | R₄ | R₅ | X | Y | m.p. (°C.) |
|---|---|---|---|---|---|---|---|---|
|  | H | H | O | H | H | $CH_3$ | $-SCH_2CH_3$ | |
| 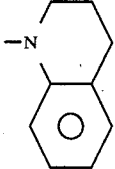 | H | H | O | H | H | $CH_3$ | $-SCH_2CH_2CN$ | |
| 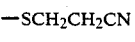 | H | H | O | H | H | $CH_3$ | $-SCH_2CH=CH_2$ | |
| 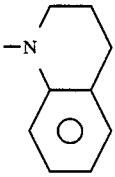 | H | H | O | H | H | H | $OCH_3$ | |
| 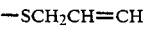 | H | H | O | H | H | $-OCH_3$ | $n\text{-}C_4H_9$ | |
| 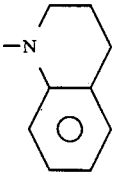 | H | H | O | H | H | $-OCH_3$ | $CH_2CH_2CH_2OCH_3$ | |
|  | H | H | O | H | H | $-OCH_3$ | $-CH_2CN$ | |

TABLE II-continued
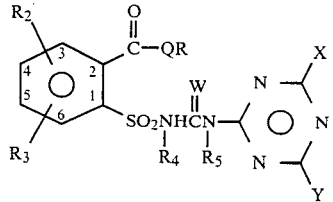
| QR | R₂ | R₃ | W | R₄ | R₅ | X | Y | m.p. (°C.) |
|---|---|---|---|---|---|---|---|---|
| tetrahydroquinolinyl | H | H | O | H | H | —OCH$_3$ | —CH$_2$CH$_2$CN | |
| tetrahydroquinolinyl | H | H | O | H | H | —OCH$_3$ | —(CH$_2$)$_3$CN | |
| tetrahydroquinolinyl | H | H | O | H | H | —OCH$_3$ | —(CH$_2$)$_2$CO$_2$CH$_3$ | |
| tetrahydroquinolinyl | H | H | O | H | H | —OCH$_3$ | —CH$_2$CH$_2$Cl | |
| tetrahydroquinolinyl | H | H | O | H | H | —OCH$_3$ | —(CH$_2$)$_3$Br | |
| tetrahydroquinolinyl | H | H | O | H | H | —OCH$_3$ | —CH$_2$CH=CHCH$_3$ | |

TABLE II-continued

| QR | R2 | R3 | W | R4 | R5 | X | Y | m.p. (°C.) |
|---|---|---|---|---|---|---|---|---|
| −N(1,2,3,4-tetrahydroquinolinyl) | H | H | O | H | H | OCH₃ | −CH₂C≡CCH₃ | |
| −N(1,2,3,4-tetrahydroquinolinyl) | H | H | O | H | H | OCH₃ | −NHnC₄H₉ | |
| −N(1,2,3,4-tetrahydroquinolinyl) | H | H | O | H | H | OCH₃ | −N(CH₃)(CH₂)₂CN | |
| −N(1,2,3,4-tetrahydroquinolinyl) | H | H | O | H | H | OCH₃ | −N(CH₃)CH₂CO₂CH₃ | |
| −N(1,2,3,4-tetrahydroquinolinyl) | H | H | O | H | H | OCH₃ | −N(H)CH₂CH₂CH₂OCH₃ | |
| −N(1,2,3,4-tetrahydroquinolinyl) | H | H | O | H | H | OCH₃ | morpholino | |
| CH₂CHCH₂ (epoxide) | H | H | O | CH₃ | H | CH₃ | OCH₃ | |
| CH₂CHCH₂ (epoxide) | H | H | O | CH₃ | CH₃ | CH₃ | OCH₃ | |

TABLE II-continued

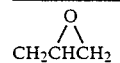

| QR | R₂ | R₃ | W | R₄ | R₅ | X | Y | m.p. (°C.) |
|---|---|---|---|---|---|---|---|---|
| $\underset{CH_2CHCH_2}{\overset{O}{\triangle}}$ | 5-NO₂ | H | O | CH₃ | CH₃ | H | OCH₂CH₂CO₂CH₃ | |
| $\underset{CH_2CHCH_2}{\overset{O}{\triangle}}$ | 6-Cl | H | O | CH₃ | H | CH₃ | O—CH(CH₃)CO₂CH₃ | |
| $\underset{CH_2CHCH_2}{\overset{O}{\triangle}}$ | H | H | O | CH₃ | CH₃ | OCH₃ | N(CH₃)₂ | |
| $\underset{CH_2CHCH_2}{\overset{O}{\triangle}}$ | H | H | O | CH₃ | H | OCH₃ | NH(CH₃) | |
| $\underset{CH_2CHCH_2}{\overset{O}{\triangle}}$ | H | H | O | CH₃ | H | OCH₃ | CH₃ | |
| $\underset{CH_2CHCH_2}{\overset{O}{\triangle}}$ | H | H | O | CH₃ | H | CH₃ | CH₃ | |
| $\underset{CH_2CHCH_2}{\overset{O}{\triangle}}$ | H | H | O | CH₃ | H | OCH₃ | OCH₃ | |
| $\underset{CH_2CHCH_2}{\overset{O}{\triangle}}$ | H | H | O | H | H | OCH₃ | OCH₃ | |
| $\underset{CH_2CHCH_2}{\overset{O}{\triangle}}$ | H | H | O | H | H | OCH₃ | CH₃ | |
| $\underset{CH_2CHCH_2}{\overset{O}{\triangle}}$ | 5-CN | H | O | H | H | CH₃ | OCH₃ | |
| $\underset{CH_2CHCH_2}{\overset{O}{\triangle}}$ | 5-CF₃ | H | O | H | H | CH₃ | OCH₃ | |
| $\underset{CH_2CHCH_2}{\overset{O}{\triangle}}$ | 5-SO₂CH₃ | H | O | H | H | CH₃ | OCH₃ | |
| $\underset{CH_2CHCH_2}{\overset{O}{\triangle}}$ | 5-OCH₃ | H | O | H | H | CH₃ | OCH₃ | |
| H NOCH₃ | 5-CF₃ | H | O | H | H | CH₃ | CH₃ | |
| H NOCH₃ | 5-Cl | H | O | H | H | OCH₃ | CH₃ | |
| H NOCH₃ | 5-Cl | H | O | H | H | CH₃ | OCH₃ | |
| H NOCH₃ | H | H | O | H | H | OCH₃ | OCH₃ | |
| H NOCH₃ | 4-Cl | 5-Cl | O | H | H | CH₃ | CH₃ | |
| H NOCH₃ | H | H | O | H | H | CH₃ | CH₃ | |

TABLE II-continued

Structure: benzene ring with R2 at position 3, R3 at position 5/6, C(=O)-OR at position 2, SO₂N(R4)C(=W)N(R5)- at position 1, linked to a pyrimidine ring bearing X and Y substituents.

| QR | R₂ | R₃ | W | R₄ | R₅ | X | Y | m.p. (°C) |
|---|---|---|---|---|---|---|---|---|
| H, NOCH₃ | H | H | O | H | H | CH₃ | OCH₃ | |
| H, NOCH₃ | 5-NO₂ | H | O | H | H | CH₃ | OCH₃ | |
| H, NOC₂H₅ | 5-Cl | H | O | H | H | CH₃ | OCH₃ | |
| H, NOC₂H₅ | H | H | O | H | H | CH₃ | OCH₂CO₂CH₃ | |
| H, NOC₂H₅ | 5-CF₃ | H | O | H | H | CH₃ | OCH(CH₃)—CO₂CH₃ | |
| H, NOC₂H₅ | 5-CN | H | O | H | H | CH₃ | OCH₂CCl₃ | |
| H, NOC₂H₅ | 5-Cl | 6-Cl | O | H | H | CH₃ | OCH₂CH=CH₂ | |
| H, NOC₂H₅ | 5-NO₂ | H | O | H | H | CH₃ | O(CH₂)₂OCH₃ | |
| H, NOC₂H₅ | 4-CH₃ | H | O | H | H | CH₃ | OCH₂CN | |

TABLE III

Structure: benzene ring with R2, R3 substituents, C(=O)-OR group, SO₂NHC(=W)NH- linkage to pyrimidine ring bearing X₁ and Y₁.

| QR | R₂ | R₃ | W | X₁ | Y₁ | m.p. (°C) |
|---|---|---|---|---|---|---|
| OCH₂CHCH₂ (epoxide) | H | H | O | OCH₃ | CH₃ | |
| OCH₂CHCH₂ (epoxide) | H | H | O | CH₃ | OCH₃ | |
| OCH₂CHCH₂ (epoxide) | 6-Cl | H | O | OCH₃ | OCH₃ | |
| OCH₂CHCH₂ (epoxide) | 3-Cl | 5-Cl | O | OCH₃ | C₂H₅ | |
| OCH₂CHCH₂ (epoxide) | 5-OCH₃ | H | O | OCH₃ | OCH₃ | |
| OCH₂CHCH₂ (epoxide) | 5-NO₂ | 3-Cl | O | OCH₃ | CH₂OCH₃ | |
| OCH₂CHCH₂ (epoxide) | 5-Cl | H | O | OCH₃ | OCH₃ | |
| OCH₂CHCH₂ (epoxide) | H | H | O | CH₃ | OC₂H₅ | |
| OCH₂CHCH₂ (epoxide) | 5-CN | H | O | CH₃ | OCH₃ | |
| OCH₂CHCH₂ (epoxide) | 5-CF₃ | H | O | CH₃ | OCH₃ | |
| OCH₂CHCH₂ (epoxide) | 5-SO₂CH₃ | H | O | CH₃ | OCH₃ | |

TABLE III-continued

| QR | R₂ | R₃ | W | X₁ | Y₁ | m.p. (°C.) |
|---|---|---|---|---|---|---|
| OCH₂CH(O)CH₂ (glycidyl) | H | H | O | CH₃ | CH₃ | |
| —N(indoline) | H | H | O | OCH₃ | CH₃ | |
| —N(indoline) | H | H | O | CH₃ | OCH₃ | |
| —N(indoline) | 6-Cl | H | O | OCH₃ | OCH₃ | |
| —N(indoline) | 3-Cl | 5-Cl | O | OCH₃ | C₂H₅ | |
| —N(indoline) | 5-OCH₃ | H | O | OCH₃ | OCH₃ | |
| —N(indoline) | 5-NO₂ | 3-Cl | O | OCH₃ | CH₂OCH₃ | |
| —N(indoline) | 5-Cl | H | O | OCH₃ | OCH₃ | |
| —N(indoline) | H | H | O | CH₃ | OC₂H₅ | |
| —N(indoline) | 5-CN | H | O | CH₃ | OCH₃ | |
| —N(indoline) | 5-CF₃ | H | O | CH₃ | OCH₃ | |
| —N(indoline) | 5-SO₂CH₃ | H | O | CH₃ | OCH₃ | |
| —N(tetrahydroquinoline) | H | H | O | CH₃ | CH₃ | |
| —N(tetrahydroquinoline) | H | H | O | OCH₃ | CH₃ | |
| —N(tetrahydroquinoline) | H | H | O | CH₃ | OCH₃ | |

TABLE III-continued

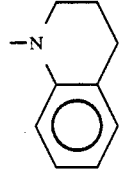

| QR | R2 | R3 | W | X1 | Y1 | m.p. (°C.) |
|---|---|---|---|---|---|---|
| 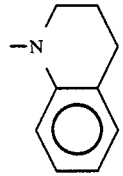 | 6-Cl | H | O | OCH3 | OCH3 | |
| 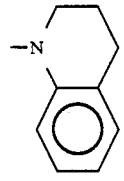 | 3-Cl | 5-Cl | O | OCH3 | C2H5 | |
| 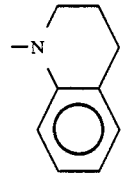 | 5-OCH3 | H | O | OCH3 | OCH3 | |
| 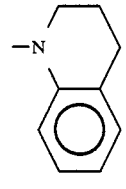 | 5-NO2 | 3-Cl | O | OCH3 | CH2OCH3 | |
| 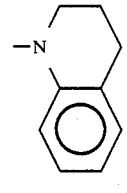 | 5-Cl | H | O | OCH3 | OCH3 | |
| 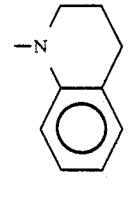 | H | H | O | CH3 | OC2H5 | |
| 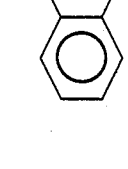 | 5-CN | H | O | CH3 | OCH3 | |
|  | 5-CF3 | H | O | CH3 | OCH3 | |
|  | 5-SO2CH3 | H | O | CH3 | OCH3 | |
| 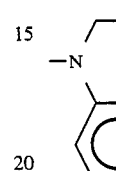 | H | H | O | CH3 | CH3 | |
| H NOCH3 | H | H | O | CH3 | CH3 | |
| H NOCH3 | 5-Cl | H | O | CH3 | CH3 | |
| H NOCH3 | 4-NO2 | H | O | OCH3 | OCH3 | |
| H NOCH3 | 5-SO2CH3 | H | O | OCH3 | OCH3 | |
| H NOCH3 | 5-OCH3 | H | O | OCH3 | CH3 | |
| H NOCH3 | 5-Cl | 4-Cl | O | OCH3 | CH3 | |
| H NOC2H5 | H | H | O | OCH3 | OCH3 | |
| H NOC2H5 | 5-CN | H | O | CH3 | CH3 | |
| H NOC2H5 | 5-Cl | H | O | CH3 | OCH3 | |
| H NOC2H5 | 5-NH2 | H | O | CH3 | OCH2CO2CH3 | |
| H NOC2H5 | 5-CH3 | H | O | CH3 | CH3 | |
| H NOC2H5 | 5-SO2CH3 | H | O | OCH3 | OCH3 | |

TABLE III-continued

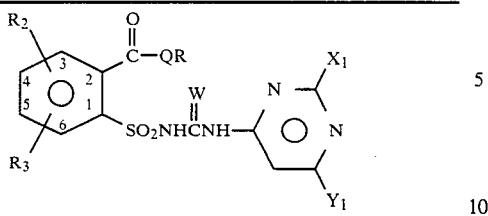

| QR | R2 | R3 | W | X1 | Y1 | m.p. (°C.) |
|---|---|---|---|---|---|---|
| H NOC2H5 | 5-NH2 | H | O | OCH3 | CH2CO2C2H5 | |

TABLE IV

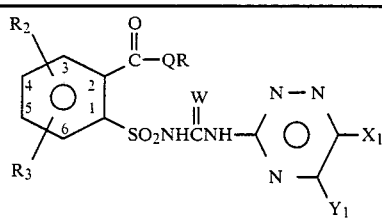

| QR | R2 | R3 | W | X1 | Y1 | m.p. (°C.) |
|---|---|---|---|---|---|---|
| OCH2CHCH2 (epoxide) | H | H | O | OCH3 | CH3 | |
| OCH2CHCH2 | H | H | O | CH3 | OCH3 | |
| OCH2CHCH2 | 6-Cl | H | O | OCH3 | OCH3 | |
| OCH2CHCH2 | 3-Cl | 5-Cl | O | OCH3 | C2H5 | |
| OCH2CHCH2 | 5-OCH3 | H | O | OCH3 | OCH3 | |
| OCH2CHCH2 | 5-NO2 | 3-Cl | O | OCH3 | CH2OCH3 | |
| OCH2CHCH2 | 5-Cl | H | O | OCH3 | OCH3 | |
| OCH2CHCH2 | H | H | O | CH3 | OC2H5 | |
| OCH2CHCH2 | 5-CN | H | O | CH3 | OCH3 | |
| OCH2CHCH2 | 5-CF3 | H | O | CH3 | OCH3 | |
| OCH2CHCH2 | 5-SO2CH3 | H | O | CH3 | OCH3 | |
| OCH2CHCH2 | H | H | O | CH3 | CH3 | |

TABLE IV-continued

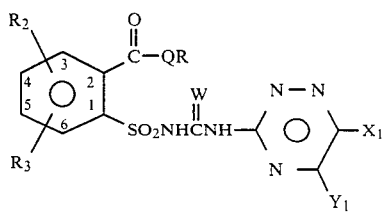

| QR | R2 | R3 | W | X1 | Y1 | m.p. (°C.) |
|---|---|---|---|---|---|---|
| 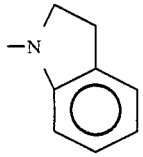 | H | H | O | OCH3 | CH3 | |
| 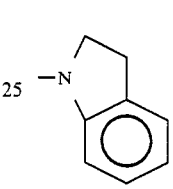 | H | H | O | CH3 | OCH3 | |
| 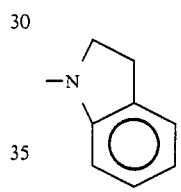 | 6-Cl | H | O | OCH3 | OCH3 | |
| 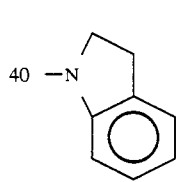 | 3-Cl | 5-Cl | O | OCH3 | C2H5 | |
| 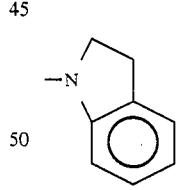 | 5-OCH3 | H | O | OCH3 | OCH3 | |
| 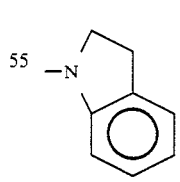 | 5-NO2 | 3-Cl | O | OCH3 | CH2OCH3 | |
| 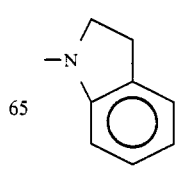 | 5-Cl | H | O | OCH3 | OCH3 | |

TABLE IV-continued

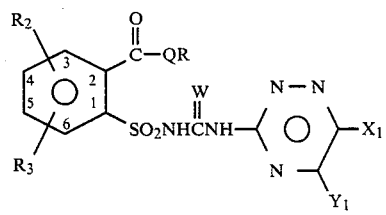

| QR | R2 | R3 | W | X1 | Y1 | m.p. (°C.) |
|---|---|---|---|---|---|---|
| (indoline-N) | H | H | O | CH3 | OC2H5 | |
| (indoline-N) | 5-CN | H | O | CH3 | OCH3 | |
| (indoline-N) | 5-CF3 | H | O | CH3 | OCH3 | |
| (indoline-N) | 5-SO2CH3 | H | O | CH3 | OCH3 | |
| (indoline-N) | H | H | O | CH3 | CH3 | |
| (tetrahydroquinoline-N) | H | H | O | OCH3 | CH3 | |
| (tetrahydroquinoline-N) | H | H | O | CH3 | OCH3 | |

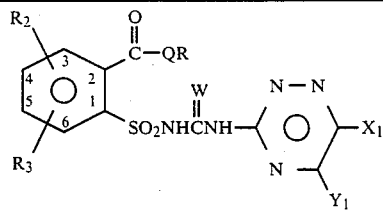

| QR | R2 | R3 | W | X1 | Y1 | m.p. (°C.) |
|---|---|---|---|---|---|---|
| (tetrahydroquinoline-N) | 6-Cl | H | O | OCH3 | OCH3 | |
| (tetrahydroquinoline-N) | 3-Cl | 5-Cl | O | OCH3 | C2H5 | |
| (tetrahydroquinoline-N) | 5-OCH3 | H | O | OCH3 | OCH3 | |
| (tetrahydroquinoline-N) | 5-NO2 | 3-Cl | O | OCH3 | CH2OCH3 | |
| (tetrahydroquinoline-N) | 5-Cl | H | O | OCH3 | OCH3 | |
| (tetrahydroquinoline-N) | H | H | O | CH3 | OC2H5 | |
| (tetrahydroquinoline-N) | 5-CN | H | O | CH3 | OCH3 | |

TABLE IV-continued

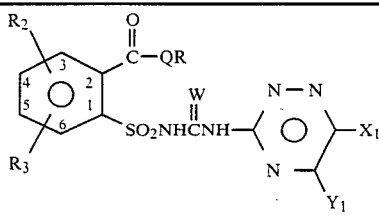

| QR | R2 | R3 | W | X1 | Y1 | m.p. (°C.) |
|---|---|---|---|---|---|---|
|  | 5-CF3 | H | O | CH3 | OCH3 | |
|  | 5-SO2CH3 | H | O | CH3 | OCH3 | |

TABLE IV-continued

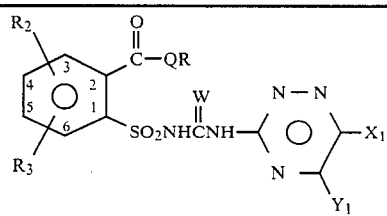

| QR | R2 | R3 | W | X1 | Y1 | m.p. (°C.) |
|---|---|---|---|---|---|---|
|  | H | H | O | CH3 | CH3 | |
| H −NOCH3 | H | H | O | CH3 | CH3 | |
| H −NOCH3 | 5-Cl | H | O | CH3 | OCH3 | |
| H −NOCH3 | 5-CF3 | H | O | CH3 | OCH3 | |
| H −NOCH3 | 4-Cl | 5-Cl | O | OCH3 | OCH3 | |

TABLE V

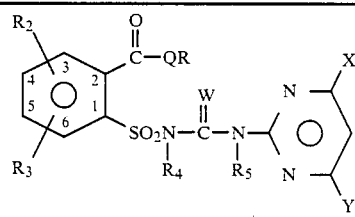

| R2 | QR | R3 | R4 | R5 | W | X | Y | m.p. (°C.) |
|---|---|---|---|---|---|---|---|---|
| 5-NCO | OCH3 | H | H | H | O | CH3 | CH3 | |
| 5-NCO | OCH3 | H | H | H | O | CH3 | OCH3 | |
| 5-NCO | OCH3 | H | H | H | O | OCH3 | OCH3 | |
| 5-NCO | OCH3 | H | H | H | O | CH3 | OCH2CH3 | |
| 5-NCO | OCH3 | H | H | H | O | CH3 | CH2OCH3 | |
| 5-NCO | OCH3 | H | H | H | O | CH3 | OCH2CO2CH3 | |
| 5-NCO | OCH3 | H | H | H | O | CH3 | SCHCO2CH3 \| CH3 | |
| 5-NCO | OCH3 | H | H | H | O | CH3 | OCH2CH2OCH3 | |
| 5-NCO | OCH3 | H | H | H | O | CH3 | SCH3 | |
| 5-NCO | OCH3 | H | H | H | O | CH3 | SCH2CH2SCH3 | |
| 5-NCO | OCH3 | H | H | H | O | CH3 | SCH2CH=CH2 | |
| 5-NCO | OCH3 | H | H | H | O | CH3 | n-C4H9 | |
| 5-NCO | OCH3 | H | H | H | O | CH3 | CH2CH2CN | |
| 5-NCO | OCH3 | H | H | H | O | CH3 | CH2C≡CCH3 | |
| 5-NCO | OCH3 | H | H | H | O | CH3 | OCH2CH=CH2 | |
| 5-NCO | OCH3 | H | H | H | O | CH3 | 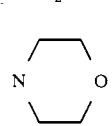 | |
| 5-NCO | OCH3 | H | H | H | O | CH3 | O(CH2)3CH3 | |
| 5-NCO | OCH3 | H | H | H | O | CH3 | OCH2CH2Br | |
| 5-NCO | OCH3 | H | H | H | O | CH3 | OCH2CCl3 | |
| 5-NCO | OCH3 | H | H | H | O | CH3 | CF3 | |
| 5-NCO | OCH3 | H | H | H | O | OCH2CH3 | OCH2CH3 | |

TABLE V-continued $$\text{structure with } R_2, R_3 \text{ on benzene ring, C(=O)-OR at position 2, SO}_2\text{N(R}_4\text{)-C(=W)-N(R}_5\text{)-pyrimidine with X and Y substituents}$$

| R₂ | QR | R₃ | R₄ | R₅ | W | X | Y | m.p. (°C.) |
|---|---|---|---|---|---|---|---|---|
| 5-NCO | OCH₃ | H | H | CH₃ | O | CH₃ | OCH₃ | |
| 5-NCO | OCH₃ | H | CH₃ | H | O | CH₃ | OCH₃ | |
| 5-NCO | OCH₃ | 6-Cl | H | H | O | CH₃ | OCH₃ | |
| 5-NCO | OCH₃ | 3-F | H | H | O | CH₃ | OCH₃ | |
| 5-NCO | OCH₃ | 6-CH₃ | H | H | O | CH₃ | OCH₃ | |
| 5-NCO | OCH₃ | H | H | H | O | CH₂OCH₃ | OCH₃ | |
| 5-NCO | OCH₃ | H | H | H | O | CH₂OCH₂CH₃ | OCH₃ | |
| 5-CH₃NHC(O)NH— | OCH₃ | H | H | H | O | CH₃ | CH₃ | 195–198° |
| 5-CH₃NHC(O)NH— | OCH₃ | H | H | H | O | CH₃ | OCH₃ | 184–187° |
| 5-CH₃NHC(O)NH— | OCH₃ | H | H | H | O | OCH₃ | OCH₃ | 153–158° |
| 5-CH₃NHC(O)NH— | OCH₃ | H | H | H | O | CH₃ | OCH₂CH₃ | |
| 5-CH₃NHC(O)NH— | OCH₃ | H | H | H | O | CH₃ | CH₂OCH₃ | |
| 5-CH₃NHC(O)NH— | OCH₃ | H | H | H | O | CH₃ | OCH₂CO₂CH₃ | |
| 5-CH₃NHC(O)NH— | OCH₃ | H | H | H | O | CH₃ | SCH(CH₃)CO₂CH₃ | |
| 5-CH₃NHC(O)NH— | OCH₃ | H | H | H | O | CH₃ | OCH₂CH₂OCH₃ | |
| 5-CH₃NHC(O)NH— | OCH₃ | H | H | H | O | CH₃ | SCH₃ | |
| 5-CH₃NHC(O)NH— | OCH₃ | H | H | H | O | CH₃ | SCH₂CH₂SCH₃ | |
| 5-CH₃NHC(O)NH— | OCH₃ | H | H | H | O | CH₃ | SCH₂CH=CH₂ | |
| 5-CH₃NHC(O)NH— | OCH₃ | H | H | H | O | CH₃ | OCH₂C(O)N(CH₃)₂ | |
| 5-CH₃NHC(O)NH— | OCH₃ | H | H | H | O | CH₃ | n-C₄H₉ | |
| 5-CH₃NHC(O)NH— | OCH₃ | H | H | H | O | CH₃ | CH₂CH₂CN | |
| 5-CH₃NHC(O)NH— | OCH₃ | H | H | H | O | CH₃ | CH₂C≡CCH₃ | |
| 5-CH₃NHC(O)NH— | OCH₃ | H | H | H | O | CH₃ | OCH₂CH=CH₂ | |

TABLE V-continued

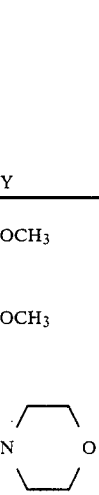

| R2 | QR | R3 | R4 | R5 | W | X | Y | m.p. (°C.) |
|---|---|---|---|---|---|---|---|---|
| 5-CH₃NHC(O)NH— | OCH₃ | H | H | H | O | CH₂OCH₃ | OCH₃ | |
| 5-CH₃NHC(O)NH— | OCH₃ | H | H | H | O | CH₂OCH₂CH₃ | OCH₃ | |
| 5-CH₃NHC(O)NH— | OCH₃ | H | H | H | O | CH₃ | morpholino (N–O ring) | |
| 5-CH₃NHC(O)NH— | OCH₃ | H | H | H | O | CH₃ | O(CH₂)₃CH₃ | |
| 5-CH₃NHC(O)NH— | OCH₃ | H | H | H | O | CH₃ | OCH₂CH₂Br | |
| 5-CH₃NHC(O)NH— | OCH₃ | H | H | H | O | CH₃ | OCH₂CCl₃ | |
| 5-CH₃NHC(O)NH— | OCH₃ | H | H | H | O | CH₃ | CF₃ | |
| 5-CH₃NHC(O)NH— | OCH₃ | H | H | H | O | OCH₂CH₃ | OCH₂CH₃ | |
| 5-CH₃NHC(O)NH— | OCH₃ | H | H | H | S | CH₃ | OCH₃ | |
| 5-CH₃NHC(O)NH— | OCH₃ | H | H | H | S | OCH₃ | OCH₃ | |
| 5-CH₃NHC(O)NH— | OCH₃ | H | H | CH₃ | O | CH₃ | OCH₃ | |
| 5-CH₃NHC(O)NH— | OCH₃ | H | CH₃ | H | O | CH₃ | OCH₃ | |
| 5-CH₃NHC(O)NH— | OCH₃ | 6-Cl | H | H | O | CH₃ | OCH₃ | |
| 5-CH₃NHC(O)NH— | OCH₃ | 3-F | H | H | O | CH₃ | OCH₃ | |
| 5-CH₃NHC(O)NH— | OCH₃ | 6-CH₃ | H | H | O | CH₃ | OCH₃ | |
| (CH₃)₃CNHC(O)NH— | OCH₃ | H | H | H | O | CH₃ | OCH₃ | 137–140° |
| (CH₃)₃CNHC(O)NH— | OCH₃ | H | H | H | O | OCH₃ | OCH₃ | 186–188° |

TABLE V-continued

Structure: benzene ring with R2 (pos 3), R3 (pos 5), C(=O)-QR (pos 2), and SO2N(R4)-C(=W)-N(R5)-[pyrimidine with X, Y] at pos 1.

| R2 | QR | R3 | R4 | R5 | W | X | Y | m.p. (°C.) |
|---|---|---|---|---|---|---|---|---|
| ClCH₂CH₂—NH—C(=O)—NH— | OCH₃ | H | H | H | O | OCH₃ | OCH₃ | 73–78° |
| 5-CH₃C(=O)NH— | OCH₃ | H | H | H | O | CH₃ | CH₃ | |
| 5-CH₃C(=O)NH— | OCH₃ | H | H | H | O | CH₃ | OCH₃ | |
| 5-CH₃C(=O)NH— | OCH₃ | H | H | H | O | OCH₃ | OCH₃ | 95–105° |
| 5-CH₃C(=O)NH— | OCH₃ | H | H | H | O | CH₃ | OCH₂CH₃ | |
| 5-CH₃C(=O)NH— | OCH₃ | H | H | H | O | CH₃ | CH₂OCH₃ | |
| 5-CH₃C(=O)NH— | OCH₃ | H | H | H | O | CH₃ | OCH₂CO₂CH₃ | |
| 5-CH₃C(=O)NH— | OCH₃ | H | H | H | O | CH₃ | SCH(CH₃)CO₂CH₃ | |
| 5-CH₃C(=O)NH— | OCH₃ | H | H | H | O | CH₃ | OCH₂CH₂OCH₃ | |
| 5-CH₃C(=O)NH— | OCH₃ | H | H | H | O | CH₃ | SCH₃ | |
| 5-CH₃C(=O)NH— | OCH₃ | H | H | H | O | CH₃ | SCH₂CH₂SCH₃ | |
| 5-CH₃C(=O)NH— | OCH₃ | H | H | H | O | CH₃ | SCH₂CH=CH₂ | |
| 5-CH₃C(=O)NH— | OCH₃ | H | H | H | O | CH₃ | OCH₂C(=O)N(CH₃)₂ | |
| 5-CH₃C(=O)NH— | OCH₃ | H | H | H | O | CH₃ | n-C₄H₉ | |
| 5-CH₃C(=O)NH— | OCH₃ | H | H | H | O | CH₃ | CH₂CH₂CN | |
| 5-CH₃C(=O)NH— | OCH₃ | H | H | H | O | CH₃ | CH₂C≡CCH₃ | |
| 5-CH₃C(=O)NH— | OCH₃ | H | H | H | O | CH₃ | OCH₂CH=CH₂ | |
| 5-CH₃C(=O)NH— | OCH₃ | H | H | H | O | CH₂OCH₃ | OCH₃ | |

TABLE V-continued

| R2 | QR | R3 | R4 | R5 | W | X | Y | m.p. (°C.) |
|---|---|---|---|---|---|---|---|---|
| 5-CH$_3$C(O)NH— | OCH$_3$ | H | H | H | O | CH$_2$OCH$_2$CH$_3$ | OCH$_3$ | |
| 5-CH$_3$C(O)NH— | OCH$_3$ | H | H | H | O | CH$_3$ | morpholino (N-O ring) | |
| 5-CH$_3$C(O)NH— | OCH$_3$ | H | H | H | O | CH$_3$ | O(CH$_2$)$_3$CH$_3$ | |
| 5-CH$_3$C(O)NH— | OCH$_3$ | H | H | H | O | CH$_3$ | OCH$_2$CH$_2$Br | |
| 5-CH$_3$C(O)NH— | OCH$_3$ | H | H | H | O | CH$_3$ | OCH$_2$CCl$_3$ | |
| 5-CH$_3$C(O)NH— | OCH$_3$ | H | H | H | O | CH$_3$ | CF$_3$ | |
| 5-CH$_3$C(O)NH— | OCH$_3$ | H | H | H | O | OCH$_2$CH$_3$ | OCH$_2$CH$_3$ | |
| 5-CH$_3$C(O)NH— | OCH$_3$ | H | H | H | S | CH$_3$ | OCH$_3$ | |
| 5-CH$_3$C(O)NH— | OCH$_3$ | H | H | H | S | OCH$_3$ | OCH$_3$ | |
| 5-CH$_3$C(O)NH— | OCH$_3$ | H | H | CH$_3$ | O | CH$_3$ | OCH$_3$ | |
| 5-CH$_3$C(O)NH— | OCH$_3$ | H | CH$_3$ | H | O | CH$_3$ | OCH$_3$ | |
| 5-CH$_3$C(O)NH— | OCH$_3$ | 6-Cl | H | H | O | CH$_3$ | OCH$_3$ | |
| 5-CH$_3$C(O)NH— | OCH$_3$ | 3-F | H | H | O | CH$_3$ | OCH$_3$ | |
| 5-CH$_3$C(O)NH— | OCH$_3$ | 6-CH$_3$ | H | H | O | CH$_3$ | OCH$_3$ | |
| 5-CH$_3$SC(O)NH— | OCH$_3$ | H | H | H | O | CH$_3$ | CH$_3$ | |
| 5-CH$_3$SC(O)NH— | OCH$_3$ | H | H | H | O | CH$_3$ | OCH$_3$ | |
| 5-CH$_3$SC(O)NH— | OCH$_3$ | H | H | H | O | OCH$_3$ | OCH$_3$ | |

TABLE V-continued

Structure: benzene ring with positions 1-6; R2 at position 3, R3 at position 5; position 2 bears C(=O)-QR; position 1 bears SO2N(R4)-C(=W)-N(R5)-pyrimidine substituted with X and Y.

| R2 | QR | R3 | R4 | R5 | W | X | Y | m.p. (°C.) |
|---|---|---|---|---|---|---|---|---|
| 5-CH3SC(O)NH— | OCH3 | H | H | H | O | CH3 | OCH2CH3 | |
| 5-CH3SC(O)NH— | OCH3 | H | H | H | O | CH3 | CH2OCH3 | |
| 5-CH3SC(O)NH— | OCH3 | H | H | H | O | CH3 | OCH2CO2CH3 | |
| 5-CH3SC(O)NH— | OCH3 | H | H | H | O | CH3 | SCH(CH3)CO2CH3 | |
| 5-CH3SC(O)NH— | OCH3 | H | H | H | O | CH3 | OCH2CH2OCH3 | |
| 5-CH3SC(O)NH— | OCH3 | H | H | H | O | CH3 | SCH3 | |
| 5-CH3SC(O)NH— | OCH3 | H | H | H | O | CH3 | SCH2CH2SCH3 | |
| 5-CH3SC(O)NH— | OCH3 | H | H | H | O | CH3 | SCH2CH=CH2 | |
| 5-CH3SC(O)NH— | OCH3 | H | H | H | O | CH3 | OCH2C(O)N(CH3)2 | |
| 5-CH3SC(O)NH— | OCH3 | H | H | H | O | CH3 | n-C4H9 | |
| 5-CH3SC(O)NH— | OCH3 | H | H | H | O | CH3 | CH2CH2CN | |
| 5-CH3SC(O)NH— | OCH3 | H | H | H | O | CH3 | CH2C≡CCH3 | |
| 5-CH3SC(O)NH— | OCH3 | H | H | H | O | CH3 | OCH2CH=CH2 | |
| 5-CH3SC(O)NH— | OCH3 | H | H | H | O | CH2OCH3 | OCH3 | |
| 5-CH3SC(O)NH— | OCH3 | H | H | H | O | CH2OCH2CH3 | OCH3 | |
| 5-CH3SC(O)NH— | OCH3 | H | H | H | O | CH3 | morpholino (N-linked, with O) | |
| 5-CH3SC(O)NH— | OCH3 | H | H | H | O | CH3 | O(CH2)3CH3 | |

TABLE V-continued

| R2 | QR | R3 | R4 | R5 | W | X | Y | m.p. (°C.) |
|---|---|---|---|---|---|---|---|---|
| 5-CH$_3$SC(O)NH— | OCH$_3$ | H | H | H | O | CH$_3$ | OCH$_2$CH$_2$Br | |
| 5-CH$_3$SC(O)NH— | OCH$_3$ | H | H | H | O | CH$_3$ | OCH$_2$CCl$_3$ | |
| 5-CH$_3$SC(O)NH— | OCH$_3$ | H | H | H | O | CH$_3$ | CF$_3$ | |
| 5-CH$_3$SC(O)NH— | OCH$_3$ | H | H | H | O | OCH$_2$CH$_3$ | OCH$_2$CH$_3$ | |
| 5-CH$_3$SC(O)NH— | OCH$_3$ | H | H | H | S | CH$_3$ | OCH$_3$ | |
| 5-CH$_3$SC(O)NH— | OCH$_3$ | H | H | H | S | OCH$_3$ | OCH$_3$ | |
| 5-CH$_3$SC(O)NH— | OCH$_3$ | H | H | CH$_3$ | O | CH$_3$ | OCH$_3$ | |
| 5-CH$_3$SC(O)NH— | OCH$_3$ | H | CH$_3$ | H | O | CH$_3$ | OCH$_3$ | |
| 5-CH$_3$SC(O)NH— | OCH$_3$ | 6-Cl | H | H | O | CH$_3$ | OCH$_3$ | |
| 5-CH$_3$SC(O)NH— | OCH$_3$ | 3-F | H | H | O | CH$_3$ | OCH$_3$ | |
| 5-CH$_3$SC(O)NH— | OCH$_3$ | 6-CH$_3$ | H | H | O | CH$_3$ | OCH$_3$ | |
| 5-CH$_3$OC(O)NH— | OCH$_3$ | H | H | H | O | CH$_3$ | CH$_3$ | |
| 5-CH$_3$OC(O)NH— | OCH$_3$ | H | H | H | O | CH$_3$ | OCH$_3$ | |
| 5-CH$_3$OC(O)NH— | OCH$_3$ | H | H | H | O | OCH$_3$ | OCH$_3$ | |
| 5-CH$_3$OC(O)NH— | OCH$_3$ | H | H | H | O | CH$_3$ | OCH$_2$CH$_3$ | |
| 5-CH$_3$OC(O)NH— | OCH$_3$ | H | H | H | O | CH$_3$ | CH$_2$OCH$_3$ | |
| 5-CH$_3$OC(O)NH— | OCH$_3$ | H | H | H | O | CH$_3$ | OCH$_2$CO$_2$CH$_3$ | |
| 5-CH$_3$OC(O)NH— | OCH$_3$ | H | H | H | O | CH$_3$ | SCH(CH$_3$)CO$_2$CH$_3$ | |

TABLE V-continued

| R2 | QR | R3 | R4 | R5 | W | X | Y | m.p. (°C.) |
|---|---|---|---|---|---|---|---|---|
| 5-CH3OCNH— | OCH3 | H | H | H | O | CH3 | OCH2CH2OCH3 | |
| 5-CH3OCNH— | OCH3 | H | H | H | O | CH3 | SCH3 | |
| 5-CH3OCNH— | OCH3 | H | H | H | O | CH3 | SCH2CH2SCH3 | |
| 5-CH3OCNH— | OCH3 | H | H | H | O | CH3 | SCH2CH=CH2 | |
| 5-CH3OCNH— | OCH3 | H | H | H | O | CH3 | OCH2CN(CH3)2 | |
| 5-CH3OCNH— | OCH3 | H | H | H | O | CH3 | n-C4H9 | |
| 5-CH3OCNH— | OCH3 | H | H | H | O | CH3 | CH2CH2CN | |
| 5-CH3OCNH— | OCH3 | H | H | H | O | CH3 | CH2C≡CCH3 | |
| 5-CH3OCNH— | OCH3 | H | H | H | O | CH3 | OCH2CH=CH2 | |
| 5-CH3OCNH— | OCH3 | H | H | H | O | CH2OCH3 | OCH3 | |
| 5-CH3OCNH— | OCH3 | H | H | H | O | CH2OCH2CH3 | OCH3 | |
| 5-CH3OCNH— | OCH3 | H | H | H | O | CH3 | N O (morpholino) | |
| 5-CH3OCNH— | OCH3 | H | H | H | O | CH3 | O(CH2)3CH3 | |
| 5-CH3OCNH— | OCH3 | H | H | H | O | CH3 | OCH2CH2Br | |
| 5-CH3OCNH— | OCH3 | H | H | H | O | CH3 | OCH2CCl3 | |
| 5-CH3OCNH— | OCH3 | H | H | H | O | CH3 | CF3 | |
| 5-CH3OCNH— | OCH3 | H | H | H | O | OCH2CH3 | OCH2CH3 | |

TABLE V-continued

Structure: benzene ring with R2 (positions 3,4,5), R3, C(=O)-QR at position 2, SO2N(R4)-C(W)-N(R5)- linked to pyrimidine with X and Y substituents.

| R2 | QR | R3 | R4 | R5 | W | X | Y | m.p. (°C.) |
|---|---|---|---|---|---|---|---|---|
| 5-CH3OC(O)NH— | OCH3 | H | H | H | S | CH3 | OCH3 | |
| 5-CH3OC(O)NH— | OCH3 | H | H | H | S | OCH3 | OCH3 | |
| 5-CH3OC(O)NH— | OCH3 | H | H | CH3 | O | CH3 | OCH3 | |
| 5-CH3OC(O)NH— | OCH3 | H | CH3 | H | O | CH3 | OCH3 | |
| 5-CH3OC(O)NH— | OCH3 | 6-Cl | H | H | O | CH3 | OCH3 | |
| 5-CH3OC(O)NH— | OCH3 | 3-F | H | H | O | CH3 | OCH3 | |
| 5-CH3OC(O)NH— | OCH3 | 6-CH3 | H | H | O | CH3 | OCH3 | |
| CH3SO2NH— | OCH3 | H | H | H | O | CH3 | CH3 | |
| CH3SO2NH— | OCH3 | H | H | H | O | CH3 | OCH3 | |
| CH3SO2NH— | OCH3 | H | H | H | O | OCH3 | OCH3 | |
| CH3SO2NH— | OCH3 | H | H | H | O | CH3 | OCH2CH3 | |
| CH3SO2NH— | OCH3 | H | H | H | O | CH3 | CH2OCH3 | |
| CH3SO2NH— | OCH3 | H | H | H | O | CH3 | OCH2CO2CH3 | |
| CH3SO2NH— | OCH3 | H | H | H | O | CH3 | SCH(CH3)CO2CH3 | |
| CH3SO2NH— | OCH3 | H | H | H | O | CH3 | OCH2CH2OCH3 | |
| CH3SO2NH— | OCH3 | H | H | H | O | CH3 | SCH3 | |
| CH3SO2NH— | OCH3 | H | H | H | O | CH3 | SCH2CH2SCH3 | |
| CH3SO2NH— | OCH3 | H | H | H | O | CH3 | SCH2CH=CH2 | |
| CH3SO2NH— | OCH3 | H | H | H | O | CH3 | OCH2C(O)N(CH3)2 | |
| CH3SO2NH— | OCH3 | H | H | H | O | CH3 | n-C4H9 | |
| CH3SO2NH— | OCH3 | H | H | H | O | CH3 | CH2CH2CN | |
| CH3SO2NH— | OCH3 | H | H | H | O | CH3 | CH2C≡CCH3 | |
| CH3SO2NH— | OCH3 | H | H | H | O | CH3 | OCH2CH=CH2 | |
| CH3SO2NH— | OCH3 | H | H | H | O | CH3 | morpholino (N-...-O) | |
| CH3SO2NH— | OCH3 | H | H | H | O | CH3 | O(CH2)3CH3 | |
| CH3SO2NH— | OCH3 | H | H | H | O | CH3 | OCH2CH2Br | |
| CH3SO2NH— | OCH3 | H | H | H | O | CH3 | OCH2CCl3 | |
| CH3SO2NH— | OCH3 | H | H | H | O | CH3 | CF3 | |
| CH3SO2NH— | OCH3 | H | H | H | O | OCH2CH3 | OCH2CH3 | |
| CH3SO2NH— | OCH3 | H | H | H | S | CH3 | OCH3 | |
| CH3SO2NH— | OCH3 | H | H | H | S | OCH3 | OCH3 | |
| CH3SO2NH— | OCH3 | H | H | CH3 | O | CH3 | OCH3 | |
| CH3SO2NH— | OCH3 | H | CH3 | H | O | CH3 | OCH3 | |
| CH3SO2NH— | OCH3 | 6-Cl | H | H | O | CH3 | OCH3 | |
| CH3SO2NH— | OCH3 | 3-F | H | H | O | CH3 | OCH3 | |
| CH3SO2NH— | OCH3 | 6-CH3 | H | H | O | CH3 | OCH3 | |

TABLE V-continued

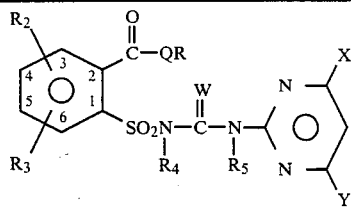

| R₂ | QR | R₃ | R₄ | R₅ | W | X | Y | m.p. (°C.) |
|---|---|---|---|---|---|---|---|---|
| CH₃SO₂NH— | OCH₃ | H | H | H | H | CH₂OCH₃ | OCH₃ | |
| CH₃SO₂NH— | OCH₃ | H | H | H | H | CH₂OCH₂CH₃ | OCH₃ | |
| CF₃SO₂NH— | OCH₃ | H | H | H | O | CH₃ | CH₃ | |
| CF₃SO₂NH— | OCH₃ | H | H | H | O | CH₃ | OCH₃ | |
| CF₃SO₂NH— | OCH₃ | H | H | H | O | OCH₃ | OCH₃ | |
| CF₃SO₂NH— | OCH₃ | H | H | H | O | CH₃ | OCH₂CH₃ | |
| CF₃SO₂NH— | OCH₃ | H | H | H | O | CH₃ | CH₂OCH₃ | |
| CF₃SO₂NH— | OCH₃ | H | H | H | O | CH₃ | OCH₂CO₂CH₃ | |
| CF₃SO₂NH— | OCH₃ | H | H | H | O | CH₃ | SCH(CH₃)CO₂CH₃ | |
| CF₃SO₂NH— | OCH₃ | H | H | H | O | CH₃ | OCH₂CH₂OCH₃ | |
| CF₃SO₂NH— | OCH₃ | H | H | H | O | CH₃ | SCH₃ | |
| CF₃SO₂NH— | OCH₃ | H | H | H | O | CH₃ | SCH₂CH₂SCH₃ | |
| CF₃SO₂NH— | OCH₃ | H | H | H | O | CH₃ | SCH₂CH=CH₂ | |
| CF₃SO₂NH— | OCH₃ | H | H | H | O | CH₃ | OCH₂C(O)N(CH₃)₂ | |
| CF₃SO₂NH— | OCH₃ | H | H | H | O | CH₃ | n-C₄H₉ | |
| CF₃SO₂NH— | OCH₃ | H | H | H | O | CH₃ | CH₂CH₂CN | |
| CF₃SO₂NH— | OCH₃ | H | H | H | O | CH₃ | CH₂C≡CCH₃ | |
| CF₃SO₂NH— | OCH₃ | H | H | H | O | CH₃ | OCH₂CH=CH₂ | |
| CF₃SO₂NH— | OCH₃ | H | H | H | O | CH₃ | morpholino (N-O ring) | |
| CF₃SO₂NH— | OCH₃ | H | H | H | O | CH₃ | O(CH₂)₃CH₃ | |
| CF₃SO₂NH— | OCH₃ | H | H | H | O | CH₃ | OCH₂CH₂Br | |
| CF₃SO₂NH— | OCH₃ | H | H | H | O | CH₃ | OCH₂CCl₃ | |
| CF₃SO₂NH— | OCH₃ | H | H | H | O | CH₃ | CF₃ | |
| CF₃SO₂NH— | OCH₃ | H | H | H | O | OCH₂CH₃ | OCH₂CH₃ | |
| CF₃SO₂NH— | OCH₃ | H | H | H | S | CH₃ | OCH₃ | |
| CF₃SO₂NH— | OCH₃ | H | H | H | S | OCH₃ | OCH₃ | |
| CF₃SO₂NH— | OCH₃ | H | H | CH₃ | O | CH₃ | OCH₃ | |
| CF₃SO₂NH— | OCH₃ | H | CH₃ | H | O | CH₃ | OCH₃ | |
| CF₃SO₂NH— | OCH₃ | 6-Cl | H | H | O | CH₃ | OCH₃ | |
| CF₃SO₂NH— | OCH₃ | 3-F | H | H | O | CH₃ | OCH₃ | |
| CF₃SO₂NH— | OCH₃ | 6-CH₃ | H | H | O | CH₃ | OCH₃ | |
| CF₃SO₂NH— | OCH₃ | H | H | H | O | CH₂OCH₃ | OCH₃ | |
| CF₃SO₂NH— | OCH₃ | H | H | H | O | CH₂OCH₂CH₃ | OCH₃ | |

TABLE VI

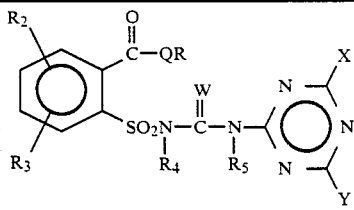

| R₂ | QR | R₃ | R₄ | R₅ | W | X | Y | m.p. (°C.) |
|---|---|---|---|---|---|---|---|---|
| 5-NCO | OCH₃ | H | H | H | O | CH₃ | CH₃ | |
| 5-NCO | OCH₃ | H | H | H | O | CH₃ | OCH₃ | |
| 5-NCO | OCH₃ | H | H | H | O | OCH₃ | OCH₃ | |
| 5-NCO | OCH₃ | H | H | H | O | CH₃ | OCH₂CH₃ | |
| 5-NCO | OCH₃ | H | H | H | O | CH₃ | CH₂OCH₃ | |
| 5-NCO | OCH₃ | H | H | H | O | CH₃ | OCH₂CO₂CH₃ | |

TABLE VI-continued

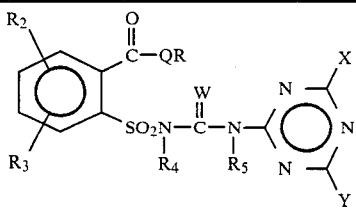

| R<sub>2</sub> | QR | R<sub>3</sub> | R<sub>4</sub> | R<sub>5</sub> | W | X | Y | m.p. (°C.) |
|---|---|---|---|---|---|---|---|---|
| 5-NCO | OCH$_3$ | H | H | H | O | CH$_3$ | SCHCO$_2$CH$_3$<br>\|<br>CH$_3$ | |
| 5-NCO | OCH$_3$ | H | H | H | O | CH$_3$ | OCH$_2$CH$_2$OCH$_3$ | |
| 5-NCO | OCH$_3$ | H | H | H | O | CH$_3$ | SCH$_3$ | |
| 5-NCO | OCH$_3$ | H | H | H | O | CH$_3$ | SCH$_2$CH$_2$SCH$_3$ | |
| 5-NCO | OCH$_3$ | H | H | H | O | CH$_3$ | SCH$_2$CH=CH$_2$ | |
| 5-NCO | OCH$_3$ | H | H | H | O | CH$_3$ | n-C$_4$H$_9$ | |
| 5-NCO | OCH$_3$ | H | H | H | O | CH$_3$ | CH$_2$CH$_2$CN | |
| 5-NCO | OCH$_3$ | H | H | H | O | CH$_3$ | CH$_2$C≡CCH$_3$ | |
| 5-NCO | OCH$_3$ | H | H | H | O | CH$_3$ | OCH$_2$CH$_2$CH:- | |
| 5-NCO | OCH$_3$ | H | H | H | O | CH$_3$ | —N(CH$_2$CH$_2$)$_2$O (morpholino) | |
| 5-NCO | OCH$_3$ | H | H | H | O | CH$_3$ | O(CH$_2$)$_3$CH$_3$ | |
| 5-NCO | OCH$_3$ | H | H | H | O | CH$_3$ | OCH$_2$CH$_2$Br | |
| 5-NCO | OCH$_3$ | H | H | H | O | CH$_3$ | OCH$_2$CCl$_3$ | |
| 5-NCO | OCH$_3$ | H | H | H | O | CH$_3$ | CF$_3$ | |
| 5-NCO | OCH$_3$ | H | H | H | O | OCH$_2$CH$_3$ | OCH$_2$CH$_3$ | |
| 5-NCO | OCH$_3$ | H | H | CH$_3$ | O | CH$_3$ | OCH$_3$ | |
| 5-NCO | OCH$_3$ | H | CH$_3$ | H | O | CH$_3$ | OCH$_3$ | |
| 5-NCO | OCH$_3$ | 6-Cl | H | H | O | CH$_3$ | OCH$_3$ | |
| 5-NCO | OCH$_3$ | 3-F | H | H | O | CH$_3$ | OCH$_3$ | |
| 5-NCO | OCH$_3$ | 6-CH$_3$ | H | H | O | CH$_3$ | OCH$_3$ | |
| 5-NCO | OCH$_3$ | H | H | H | O | CH$_2$OCH$_3$ | OCH$_3$ | |
| 5-NCO | OCH$_3$ | H | H | H | O | CH$_2$OCH$_2$CH$_3$ | OCH$_3$ | |
| 5-CH$_3$NHC(O)NH— | OCH$_3$ | H | H | H | O | CH$_3$ | CH$_3$ | |
| 5-CH$_3$NHC(O)NH— | OCH$_3$ | H | H | H | O | CH$_3$ | OCH$_3$ | 172–175° |
| 5-CH$_3$NHC(O)NH— | OCH$_3$ | H | H | H | O | OCH$_3$ | OCH$_3$ | |
| 5-CH$_3$NHC(O)NH— | OCH$_3$ | H | H | H | O | CH$_3$ | OCH$_2$CH$_3$ | |
| 5-CH$_3$NHC(O)NH— | OCH$_3$ | H | H | H | O | CH$_3$ | CH$_2$OCH$_3$ | |
| 5-CH$_3$NHC(O)NH— | OCH$_3$ | H | H | H | O | CH$_3$ | OCH$_2$CO$_2$CH$_3$ | |
| 5-CH$_3$NHC(O)NH— | OCH$_3$ | H | H | H | O | CH$_3$ | SCHCO$_2$CH$_3$<br>\|<br>CH$_3$ | |
| 5-CH$_3$NHC(O)NH— | OCH$_3$ | H | H | H | O | CH$_3$ | OCH$_2$CH$_2$OCH$_3$ | |
| 5-CH$_3$NHC(O)NH— | OCH$_3$ | H | H | H | O | CH$_3$ | SCH$_3$ | |

TABLE VI-continued

| R2 | QR | R3 | R4 | R5 | W | X | Y | m.p. (°C.) |
|---|---|---|---|---|---|---|---|---|
| 5-CH3NHC(O)NH— | OCH3 | H | H | H | O | CH3 | SCH2CH2SCH3 | |
| 5-CH3NHC(O)NH— | OCH3 | H | H | H | O | CH3 | SCH2CH=CH2 | |
| 5-CH3NHC(O)NH— | OCH3 | H | H | H | O | CH3 | OCH2C(O)N(CH3)2 | |
| 5-CH3NHC(O)NH— | OCH3 | H | H | H | O | CH3 | n-C4H9 | |
| 5-CH3NHC(O)NH— | OCH3 | H | H | H | O | CH3 | CH2CH2CN | |
| 5-CH3NHC(O)NH— | OCH3 | H | H | H | O | CH3 | CH2C≡CCH3 | |
| 5-CH3NHC(O)NH— | OCH3 | H | H | H | O | CH3 | OCH2CH=CH2 | |
| 5-CH3NHC(O)NH— | OCH3 | H | H | H | O | CH2OCH3 | OCH3 | |
| 5-CH3NHC(O)NH— | OCH3 | H | H | H | O | CH2OCH2CH3 | OCH3 | |
| 5-CH3NHC(O)NH— | OCH3 | H | H | H | O | CH3 | morpholino (N–O ring) | |
| 5-CH3NHC(O)NH— | OCH3 | H | H | H | O | CH3 | O(CH2)3CH3 | |
| 5-CH3NHC(O)NH— | OCH3 | H | H | H | O | CH3 | OCH2CH2Br | |
| 5-CH3NHC(O)NH— | OCH3 | H | H | H | O | CH3 | OCH2CCl3 | |
| 5-CH3NHC(O)NH— | OCH3 | H | H | H | O | CH3 | CF3 | |
| 5-CH3NHC(O)NH— | OCH3 | H | H | H | O | OCH2CH3 | OCH2CH3 | |
| 5-CH3NHC(O)NH— | OCH3 | H | H | H | S | CH3 | OCH3 | |
| 5-CH3NHC(O)NH— | OCH3 | H | H | H | S | OCH3 | OCH3 | |

TABLE VI-continued

[Structure: benzene ring with R2, R3 substituents, C(=O)-OR group, SO2N(R4)-C(=W)-N(R5)- linker to triazine ring with X and Y substituents]

| R2 | QR | R3 | R4 | R5 | W | X | Y | m.p. (°C.) |
|---|---|---|---|---|---|---|---|---|
| 5-CH₃NHC(O)NH— | OCH₃ | H | H | CH₃ | O | CH₃ | OCH₃ | |
| 5-CH₃NHC(O)NH— | OCH₃ | H | CH₃ | H | O | CH₃ | OCH₃ | |
| 5-CH₃NHC(O)NH— | OCH₃ | 6-Cl | H | H | O | CH₃ | OCH₃ | |
| 5-CH₃NHC(O)NH— | OCH₃ | 3-F | H | H | O | CH₃ | OCH₃ | |
| 5-CH₃NHC(O)NH— | OCH₃ | 6-CH₃ | H | H | O | CH₃ | OCH₃ | |
| (CH₃)₃CNHC(O)NH— | OCH₃ | H | H | H | O | CH₃ | OCH₃ | |
| (CH₃)₃CNHC(O)NH— | OCH₃ | H | H | H | O | CH₃ | OCH₃ | |
| 5-CH₃C(O)NH— | OCH₃ | H | H | H | O | CH₃ | CH₃ | |
| 5-CH₃C(O)NH— | OCH₃ | H | H | H | O | CH₃ | OCH₃ | |
| 5-CH₃C(O)NH— | OCH₃ | H | H | H | O | OCH₃ | OCH₃ | |
| 5-CH₃C(O)NH— | OCH₃ | H | H | H | O | CH₃ | OCH₂CH₃ | |
| 5-CH₃C(O)NH— | OCH₃ | H | H | H | O | CH₃ | CH₂OCH₃ | |
| 5-CH₃C(O)NH— | OCH₃ | H | H | H | O | CH₃ | OCH₂CO₂CH₃ | |
| 5-CH₃C(O)NH— | OCH₃ | H | H | H | O | CH₃ | SCH(CH₃)CO₂CH₃ | |
| 5-CH₃C(O)NH— | OCH₃ | H | H | H | O | CH₃ | OCH₂CH₂OCH₃ | |
| 5-CH₃C(O)NH— | OCH₃ | H | H | H | O | CH₃ | SCH₃ | |
| 5-CH₃C(O)NH— | OCH₃ | H | H | H | O | CH₃ | SCH₂CH₂SCH₃ | |
| 5-CH₃C(O)NH— | OCH₃ | H | H | H | O | CH₃ | SCH₂CH=CH₂ | |

TABLE VI-continued

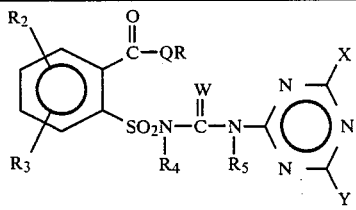

| R2 | QR | R3 | R4 | R5 | W | X | Y | m.p. (°C.) |
|---|---|---|---|---|---|---|---|---|
| 5-CH$_3$C(O)NH— | OCH$_3$ | H | H | H | O | CH$_3$ | OCH$_2$C(O)N(CH$_3$)$_2$ | |
| 5-CH$_3$C(O)NH— | OCH$_3$ | H | H | H | O | CH$_3$ | n-C$_4$H$_9$ | |
| 5-CH$_3$C(O)NH— | OCH$_3$ | H | H | H | O | CH$_3$ | CH$_2$CH$_2$CN | |
| 5-CH$_3$C(O)NH— | OCH$_3$ | H | H | H | O | CH$_3$ | CH$_2$C≡CCH$_3$ | |
| 5-CH$_3$C(O)NH— | OCH$_3$ | H | H | H | O | CH$_3$ | OCH$_2$CH=CH$_2$ | |
| 5-CH$_3$C(O)NH— | OCH$_3$ | H | H | H | O | CH$_2$OCH$_3$ | OCH$_3$ | |
| 5-CH$_3$C(O)NH— | OCH$_3$ | H | H | H | O | CH$_2$OCH$_2$CH$_3$ | OCH$_3$ | |
| 5-CH$_3$C(O)NH— | OCH$_3$ | H | H | H | O | CH$_3$ | morpholino | |
| 5-CH$_3$C(O)NH— | OCH$_3$ | H | H | H | O | CH$_3$ | O(CH$_2$)$_3$CH$_3$ | |
| 5-CH$_3$C(O)NH— | OCH$_3$ | H | H | H | O | CH$_3$ | OCH$_2$CH$_2$Br | |
| 5-CH$_3$C(O)NH— | OCH$_3$ | H | H | H | O | CH$_3$ | OCH$_2$CCl$_3$ | |
| 5-CH$_3$C(O)NH— | OCH$_3$ | H | H | H | O | CH$_3$ | CF$_3$ | |
| 5-CH$_3$C(O)NH— | OCH$_3$ | H | H | H | O | OCH$_2$CH$_3$ | OCH$_2$CH$_3$ | |
| 5-CH$_3$C(O)NH— | OCH$_3$ | H | H | H | S | CH$_3$ | OCH$_3$ | |
| 5-CH$_3$C(O)NH— | OCH$_3$ | H | H | H | S | OCH$_3$ | OCH$_3$ | |
| 5-CH$_3$C(O)NH— | OCH$_3$ | H | H | CH$_3$ | O | CH$_3$ | OCH$_3$ | |
| 5-CH$_3$C(O)NH— | OCH$_3$ | H | CH$_3$ | H | O | CH$_3$ | OCH$_3$ | |

TABLE VI-continued

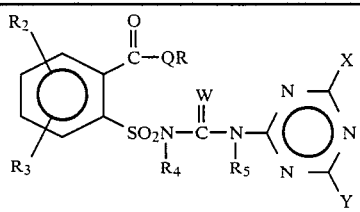

| R₂ | QR | R₃ | R₄ | R₅ | W | X | Y | m.p. (°C.) |
|---|---|---|---|---|---|---|---|---|
| 5-CH₃C(O)NH— | OCH₃ | 6-Cl | H | H | O | CH₃ | OCH₃ | |
| 5-CH₃C(O)NH— | OCH₃ | 3-F | H | H | O | CH₃ | OCH₃ | |
| 5-CH₃C(O)NH— | OCH₃ | 6-CH₃ | H | H | O | CH₃ | OCH₃ | |
| 5-CH₃SC(O)NH— | OCH₃ | H | H | H | O | CH₃ | CH₃ | |
| 5-CH₃SC(O)NH— | OCH₃ | H | H | H | O | CH₃ | OCH₃ | |
| 5-CH₃SC(O)NH— | OCH₃ | H | H | H | O | OCH₃ | OCH₃ | |
| 5-CH₃SC(O)NH— | OCH₃ | H | H | H | O | CH₃ | OCH₂CH₃ | |
| 5-CH₃SC(O)NH— | OCH₃ | H | H | H | O | CH₃ | CH₂OCH₃ | |
| 5-CH₃SC(O)NH— | OCH₃ | H | H | H | O | CH₃ | OCH₂CO₂CH₃ | |
| 5-CH₃SC(O)NH— | OCH₃ | H | H | H | O | CH₃ | SCH(CH₃)CO₂CH₃ | |
| 5-CH₃SC(O)NH— | OCH₃ | H | H | H | O | CH₃ | OCH₂CH₂OCH₃ | |
| 5-CH₃SC(O)NH— | OCH₃ | H | H | H | O | CH₃ | SCH₃ | |
| 5-CH₃SC(O)NH— | OCH₃ | H | H | H | O | CH₃ | SCH₂CH₂SCH₃ | |
| 5-CH₃SC(O)NH— | OCH₃ | H | H | H | O | CH₃ | SCH₂CH=CH₂ | |
| 5-CH₃SC(O)NH— | OCH₃ | H | H | H | O | CH₃ | OCH₂C(O)N(CH₃)₂ | |
| 5-CH₃SC(O)NH— | OCH₃ | H | H | H | O | CH₃ | n-C₄H₉ | |
| 5-CH₃SC(O)NH— | OCH₃ | H | H | H | O | CH₃ | CH₂CH₂CN | |
| 5-CH₃SC(O)NH— | OCH₃ | H | H | H | O | CH₃ | CH₂C≡CCH₃ | |

TABLE VI-continued

| R2 | QR | R3 | R4 | R5 | W | X | Y | m.p. (°C.) |
|---|---|---|---|---|---|---|---|---|
| 5-CH3SC(O)NH— | OCH3 | H | H | H | O | CH3 | OCH2CH=CH2 | |
| 5-CH3SC(O)NH— | OCH3 | H | H | H | O | CH2OCH3 | OCH3 | |
| 5-CH3SC(O)NH— | OCH3 | H | H | H | O | CH2OCH2CH3 | OCH3 | |
| 5-CH3SC(O)NH— | OCH3 | H | H | H | O | CH3 | morpholino (N-O ring) | |
| 5-CH3SC(O)NH— | OCH3 | H | H | H | O | CH3 | O(CH2)3CH3 | |
| 5-CH3SC(O)NH— | OCH3 | H | H | H | O | CH3 | OCH2CH2Br | |
| 5-CH3SC(O)NH— | OCH3 | H | H | H | O | CH3 | OCH2CCl3 | |
| 5-CH3SC(O)NH— | OCH3 | H | H | H | O | CH3 | CF3 | |
| 5-CH3SC(O)NH— | OCH3 | H | H | H | O | OCH2CH3 | OCH2CH3 | |
| 5-CH3SC(O)NH— | OCH3 | H | H | H | S | CH3 | OCH3 | |
| 5-CH3SC(O)NH— | OCH3 | H | H | H | S | OCH3 | OCH3 | |
| 5-CH3SC(O)NH— | OCH3 | H | H | CH3 | O | CH3 | OCH3 | |
| 5-CH3SC(O)NH— | OCH3 | H | CH3 | H | O | CH3 | OCH3 | |
| 5-CH3SC(O)NH— | OCH3 | 6-Cl | H | H | O | CH3 | OCH3 | |
| 5-CH3SC(O)NH— | OCH3 | 3-F | H | H | O | CH3 | OCH3 | |
| 5-CH3SC(O)NH— | OCH3 | 6-CH3 | H | H | O | CH3 | OCH3 | |
| 5-CH3OC(O)NH— | OCH3 | H | H | H | O | CH3 | CH3 | |

TABLE VI-continued

[Structure: benzoate with R2, R3 substituents on ring; C(=O)-QR group; SO2N(R4)-C(=W)-N(R5)- linker to pyrimidine ring with X and Y substituents]

| R2 | QR | R3 | R4 | R5 | W | X | Y | m.p. (°C.) |
|---|---|---|---|---|---|---|---|---|
| 5-CH3OC(O)NH— | OCH3 | H | H | H | O | CH3 | OCH3 | |
| 5-CH3OC(O)NH— | OCH3 | H | H | H | O | OCH3 | OCH3 | |
| 5-CH3OC(O)NH— | OCH3 | H | H | H | O | CH3 | OCH2CH3 | |
| 5-CH3OC(O)NH— | OCH3 | H | H | H | O | CH3 | CH2OCH3 | |
| 5-CH3OC(O)NH— | OCH3 | H | H | H | O | CH3 | OCH2CO2CH3 | |
| 5-CH3OC(O)NH— | OCH3 | H | H | H | O | CH3 | SCH(CH3)CO2CH3 | |
| 5-CH3OC(O)NH— | OCH3 | H | H | H | O | CH3 | OCH2CH2OCH3 | |
| 5-CH3OC(O)NH— | OCH3 | H | H | H | O | CH3 | SCH3 | |
| 5-CH3OC(O)NH— | OCH3 | H | H | H | O | CH3 | SCH2CH2SCH3 | |
| 5-CH3OC(O)NH— | OCH3 | H | H | H | O | CH3 | SCH2CH=CH2 | |
| 5-CH3OC(O)NH— | OCH3 | H | H | H | O | CH3 | OCH2C(O)N(CH3)2 | |
| 5-CH3OC(O)NH— | OCH3 | H | H | H | O | CH3 | n-C4H9 | |
| 5-CH3OC(O)NH— | OCH3 | H | H | H | O | CH3 | CH2CH2CN | |
| 5-CH3OC(O)NH— | OCH3 | H | H | H | O | CH3 | CH2C≡CCH3 | |
| 5-CH3OC(O)NH— | OCH3 | H | H | H | O | CH3 | OCH2CH=CH2 | |
| 5-CH3OC(O)NH— | OCH3 | H | H | H | O | CH2OCH3 | OCH3 | |
| 5-CH3OC(O)NH— | OCH3 | H | H | H | O | CH2OCH2CH3 | OCH3 | |

TABLE VI-continued

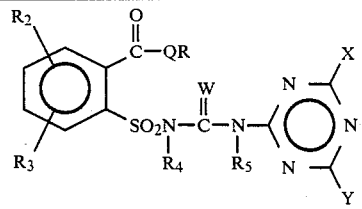

| R₂ | QR | R₃ | R₄ | R₅ | W | X | Y | m.p. (°C.) |
|---|---|---|---|---|---|---|---|---|
| 5-CH₃OC(O)NH— | OCH₃ | H | H | H | O | CH₃ | morpholino (N-O ring) | |
| 5-CH₃OC(O)NH— | OCH₃ | H | H | H | O | CH₃ | O(CH₂)₃CH₃ | |
| 5-CH₃OC(O)NH— | OCH₃ | H | H | H | O | CH₃ | OCH₂CH₂Br | |
| 5-CH₃OC(O)NH— | OCH₃ | H | H | H | O | CH₃ | OCH₂CCl₃ | |
| 5-CH₃OC(O)NH— | OCH₃ | H | H | H | O | CH₃ | CF₃ | |
| 5-CH₃OC(O)NH— | OCH₃ | H | H | H | O | OCH₂CH₃ | OCH₂CH₃ | |
| 5-CH₃OC(O)NH— | OCH₃ | H | H | H | S | CH₃ | OCH₃ | |
| 5-CH₃OC(O)NH— | OCH₃ | H | H | H | S | OCH₃ | OCH₃ | |
| 5-CH₃OC(O)NH— | OCH₃ | H | H | CH₃ | O | CH₃ | OCH₃ | |
| 5-CH₃OC(O)NH— | OCH₃ | H | CH₃ | H | O | CH₃ | OCH₃ | |
| 5-CH₃OC(O)NH— | OCH₃ | 6-Cl | H | H | O | CH₃ | OCH₃ | |
| 5-CH₃OC(O)NH— | OCH₃ | 3-F | H | H | O | CH₃ | OCH₃ | |
| 5-CH₃OC(O)NH— | OCH₃ | 6-CH₃ | H | H | O | CH₃ | OCH₃ | |
| CH₃SO₂NH— | OCH₃ | H | H | H | O | CH₃ | CH₃ | |
| CH₃SO₂NH— | OCH₃ | H | H | H | O | CH₃ | OCH₃ | |
| CH₃SO₂NH— | OCH₃ | H | H | H | O | OCH₃ | OCH₃ | |
| CH₃SO₂NH— | OCH₃ | H | H | H | O | CH₃ | OCH₂CH₃ | |
| CH₃SO₂NH— | OCH₃ | H | H | H | O | CH₃ | CH₂OCH₃ | |
| CH₃SO₂NH— | OCH₃ | H | H | H | O | CH₃ | OCH₂CO₂CH₃ | |
| CH₃SO₂NH— | OCH₃ | H | H | H | O | CH₃ | SCH(CH₃)CO₂CH₃ | |
| CH₃SO₂NH— | OCH₃ | H | H | H | O | CH₃ | OCH₂CH₂OCH₃ | |
| CH₃SO₂NH— | OCH₃ | H | H | H | O | CH₃ | SCH₃ | |
| CH₃SO₂NH— | OCH₃ | H | H | H | O | CH₃ | SCH₂CH₂SCH₃ | |
| CH₃SO₂NH— | OCH₃ | H | H | H | O | CH₃ | SCH₂CH=CH₂ | |

TABLE VI-continued

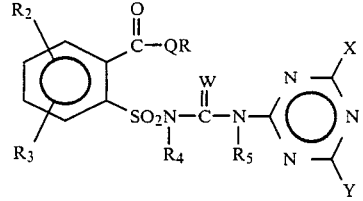

| R2 | QR | R3 | R4 | R5 | W | X | Y | m.p. (°C.) |
|---|---|---|---|---|---|---|---|---|
| CH3SO2NH— | OCH3 | H | H | H | O | CH3 | OCH2CN(CH3)2 with C=O | |
| CH3SO2NH— | OCH3 | H | H | H | O | CH3 | n-C4H9 | |
| CH3SO2NH— | OCH3 | H | H | H | O | CH3 | CH2CH2CN | |
| CH3SO2NH— | OCH3 | H | H | H | O | CH3 | CH2C≡CCH3 | |
| CH3SO2NH— | OCH3 | H | H | H | O | CH3 | OCH2CH=CH2 | |
| CH3SO2NH— | OCH3 | H | H | H | O | CH3 | morpholino (N,O ring) | |
| CH3SO2NH— | OCH3 | H | H | H | O | CH3 | O(CH2)3CH3 | |
| CH3SO2NH— | OCH3 | H | H | H | O | CH3 | OCH2CH2Br | |
| CH3SO2NH— | OCH3 | H | H | H | O | CH3 | OCH2CCl3 | |
| CH3SO2NH— | OCH3 | H | H | H | O | CH3 | CF3 | |
| CH3SO2NH— | OCH3 | H | H | H | O | OCH2CH3 | OCH2CH3 | |
| CH3SO2NH— | OCH3 | H | H | H | S | CH3 | OCH3 | |
| CH3SO2NH— | OCH3 | H | H | H | S | OCH3 | OCH3 | |
| CH3SO2NH— | OCH3 | H | H | CH3 | O | CH3 | OCH3 | |
| CH3SO2NH— | OCH3 | H | CH3 | H | O | CH3 | OCH3 | |
| CH3SO2NH— | OCH3 | 6-Cl | H | H | O | CH3 | OCH3 | |
| CH3SO2NH— | OCH3 | 3-F | H | H | O | CH3 | OCH3 | |
| CH3SO2NH— | OCH3 | 6-CH3 | H | H | O | CH3 | OCH3 | |
| CH3SO2NH— | OCH3 | H | H | H | O | CH2OCH3 | OCH3 | |
| CH3SO2NH— | OCH3 | H | H | H | O | CH2OCH2CH3 | OCH3 | |
| CF3SO2NH— | OCH3 | H | H | H | O | CH3 | CH3 | |
| CF3SO2NH— | OCH3 | H | H | H | O | CH3 | OCH3 | |
| CF3SO2NH— | OCH3 | H | H | H | O | OCH3 | OCH3 | |
| CF3SO2NH— | OCH3 | H | H | H | O | CH3 | OCH2CH3 | |
| CF3SO2NH— | OCH3 | H | H | H | O | CH3 | CH2OCH3 | |
| CF3SO2NH— | OCH3 | H | H | H | O | CH3 | OCH2CO2CH3 | |
| CF3SO2NH— | OCH3 | H | H | H | O | CH3 | SCH(CH3)CO2CH3 | |
| CF3SO2NH— | OCH3 | H | H | H | O | CH3 | OCH2CH2OCH3 | |
| CF3SO2NH— | OCH3 | H | H | H | O | CH3 | SCH3 | |
| CF3SO2NH— | OCH3 | H | H | H | O | CH3 | SCH2CH2SCH3 | |
| CF3SO2NH— | OCH3 | H | H | H | O | CH3 | SCH2CH=CH2 | |
| CF3SO2NH— | OCH3 | H | H | H | O | CH3 | OCH2CN(CH3)2 with C=O | |
| CF3SO2NH— | OCH3 | H | H | H | O | CH3 | n-C4H9 | |
| CF3SO2NH— | OCH3 | H | H | H | O | CH3 | CH2CH2CN | |
| CF3SO2NH— | OCH3 | H | H | H | O | CH3 | CH2C≡CCH3 | |
| CF3SO2NH— | OCH3 | H | H | H | O | CH3 | OCH2CH=CH2 | |
| CF3SO2NH— | OCH3 | H | H | H | O | CH3 | morpholino (N,O ring) | |
| CF3SO2NH— | OCH3 | H | H | H | O | CH3 | O(CH2)3CH3 | |
| CF3SO2NH— | OCH3 | H | H | H | O | CH3 | OCH2CH2Br | |
| CF3SO2NH— | OCH3 | H | H | H | O | CH3 | OCH2CCl3 | |
| CF3SO2NH— | OCH3 | H | H | H | O | CH3 | CF3 | |
| CF3SO2NH— | OCH3 | H | H | H | O | OCH2CH3 | OCH2CH3 | |
| CF3SO2NH— | OCH3 | H | H | H | S | CH3 | OCH3 | |
| CF3SO2NH— | OCH3 | H | H | H | S | OCH3 | OCH3 | |
| CF3SO2NH— | OCH3 | H | H | CH3 | O | CH3 | OCH3 | |
| CF3SO2NH— | OCH3 | H | CH3 | H | O | CH3 | OCH3 | |
| CF3SO2NH— | OCH3 | 6-Cl | H | H | O | CH3 | OCH3 | |

TABLE VI-continued

| R2 | QR | R3 | R4 | R5 | W | X | Y | m.p. (°C.) |
|---|---|---|---|---|---|---|---|---|
| CF$_3$SO$_2$NH— | OCH$_3$ | 3-F | H | H | O | CH$_3$ | OCH$_3$ | |
| CF$_3$SO$_2$NH— | OCH$_3$ | 6-CH$_3$ | H | H | O | CH$_3$ | OCH$_3$ | |
| CF$_3$SO$_2$NH— | OCH$_3$ | H | H | H | O | CH$_2$OCH$_3$ | OCH$_3$ | |
| CF$_3$SO$_2$NH— | OCH$_3$ | H | H | H | O | CH$_2$OCH$_2$CH$_3$ | OCH$_3$ | |

TABLE VII

| R2 | QR | R3 | W | X$_1$ | Y$_1$ |
|---|---|---|---|---|---|
| 5—NCO | OCH$_3$ | H | O | CH$_3$ | CH$_3$ |
| 5—NCO | OCH$_3$ | H | O | CH$_3$ | OCH$_3$ |
| 5—NCO | OCH$_3$ | H | O | OCH$_3$ | OCH$_3$ |
| 5-CH$_3$C(O)NH— | OCH$_3$ | H | O | CH$_3$ | CH$_3$ |
| 5-CH$_3$C(O)NH— | OCH$_3$ | H | O | CH$_3$ | OCH$_3$ |
| 5-CH$_3$C(O)NH— | OCH$_3$ | H | O | OCH$_3$ | OCH$_3$ |
| 5-CH$_3$C(O)NH— | OCH$_3$ | H | S | CH$_3$ | OCH$_3$ |
| 5-CH$_3$C(O)NH— | OCH$_3$ | 6-Cl | O | CH$_3$ | OCH$_3$ |
| 5-CH$_3$NHC(O)NH— | OCH$_3$ | H | O | CH$_3$ | CH$_3$ |
| 5-CH$_3$NHC(O)NH— | OCH$_3$ | H | O | CH$_3$ | OCH$_3$ |
| 5-CH$_3$NHC(O)NH— | OCH$_3$ | H | O | OCH$_3$ | OCH$_3$ |
| 5-CH$_3$NHC(O)NH— | OCH$_3$ | H | S | CH$_3$ | OCH$_3$ |
| 5-CH$_3$NHC(O)NH— | OCH$_3$ | 6-Cl | O | CH$_3$ | OCH$_3$ |
| 5-CH$_3$SC(O)NH— | OCH$_3$ | H | O | CH$_3$ | CH$_3$ |
| 5-CH$_3$SC(O)NH— | OCH$_3$ | H | O | CH$_3$ | OCH$_3$ |
| 5-CH$_3$SC(O)NH— | OCH$_3$ | H | O | OCH$_3$ | OCH$_3$ |
| 5-CH$_3$SC(O)NH— | OCH$_3$ | H | S | CH$_3$ | OCH$_3$ |
| 5-CH$_3$SC(O)NH— | OCH$_3$ | 6-Cl | O | CH$_3$ | OCH$_3$ |
| 5-CH$_3$OC(O)NH— | OCH$_3$ | H | O | CH$_3$ | CH$_3$ |
| 5-CH$_3$OC(O)NH— | OCH$_3$ | H | O | CH$_3$ | OCH$_3$ |
| 5-CH$_3$OC(O)NH— | OCH$_3$ | H | O | OCH$_3$ | OCH$_3$ |
| 5-CH$_3$OC(O)NH— | OCH$_3$ | H | S | CH$_3$ | OCH$_3$ |
| 5-CH$_3$OC(O)NH— | OCH$_3$ | 6-Cl | O | CH$_3$ | OCH$_3$ |
| 5-CH$_3$SO$_2$NH— | OCH$_3$ | H | O | CH$_3$ | CH$_3$ |
| 5-CH$_3$SO$_2$NH— | OCH$_3$ | H | O | CH$_3$ | OCH$_3$ |
| 5-CF$_3$SO$_2$NH— | OCH$_3$ | H | O | OCH$_3$ | OCH$_3$ |
| 5-CF$_3$SO$_2$NH— | OCH$_3$ | H | S | CH$_3$ | OCH$_3$ |
| 5-CH$_3$SO$_2$NH— | OCH$_3$ | 6-Cl | O | CH$_3$ | OCH$_3$ |

TABLE VIII

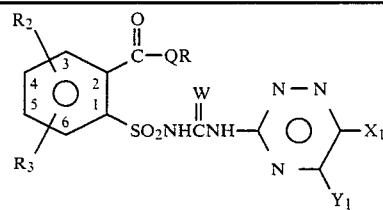

| R2 | QR | R3 | W | X1 | Y1 |
|---|---|---|---|---|---|
| 5—NCO | OCH3 | H | O | CH3 | CH3 |
| 5—NCO | OCH3 | H | O | CH3 | OCH3 |
| 5—NCO | OCH3 | H | O | OCH3 | OCH3 |
| 5-CH3C(O)NH— | OCH3 | H | O | CH3 | CH3 |
| 5-CH3C(O)NH— | OCH3 | H | O | CH3 | OCH3 |
| 5-CH3C(O)NH— | OCH3 | H | O | OCH3 | OCH3 |
| 5-CH3C(O)NH— | OCH3 | H | S | CH3 | OCH3 |
| 5-CH3C(O)NH— | OCH3 | 6-Cl | O | CH3 | OCH3 |
| 5-CH3NHC(O)NH— | OCH3 | H | O | CH3 | CH3 |
| 5-CH3NHC(O)NH— | OCH3 | H | O | CH3 | OCH3 |
| 5-CH3NHC(O)NH— | OCH3 | H | O | OCH3 | OCH3 |
| 5-CH3NHC(O)NH— | OCH3 | H | S | CH3 | OCH3 |
| 5-CH3NHC(O)NH— | OCH3 | 6-Cl | O | CH3 | OCH3 |

TABLE VIII-continued

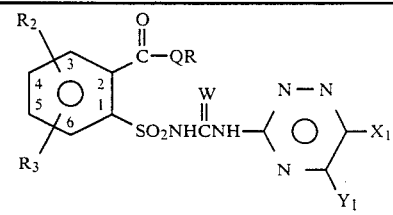

| R2 | QR | R3 | W | X1 | Y1 |
|---|---|---|---|---|---|
| 5-CH3SC(O)NH— | OCH3 | H | O | CH3 | CH3 |
| 5-CH3SC(O)NH— | OCH3 | H | O | CH3 | OCH3 |
| 5-CH3SC(O)NH— | OCH3 | H | O | OCH3 | OCH3 |
| 5-CH3SC(O)NH— | OCH3 | H | S | CH3 | OCH3 |
| 5-CH3SC(O)NH— | OCH3 | 6-Cl | O | CH3 | OCH3 |
| 5-CH3OC(O)NH— | OCH3 | H | O | CH3 | CH3 |
| 5-CH3OC(O)NH— | OCH3 | H | O | CH3 | OCH3 |
| 5-CH3OC(O)NH— | OCH3 | H | O | OCH3 | OCH3 |
| 5-CH3OC(O)NH— | OCH3 | H | S | CH3 | OCH3 |
| 5-CH3OC(O)NH— | OCH3 | 6-Cl | O | CH3 | OCH3 |
| 5-CH3SO2NH— | OCH3 | H | O | CH3 | CH3 |
| 5-CH3SO2NH— | OCH3 | H | O | CH3 | OCH3 |
| 5-CF3SO2NH— | OCH3 | H | O | OCH3 | OCH3 |
| 5-CF3SO2NH— | OCH3 | H | S | CH3 | OCH3 |
| 5-CH3SO2NH— | OCH3 | 6-Cl | O | CH3 | OCH3 |

TABLE IX

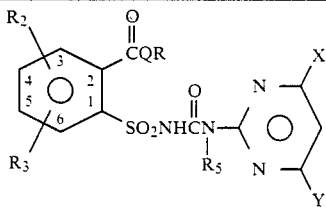

| QR | R2 | R3 | W | R5 | X | Y |
|---|---|---|---|---|---|---|
| OCH3 | H | H | O | H | CH2OCH3 | OCH3 |
| OCH3 | H | H | O | H | CH2OCH2CH3 | CH3 |
| OCH3 | 5-Cl | H | O | H | CH2OCH3 | OCH3 |
| OCH3 | 5-NO2 | H | O | H | CH2OCH3 | OCH3 |
| OCH3 | 5-OCH3 | H | O | H | CH2OCH3 | OCH3 |
| OCH3 | 5-NH2 | H | O | H | CH2OCH3 | OCH3 |
| OCH3 | 5-CH3 | H | O | H | CH2OCH3 | OCH3 |
| OCH3 | 5-CN | H | O | H | CH2OCH3 | OCH3 |
| OCH3 | 5-Br | H | O | H | CH2OCH3 | OCH3 |

TABLE IX-continued

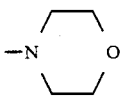

| QR | R2 | R3 | W | R5 | X | Y |
|---|---|---|---|---|---|---|
| OCH3 | 5-CF3 | H | O | H | CH2OCH3 | OCH3 |
| OCH3 | 5-Cl | Cl | O | H | CH2OCH3 | OCH3 |
| OCH3 | H | H | S | H | CH2OCH3 | OCH3 |
| O—i-C3H7 | H | H | O | H | CH2OCH3 | OCH3 |
| OCH2CH3 | H | H | O | H | CH2OCH3 | OCH3 |
| OCH2CF3 | H | H | O | H | CH2OCH3 | OCH3 |
| OCHCH2CH3<br>\|<br>CH3 | H | H | O | H | CH2OCH3 | OCH3 |
| OCH2CH2Cl | H | H | O | H | CH2OCH3 | OCH3 |
|  | H | H | O | H | CH2OCH3 | OCH3 |
| OC12H25 | H | H | O | H | CH2OCH3 | OCH3 |
| OCH2CH=CH2 | H | H | O | H | CH2OCH3 | OCH3 |
| OCH2CH—CCl2 | H | H | O | H | CH2OCH3 | OCH3 |
| OCH2CH2OCH3 | H | H | O | H | CH2OCH3 | OCH3 |
| OCH2—⌬ | H | H | O | H | CH2OCH3 | OCH3 |
| OCH2CH2SCH3 | H | H | O | H | CH2OCH3 | OCH3 |
| OCH2C≡CCH2Cl | H | H | O | H | CH2OCH3 | OCH3 |
| OCH2CN | H | H | O | H | CH2OCH3 | OCH3 |
| OCH3 | H | H | O | H | CH2OCH3 | CH2OCH3 |
| OCH3 | H | H | O | H | CH2OCH3 | SCH3 |
| OCH3 | H | H | O | H | CH2OCH3 | OCH2CH2OCH3 |
| OCH3 | H | H | O | H | CH2OCH3 | OCH2CO2CH2CH3 |
| OCH3 | H | H | O | H | CH2OCH3 | SCH2CO2CH3 |
| OCH3 | H | H | O | H | CH2OCH3 | OCH2CF3 |
| OCH3 | H | H | O | H | CH2OCH3 | OCH2CONHCH3 |
| OCH3 | H | H | O | H | CH2OCH3 | Cl |
| OCH3 | H | H | O | H | CH2OCH3 | n-C4H9 |
| OCH3 | H | H | O | H | CH2OCH3 | CH2CH2CN |
| OCH3 | H | H | O | H | CH2OCH3 | —N⌬O |
| OCH3 | H | H | O | H | CH2OCH3 | OCH2CH=CH2 |
| OCH3 | H | H | O | H | CH2OCH3 | CO2CH3 |
| OCH3 | H | H | O | CH3 | CH2OCH3 | OCH3 |
| NHCH3 | H | H | O | H | CH2OCH3 | CH3 |
| NHCH3 | H | H | O | H | CH2OCH3 | OCH3 |
| N(CH3)2 | H | H | O | H | CH2OCH3 | OCH3 |
| ⌬N | H | H | O | H | CH2OCH3 | OCH3 |
| N(CH3)CH2CH3 | H | H | O | H | CH2OCH3 | OCH3 |
| NHCH2—⌬ | H | H | O | H | CH2OCH3 | OCH3 |

TABLE IX-continued

| QR | R₂ | R₃ | W | R₅ | X | Y |
|---|---|---|---|---|---|---|
| NHCH(CH₃)₂ | H | H | O | H | CH₂OCH₃ | OCH₃ |
| N(CH₃)OCH₃ | H | H | O | H | CH₂OCH₃ | OCH₃ |
| NH—△ | H | H | O | H | CH₂OCH₃ | OCH₃ |
| N(morpholino) | H | H | O | H | CH₂OCH₃ | OCH₃ |
| NHCH₂CH=CH₂ | H | H | O | H | CH₂OCH₃ | OCH₃ |
| NHCH₂C≡CH | H | H | O | H | CH₂OCH₃ | OCH₃ |

TABLE X

| QR | R₂ | R₃ | W | R₅ | X | Y |
|---|---|---|---|---|---|---|
| OCH₃ | H | H | O | H | CH₂OCH₃ | OCH₃ |
| OCH₃ | H | H | O | H | CH₂OCH₂CH₃ | CH₃ |
| OCH₃ | 5-Cl | H | O | H | CH₂OCH₃ | OCH₃ |
| OCH₃ | 5-NO₂ | H | O | H | CH₂OCH₃ | OCH₃ |
| OCH₃ | 5-OCH₃ | H | O | H | CH₂OCH₃ | OCH₃ |
| OCH₃ | 5-NH₂ | H | O | H | CH₂OCH₃ | OCH₃ |
| OCH₃ | 5-CH₃ | H | O | H | CH₂OCH₃ | OCH₃ |
| OCH₃ | 5-CN | H | O | H | CH₂OCH₃ | OCH₃ |
| OCH₃ | 5-Br | H | O | H | CH₂OCH₃ | OCH₃ |
| OCH₃ | 5-CF₃ | H | O | H | CH₂OCH₃ | OCH₃ |
| OCH₃ | 5-Cl | Cl | O | H | CH₂OCH₃ | OCH₃ |
| OCH₃ | H | H | S | H | CH₂OCH₃ | OCH₃ |
| O—i-C₃H₇ | H | H | O | H | CH₂OCH₃ | OCH₃ |
| OCH₂CH₃ | H | H | O | H | CH₂OCH₃ | OCH₃ |
| OCH₂CF₃ | H | H | O | H | CH₂OCH₃ | OCH₃ |
| OCHCH₂CH₃ \| CH₃ | H | H | O | H | CH₂OCH₃ | OCH₃ |
| OCH₂CH₂Cl | H | H | O | H | CH₂OCH₃ | OCH₃ |
| O—(tetrahydrothiopyranyl) | H | H | O | H | CH₂OCH₃ | OCH₃ |
| OC₁₂H₂₅ | H | H | O | H | CH₂OCH₃ | OCH₃ |
| OCH₂CH=CH₂ | H | H | O | H | CH₂OCH₃ | OCH₃ |
| OCH₂CH—CCl₂ | H | H | O | H | CH₂OCH₃ | OCH₃ |
| OCH₂CH₂OCH₃ | H | H | O | H | CH₂OCH₃ | OCH₃ |
| OCH₂—C₆H₅ | H | H | O | H | CH₂OCH₃ | OCH₃ |

TABLE X-continued $$\text{structure with } R_2, R_3 \text{ on benzene ring, } CQR, SO_2NHCN(R_5)C(W)\text{-triazine with } X, Y$$

| QR | $R_2$ | $R_3$ | W | $R_5$ | X | Y |
|---|---|---|---|---|---|---|
| $OCH_2CH_2SCH_3$ | H | H | O | H | $CH_2OCH_3$ | $OCH_3$ |
| $OCH_2C\equiv CCH_2Cl$ | H | H | O | H | $CH_2OCH_3$ | $OCH_3$ |
| $OCH_2CN$ | H | H | O | H | $CH_2OCH_3$ | $OCH_3$ |
| $OCH_3$ | H | H | O | H | $CH_2OCH_3$ | $CH_2OCH_3$ |
| $OCH_3$ | H | H | O | H | $CH_2OCH_3$ | $SCH_3$ |
| $OCH_3$ | H | H | O | H | $CH_2OCH_3$ | $OCH_2CH_2OCH_3$ |
| $OCH_3$ | H | H | O | H | $CH_2OCH_3$ | $OCH_2CO_2CH_2CH_3$ |
| $OCH_3$ | H | H | O | H | $CH_2OCH_3$ | $SCH_2CO_2CH_3$ |
| $OCH_3$ | H | H | O | H | $CH_2OCH_3$ | $OCH_2CF_3$ |
| $OCH_3$ | H | H | O | H | $CH_2OCH_3$ | $OCH_2CONHCH_3$ |
| $OCH_3$ | H | H | O | H | $CH_2OCH_3$ | Cl |
| $OCH_3$ | H | H | O | H | $CH_2OCH_3$ | $n\text{-}C_4H_9$ |
| $OCH_3$ | H | H | O | H | $CH_2OCH_3$ | $CH_2CH_2CN$ |
| $OCH_3$ | H | H | O | H | $CH_2OCH_3$ | $-N(\text{morpholino})$ |
| $OCH_3$ | H | H | O | H | $CH_2OCH_3$ | $OCH_2CH=CH_2$ |
| $OCH_3$ | H | H | O | H | $CH_2OCH_3$ | $CO_2CH_3$ |
| $OCH_3$ | H | H | O | $CH_3$ | $CH_2OCH_3$ | $OCH_3$ |
| $NHCH_3$ | H | H | O | H | $CH_2OCH_3$ | $CH_3$ |
| $NHCH_3$ | H | H | O | H | $CH_2OCH_3$ | $OCH_3$ |
| $N(CH_3)_2$ | H | H | O | H | $CH_2OCH_3$ | $OCH_3$ |
| N-pyrrolidinyl | H | H | O | H | $CH_2OCH_3$ | $OCH_3$ |
| $N(CH_3)CH_2CH_3$ | H | H | O | H | $CH_2OCH_3$ | $OCH_3$ |
| $NHCH_2\text{-phenyl}$ | H | H | O | H | $CH_2OCH_3$ | $OCH_3$ |
| $NHCH(CH_3)_2$ | H | H | O | H | $CH_2OCH_3$ | $OCH_3$ |
| $N(CH_3)OCH_3$ | H | H | O | H | $CH_2OCH_3$ | $OCH_3$ |
| $NH\text{-cyclopropyl}$ | H | H | O | H | $CH_2OCH_3$ | $OCH_3$ |
| N-morpholino | H | H | O | H | $CH_2OCH_3$ | $OCH_3$ |
| $NHCH_2CH=CH_2$ | H | H | O | H | $CH_2OCH_3$ | $OCH_3$ |
| $NHCH_2C\equiv CH$ | H | H | O | H | $CH_2OCH_3$ | $OCH_3$ |

FORMULATIONS

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High-strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE XI

| | Active* Ingredient | Diluent(s) | Surfactant(s) |
|---|---|---|---|
| Wettable Powders | 20–90 | 0–74 | 1–10 |

TABLE XI-continued

| | Active* Ingredient | Diluent(s) | Surfactant(s) |
|---|---|---|---|
| Oil Suspensions, Emulsions, Solutions (including Eulsifiable Concentrates | 3-50 | 40-95 | 0-15 |
| Aqueous Suspensions | 10-50 | 40-84 | 1-20 |
| Dusts | 1-25 | 70-99 | 0-5 |
| Granules and Pellets | 0.1-95 | 5-99.9 | 0-15 |
| High-Strength Compositions | 90-99 | 0-10 | 0-2 |

*Active ingredient plus at least one of a surfactant or a diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, New Jersey. The more absorptive diluents are preferred for wettable powders and the denser ones for dusts. Typical liquid diluents and solvents are described in Marsden, "Solvents Guide", 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, New Jersey, as well as Sisely and Wood, "Encyclopedia of Surface Active Agents", Chemical Publishing Co., Inc., New York 1964, list surfactants and recommended uses. All formulations can contain minor amounts of additives to reduce foam, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, December 4, 1967, pp. 147ff and "Perry's Chemical Engineer's Handbook", 5th Ed., McGraw-Hill, New York, 1973, pp. 8-57ff.

For further information regarding the art of formulation, see for example:

H. M. Loux, U.S. Pat. No. 3,235,361, February 15, 1966, Col. 6, line 16 through Col. 7, line 19 and Examples 10 through 41.

R. W. Luckenbaugh, U.S. Pat. No. 3,309,192, March 14, 1967, Col. 5, line 43 through Col. 1, line 62 and Examples 8, 12, 15, 39, 41, 52, 53, 58, 132, 138-140, 162-164, 166, 167 and 169-182.

H. Gysin and E. Knusli, U.S. Pat. No. 2,891,855, June 23, 1959, Col. 5, line 66 through Col. 5, line 17 and Examples 1-4.

G. C. Klingman, "Weed Control as a Science", John Wiley & Sons, Inc., New York, 1961, pp. 81-96.

J. D. Fryer and S. A. Evans, "Weed Control Handbook", 5th Ed., Blackwell Scientific Publications, Oxford, 1968, pp. 101-103.

In the following examples, all parts are by weight unless otherwise indicated.

EXAMPLE 8

Wettable Powder

| | |
|---|---|
| Methyl 2-[[(4,6-dimethylpyrimidin-2-yl)aminocarbonyl]-aminosulfonyl]-5-[(methylamino)carbonylamino]-benzoate | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns and then reblended.

EXAMPLE 9

Wettable Powder

| | |
|---|---|
| Methyl 2-[[(4-methoxy-6-methylpyrimidin-2-yl)aminocarbonyl]aminosulfonyl]-5-[(methylamino)carbonylamino]benzoate | 50% |
| sodium alkylnaphthalenesulfonate | 2% |
| low viscosty methyl cellulose | 2% |
| diatomaceous earth | 46% |

The ingredients are blended, coarsely hammer-milled and then air-milled to produce particles of active essentially all below 10 microns in diameter. The product is reblended before packaging.

EXAMPLE 10

Granule

| | |
|---|---|
| wettable powder of Example 9 | 5% |
| attapulgite granules | 95% |
| (U.S.S. 20-40 mesh; 0.84-0.42 mm) | |

A slurry of wettable powder containing $\approx 25\%$ solids is sprayed on the surface of attapulgite granules in a double-cone blender. The granules are dried and packaged.

EXAMPLE 11

Extruded Pellet

| | |
|---|---|
| Methyl 2-[[(4-methoxy-6-methyl-1,3,5-triazin-2-yl)-aminocarbonyl]aminosulfonyl]-5-[(methylamino)-carbonylamino]benzoate | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 12

Oil Suspension

| | |
|---|---|
| Methyl 5-[(1,1-dimethylethylamino)carbonylamino]-2-[[(4-methoxy-6-methylpyrimidin-2-yl)aminocarbonyl]-aminosulfonyl]benzoate | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 13

Wettable Powder

| | |
|---|---|
| 1-[2-[[(4,6-dimethoxypyrimidin-2-yl)aminocarbonyl]aminosulfonyl]benzoyl]-2,3-dihydro-1H—indole | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and shifted through a U.S.S. No. 50 sieve (0.3 mm opening) and packaged.

EXAMPLE 14

Low Strength Granule

| | |
|---|---|
| Methyl 5-[(1,1-dimethylethylamino)carbonylamino]-2-[[(4-methoxy-6-methyl-1,3,5-triazin-2-yl)aminocarbonyl]aminosulfonyl]benzoate | 1% |
| N,N—dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 15

Aqueous Suspension

| | |
|---|---|
| Methyl 5-[(1,1-dimethylethylamino)carbonylamino]-2-[[(4,6-dimethoxypyrimidin-2-yl)aminocarbonyl]-aminosulfonyl]benzoate | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| Water | 56.7% |

The ingredients are blended and ground together in a sand mill to produce particles essentially all under 5 microns in size.

EXAMPLE 16

Solution

| | |
|---|---|
| Methyl 4-[(2-chloroethylamino)carbonylamino]-2-[[(4,6-dimethoxypyrimidin-2-yl)aminosulfonyl]-benzoate, sodium salt | 5% |
| water | 95% |

The salt is added directly to the water with stirring to produce the solution, which may then be packaged for use.

EXAMPLE 17

Low Strength Granule

| | |
|---|---|
| Methyl 4-(acetylamino)-2-[[(4,6-dimethoxy-pyrimidin-2-yl)aminocarbonyl]aminosulfonyl]-benzoate | 0.1% |
| attapulgite granules (U.S.S. 20–40 mesh) | 99.9% |

The active ingredient is dissolved in a solvent and the solution is sprayed upon dedusted granules in a double cone blender. After spraying of the solution has been completed, the material is warmed to evaporate the solvent. The material is allowed to cool and then packaged.

EXAMPLE 18

Granule

| | |
|---|---|
| Methyl 5-[(1-methylethylamino)carbonylamino]-2-[[(4-methoxy-6-methyl-1,3,5-triazin-2-yl)aminosulfonyl]-benzoate | 80% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water constant is reduced to the desired level, generally less than 1%. The material is then discharged, screened to the desired size range, generally 14–100 mesh (1410–149 microns), and packaged for use.

EXAMPLE 19

High Strength Concentrate

| | |
|---|---|
| Methyl 2-[[(4,6-dimethoxypyrimidin-2-yl)aminocarbonyl]-aminosulfonyl]-4-[(methylamino)carbonylamino]-benzoate | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 20

Wettable Powder

| | |
|---|---|
| Methyl 2-[[(4-methoxy-6-methyl-1,3,5-triazin-2-yl)-aminocarbonyl]aminosulfonyl]-5-[(methylamino)-carbonylamino]benzoate | 90% |
| dioctyl sodium sulfosuccinate | 0.1% |
| synthetic fine silica | 9.9% |

The ingredients are blended and ground in a hammermill to produce particles essentially all below 100 microns. The material is sifted through a U.S.S. No. 50 screen and then packaged.

EXAMPLE 21

Wettable Powder

| | |
|---|---|
| 1-[2-[[(4,6-dimethoxypyrimidin-2-yl)aminocarbonyl]-aminosulfonyl]benzoyl]-2,3-dihydro-1H—indole | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 22

Oil Suspension

| | |
|---|---|
| Methyl 2-[[(4,6-dimethoxypyrimidin-2-yl)aminocarbonyl]-aminosulfonyl]-4-[(methylamino)carbonylamino]-benzoate | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 23

Dust

| | |
|---|---|
| Methyl 5-[(1,1-dimethylethylamino)carbonylamino]-2-[[(4-methoxy-6-methylpyrimidin-2-yl)aminocarbonyl]-aminosulfonyl]benzoate | 10% |
| attapulgite | 10% |
| Pyrophyllite | 80% |

The active ingredient is blended with attapulgite and then passed through a hammer mill to produce particles substantially all below 200 microns. The ground concentrate is then blended with powdered pyrophyllite until homogeneous.

UTILITY

The compounds of the present invention are highly active herbicides. They have utility for broad-spectrum pre and/or post-emergence weed control in areas where complete control of all vegetation is desired, such as around fuel storage tanks, ammunition depots, industrial storage areas, oil well sites, drive-in theaters, around billboards, highway and railroad structures. By properly selecting rate and time of application, compounds of this invention may be used also to modify plant growth beneficially.

The precise amount of the compound of Formula I to be used in any given situation will vary according to the particular end result desired, the amount of foliage present, the weeds to be controlled, the soil type, the formulation and mode of application, weather conditions, etc. Since so many variables play a role, it is not possible to state a rate of application suitable for all situations. Broadly speaking, the compounds of this invention are used at levels of about 0.01 to 20 kg/ha with a preferred range of 0.1 to 10 kg/ha. In general, the higher rates of application from within this range will be selected for adverse conditions or where extended persistence in soil is desired.

The compounds of Formula I may be combined with other herbicides and are particularly useful in combination with 3-(3,4-dichlorophenyl)-1,1-dimethyl urea; the triazines such as 2-chloro-4-(ethylamino)-6-(isopropylamino)-s-triazine: the uracils such as 5-bromo-3-sec-butyl-6-methyluracil; N-(phosponomethyl)glycine; 3-cyclohexyl-1-methyl-6-dimethylamino-s-triazine-2,4(1H,3H)-dione; N,N-dimethyl-2,2-diphenylacetamide; 2,4-dichlorophenoxyacetic acid (and closely related compounds); 4-chloro-2-butynyl-3-chlorophenylcarbamate; diisopropylthiolcarbamic acid; ester with 2,3-dichloroallyl alcohol; diisopropylthiolcarbamic acid, S-(2,3,3-trichloroallyl)ester; ethyl-N-benzoyl-N-(3,4-dichlorophenyl)-2-aminopropionate; 1,2-dimethyl-3,5-diphenylpyrazolium methylsulfate; methyl 2-[4-(2,4-dichlorophenoxy)-phenoxy]propanoate; 4-amino-6-tert-butyl-3-(methylthio)-1,2,4-triazin-5(4H)-one; 3-(3,4-dichlorophenyl)-1-methoxy-1-methylurea; 3-isopropyl-1H-2,1,3-benzothiodiazin-(4H)-3H-one-2,2-dioxide; α,α,α-trifluoro-2,6-dinitro-N,N-dipropyl-p-toluidine; 1,1'-dimethyl-4,4'-bipyridinium ion; monosodium methanearsonate; 2-chloro-2',6'-diethyl(methoxymethyl)acetanilide; and 1,1-dimethyl-3-(α,α,α-trifluoro-m-tolyl)-urea.

The activity of these compounds was discovered in greenhouse tests. The tests are described and the data resulting from them are shown below.

0=no effect
& or 10=maximum effect
C=chlorosis or necrosis
D=defoliation
E=emergence inhibition
G=growth retardation
H=formative effects
U=unusual pigmentation
6Y=adscised buds or flowers

TEST PROCEDURE A

Seeds of crabgrass (Digitaria spp.), barnyardgrass (Echinochloa crusgalli), wild oats (Avena fatua), cassia (Cassia tora), morningglory (Ipomoea spp.), cocklebur (Xanthium spp.), sorghum, corn, soybean, rice, wheat and nutsedge tubers (Cyperus rotundus) were planted in a growth medium and treated preemergence with a nonphytotoxic solvent solution of the compounds of Table A. At the same time, cotton having five leaves (including cotyledonary ones), bush beans with the third trifoliate leaf expanding, crabgrass with two leaves, barnyardgrass with two leaves, wild oats with two leaves, cassia with three leaves (including cotyledonary ones), morningglory with four leaves (including the cotyledonary ones), cocklebur with four leaves (including the cotyledonary ones), sorghum with four leaves, corn with four leaves, soybean with two cotyledonary leaves, rice with three leaves, wheat with one leaf, and nutsedge with three-five leaves were sprayed with a nonphytotoxic solvent solution of the compounds of Table A. Other containers of the above mentioned weeds and crops were treated pre- or post-emergence with the same nonphytotoxic solvent so as to provide a solvent control. A set of untreated control plants was also included for comparison. Preemergence and postemergence treated plants and controls were maintained in a greenhouse for sixteen days, then all treated plants were compared with their respective controls and rated visually for response to treatment. The data in Table A shows that the compounds of this invention are very effective as herbicides.

TABLE A
| Structure | kg/ha | BUSH-BEAN | COT-TON | MORN-ING-GLORY | COCK-LEBUR | CAS-SIA | NUT-SEDGE | CRAB-GRASS | BARN-YARD-GRASS | WILD OATS | WHEAT | CORN | SOY-BEAN | RICE | SOR-GHUM |
|---|---|---|---|---|---|---|---|---|---|---|---|---|---|---|---|
| | | | | | | | | POST-EMERGENCE | | | | | | | |
|  | 0.05 | 5C,6Y, 9G | 4C,4H, 8G | 4C,9H | 4G,5X | 1C | 1C,9G | 4C,8G | 5C,9H | 6C,9G | 4C,9G | 3C,8H | 1C,5H | 9C, | 4C,9G |
| 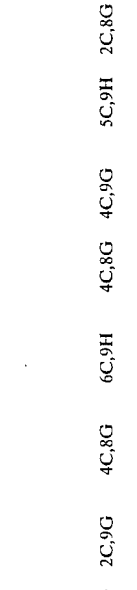 | 0.05 | 6C,6Y, 9G | 6C,9G | 5C,9H | 4C,9G | 4C,8G | 2C,9G | 4C,8G | 6C,9H | 4C,8G | 4C,9G | 5C,9H | 2C,8G | 9C | 4C,9G |
|  | 0.05 | 1C | 1C | 2C,6H | 0 | 0 | 0 | 0 | 1C,3H | 0 | 2G | 1C,4G | 0 | 1C,5G | 2C,8H |
| 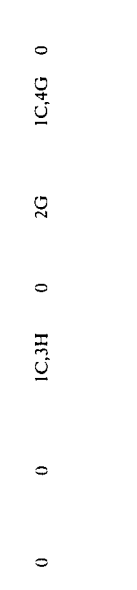 | 0.05 | 6Y,4C, 4G | 7C,4G | 8C,6G | 4C,5G | 7C,6G | 0 | 2G | 6C,5G | 0 | 2C | 0 | 6C,5G | 3G | 6C,7G |

TABLE A-continued
| Structure | Rate | | | | | | | | | | | | | |
|---|---|---|---|---|---|---|---|---|---|---|---|---|---|---|
| 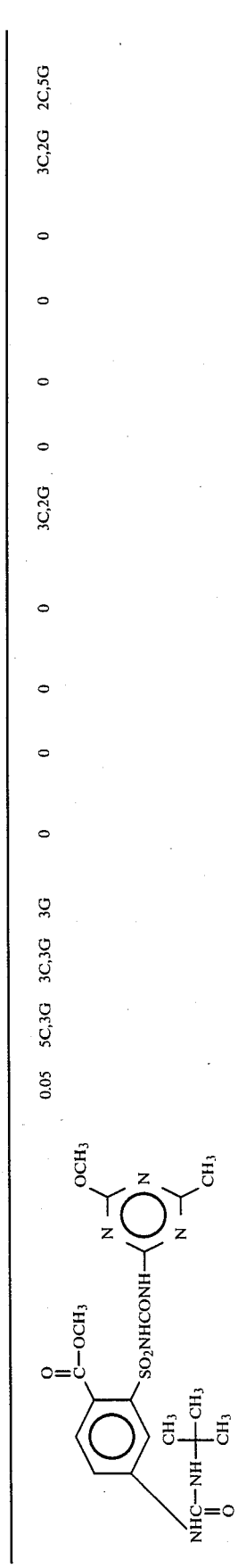 | 0.05 | 5C,3G | 3C,3G | 3G | 0 | 0 | 0 | 3C,2G | 0 | 0 | 0 | 0 | 3C,2G | 2C,5G |
| 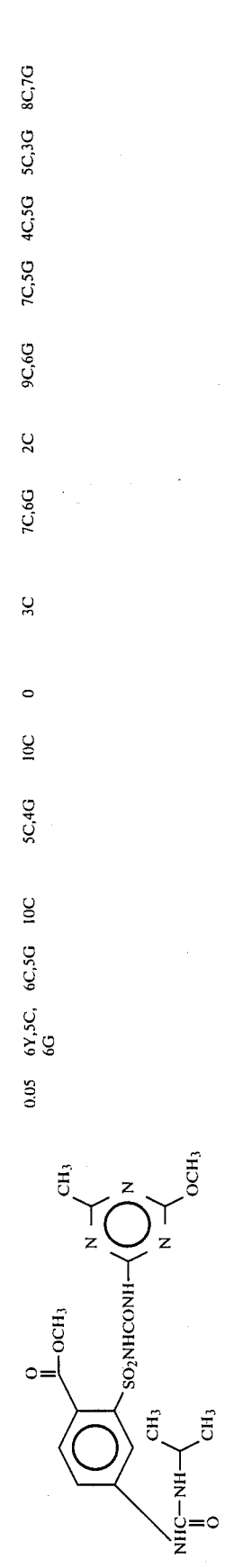 | 0.05 | 6Y,5C,6G | 6C,5G | 10C | 5C,4G | 0 | 3C | 7C,6G | 2C | 9C,6G | 7C,5G | 4C,5G | 5C,3G | 8C,7G |
| 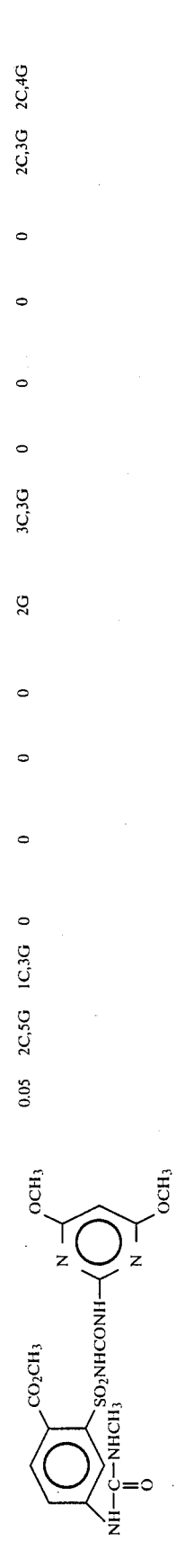 | 0.05 | 2C,5G | 1C,3G | 0 | 0 | 0 | 2G | 3C,3G | 0 | 0 | 0 | 0 | 2C,3G | 2C,4G |
| 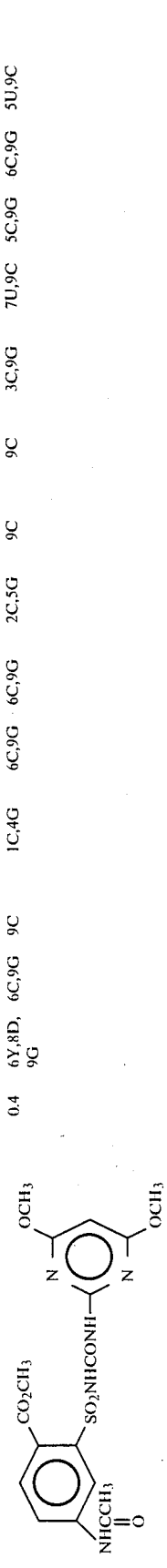 | 0.4 | 6Y,8D,9G | 6C,9G | 9C | 1C,4G | 6C,9G | 2C,5G | 9C | 9C | 3C,9G | 7U,9C | 5C,9G | 6C,9G | 5U,9C |

TABLE A-continued

| Structure | kg/ha | Morning Glory | Cock-lebur | Cas-sia | Nut-sedge | Crab-grass | Barn-yard Grass | Wild Oats | Wheat | Corn | Soybean | Rice | Sorghum |
|---|---|---|---|---|---|---|---|---|---|---|---|---|---|
| (indoline-N-CO-phenyl-SO₂NHCONH-pyrimidine(OCH₃)₂) | 0.05 | 6C,6Y,9G | 6C,9G | 10C | 1C | 1C,7G | 1C,7G | 1C,4G | 3G,9H | 1C | 1C | 1C,5H | 5C,9G | 2C,9H |
| (CH₃-O-CH₂ triazine w/ SCH₃, NHCNHSO₂-phenyl-CO₂CH₃) | 0.4 | 9C | 3C,3H, 9G | 10C | 9C | 2C,7G | 6C,9H | 2C | 1C | 10C | 3C,9G | 4C,9G | 4C,9G |

PRE-EMERGENCE

| Structure | kg/ha | Morning Glory | Cock-lebur | Cas-sia | Nut-sedge | Crab-grass | Barn-yard Grass | Wild Oats | Wheat | Corn | Soybean | Rice | Sorghum |
|---|---|---|---|---|---|---|---|---|---|---|---|---|---|
| (pyrimidine(CH₃)₂ with SO₂NHCONH, phenyl-COOCH₃, NHC(=O)NHCH₃) | 0.05 | 9G | 8H | 5G | 3G | 0 | 3C,6H | 4C,9H | 9G | 3C,9H | 2C,4H | 4C,8G | 6C,9H |
| (pyrimidine(OCH₃)(CH₃) with SO₂NHCONH, phenyl-COOCH₃, NHC(=O)NHCH₃) | 0.05 | 9G | 9H | 5C,8G | 10E | 3C,5G | 5C,9H | 5C,8G | 9H | 10H | 9H | 10E | 5C,9H |

TABLE A-continued

| Structure | | | | | | | | | | | | |
|---|---|---|---|---|---|---|---|---|---|---|---|---|
| (pyrimidine with CH₃, CH₃; benzene with C(=O)OCH₃, SO₂NHCONH, NHC-NHCH₃, C=O) | 0.05 | 5H 4C,5G | 3C,2G | 6C,7G | 0 | 2C,3G | 7C,6G | 4C,5G | 2C,3G | 4C,5G 5C,3G | 7C,6G 5C,7G | 0 |
| (pyrimidine with OCH₃, CH₃; benzene with C(=O)OCH₃, SO₂NHCONH, C(CH₃)₂-NH-C=O) | 0.05 | 0 | 3C,5G | 6C,7G | 0 | 2C,3G | 7C,6G | 4C,5G | 2C,3G | 4C,5G | 0 | 0 |
| (pyrimidine with OCH₃, CH₃; benzene with C(=O)OCH₃, SO₂NHCONH, C(CH₃)₂-NH-C=O) | 0.05 | 0 | 0 | 0 | 0 | 0 | 0 | 0 | 0 | 0 | 0 | 0 |
| (pyrimidine with CH₃, OCH₃; benzene with C(=O)OCH₃, SO₂NHCONH, CH(CH₃)-CH(CH₃)-NH-C=O) | 0.05 | 4C,5G | 3C,5G | 5C,6G | 0 | 2G | 2C,3G | 4G | 2C,5G | 2C,3G 3C,3G | 4C,5G 6C,7G | 0 |

TABLE A-continued

| Structure | | | | | | | | | | | | | | |
|---|---|---|---|---|---|---|---|---|---|---|---|---|---|---|
| [structure 1: benzene with CO2CH3, SO2NHCONH-pyrimidine(OCH3)2, NH-C(=O)-NHCH3] | 0.05 | 0 | 9G | 0 | 10E | 2C,8G | 3C,9G | 1C,8G | 1C,9G | 1U,9G | 9H | 10E | 9H | 0 |
| [structure 2: benzene with CO2CH3, SO2NHCONH-pyrimidine(OCH3)2, NHCOCH3] | 0.4 | 0 | — | 0 | 9G | 2C | 2C,6H | 7G | 5G | 1C,6G | 1C,2G | 9H | 1C,8G | 0 |
| [structure 3: phthalimide-benzene with SO2NHCONH-pyrimidine(OCH3)2] | 0.05 | 3C,9G | 4C,9G | 5C,9G | 8G | 2C,6G | 3C,9H | 2C,8G | 7G | 10E | 9H | 10E | 7C,9H | 0 |
| [structure 4: CH3-O-CH2-triazine(SCH3)-NH-C(=O)-NH-SO2-benzene-CO2CH3] | 0.4 | | | | | | | | | | | | | |

What is claimed is:

1. A compound selected from

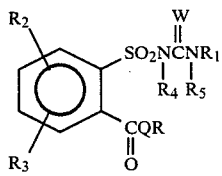

wherein
Q is O;
R is $C_1$-$C_{12}$ alkyl, $C_3$-$C_{10}$ alkenyl, $C_3$-$C_{10}$ alkynyl, $C_2$-$C_6$ alkyl substituted with one to four substituents selected from 0-3 atoms of F, Cl or Br, 0-2 methoxy groups and 0-1 cyano groups, $CH_2CN$,

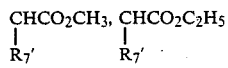

where $R_7'$ is H or $CH_3$, $C_3$-$C_6$ alkenyl substituted with 1-3 atoms of F, Cl or Br, $C_3$-$C_6$ alkynyl substituted with one of F, Cl or Br, $C_5$-$C_8$ cycloalkyl, $C_5$-$C_8$ cycloalkenyl, $C_5$-$C_6$ cycloalkyl substituted with $OCH_3$, alkyl of $C_2$-$C_4$, F, Cl or Br or one to four methyl groups, $C_4$-$C_{10}$ cycloalkylalkyl or $C_4$-$C_8$ cycloalkylalkyl with 1-2 $CH_3$;
R is also H, M, $CH_2CH_2OR_7$, $CH_2CH_2CH_2OR_7$,

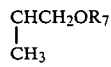

where $R_7$ is $CH_2CH_3$ or $CH(CH_3)_2$, $CH_2OR_8'$ where $R_8'$ is $CH_3$, $CH_2CH_3$, $CH(CH_3)_2$, $CH_2CH_2OCH_3$, or $CH_2CH_2OCH_2CH_3$, $(CH_2CH_2O)_{n'}R_8$,

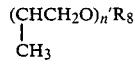

where $R_8$ is $CH_3$, $CH_2CH_3$ or $CH(CH_3)_2$ and n' is

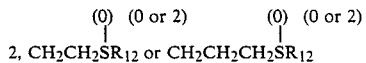

2, $CH_2CH_2SR_{12}$ or $CH_2CH_2CH_2SR_{12}$ where $R_{12}$ is $CH_3$, $CH_2CH_3$ or $CH(CH_3)_2$ and provided that R has a total number of carbon atoms ≦13;
$R_1$ is

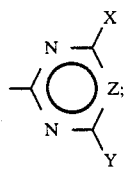

$R_2$ is NCO,

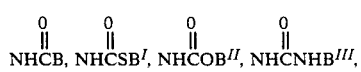

$CF_3SO_2NH$ or $CH_3SO_2NH$;

B is $C_1$-$C_4$ alkyl optionally substituted with 1-3 atoms of F, Cl, Br or a single $OCH_3$ group or $C_2$-$C_4$ alkenyl;
$B^I$ is $C_1$-$C_4$ alkyl or $C_3$-$C_4$ alkenyl;
$B^{II}$ is $C_1$-$C_4$ alkyl optionally substituted with $CH_2CH_2OCH_3$, $CH_2CH_2OCH_2CH_3$ or 1-3 atoms of F, Cl or Br, or $C_3$-$C_4$ alkenyl;
$B^{III}$ is $C_1$-$C_4$ alkyl optionally substituted with Cl or $OCH_3$ or $C_3$-$C_4$ alkenyl;
$R_3$ is H, Cl, Br, F or $CH_3$;
$R_4$ is H or $CH_3$;
$R_5$ is H, $CH_3$ or $OCH_3$;
M is an alkali metal;
W is oxygen or sulfur;
X is H, Cl, $CH_3$, $OCH_3$, $OCH_2CH_3$, $OCH_2CH_2OCH_3$, $CH_2OCH_3$ or $CH_2OCH_2CH_3$;
Y is H, F, Cl, Br, $C_1$-$C_4$ alkyl,

where L is $NH_2$, OH, $NCH_3$, $NH(C_1$-$C_4$ alkyl), $N(C_1$-$C_4$ alkyl)$_2$ or $C_1$-$C_6$ alkoxy, $OCH_3$, $C_1$-$C_4$ alkyl substituted with $OCH_3$, $OC_2H_5$, CN or 1 to 3 atoms of F, Cl or Br, $C_3$-$C_4$ alkenyl, $CH_2C\equiv CR_{13}$ where $R_{13}$ is H, $CH_3$ or $CH_2Cl$, —A—$(CH_2)_{n'}$—$A_1$—($C_1$-$C_3$ alkyl) where A is O or S and $A_1$ is O, S or $SO_2$ and n' is as previously defined, SCN, $N_3$, $NR_{16}R_{17}$ where $R_{16}$ is H or $CH_3$ and $R_{17}$ is H, $OCH_3$, $C_1$-$C_6$ alkyl, $C_1$-$C_4$ alkyl substituted with CN, $C_3$-$C_4$ alkenyl, $C_3$-$C_6$ cycloalkyl or $C_2$-$C_3$ alkyl substituted with $OCH_3$ or $OC_2H_5$, or $R_{16}$ and $R_{17}$ can be taken together to form —$CH_2CH_2CH_2CH_2$— or —$CH_2CH_2OCH_2CH_2$—, $OR_{14}$ where $R_{14}$ is $C_1$-$C_4$ alkyl substituted with cyano, $C_3$-$C_4$ alkenyl or $CH_2C\sigma$—$CR_{13}$ where $R_{13}$ is as previously defined,

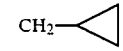

or $SR_{15}$ where $R_{15}$ is $C_1$-$C_4$ alkyl; with the provision that when Y is ≧4 carbon atoms, R is ≦4 carbon atoms; when X is Cl, then Y is Cl; and when X and Y are both H, then R is ≦4 carbon atoms; and
Z is N or CH.

2. A compound of claim 1 in which W is O, $R_3$, $R_4$ and $R_5$ are H, $R_2$ is —NCO,

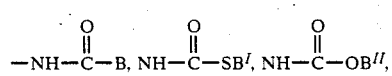

$CF_3SO_2NH$ or $CH_3SO_2NH$; and Q is O.

3. A compound of claim 1 in which W is O; $R_3$, $R_4$ and $R_5$ are H; and
QR is

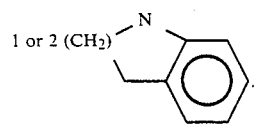

4. A compound of claim 1 in which W is O; $R_3$, $R_4$ and $R_5$ are H and QR is

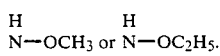

5. A compound of claim 1 in which W is O; $R_3$, $R_4$ and $R_5$ are H; and QR is

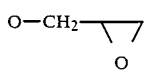

6. A compound of claim 2 in which $R_2$ is in the 5-position of the benzene ring.

7. A compound of claim 2 in which $R_1$ is

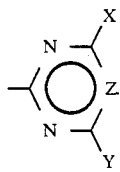

8. A compound of claim 7 in which $R_2$ is in the 5-position of the benzene ring.

9. A compound of claim 8 in which R is $C_1$–$C_4$ alkyl, $C_3$–$C_4$ alkenyl; $C_2$–$C_3$ alkyl substituted with Cl; $CH_2CH_2$—O—$CH_3$, $CH_2CH_3$);

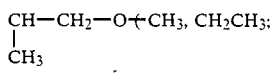

or $CH_2CH_2CH_2$—O—($CH_3$, $CH_2CH_3$).

10. A compound of claim 9 in which X is $CH_3$, $OCH_3$ or $CH_2OCH_3$.

11. A compound of claim 10 in which Y is $CH_3$, $CH_3CH_2$, $C_1$–$C_4$ alkoxy or $CH_3S$.

12. A compound of claim 11 in which Y is $CH_3$, $CH_3O$ or $CH_3S$.

13. A compound of claim 12 in which R is $CH_3$.

14. A compound of claim 12 in which B, $B^I$, $B^{II}$ are $C_1$–$C_4$ alkyl and $B^{III}$ is $C_1$–$C_4$ alkyl optionally substituted with an atom of F, Cl or Br.

15. A compound of claim 14 in which X and Y are independently $CH_3$ or $CH_3O$.

16. A compound of claim 15 in which R is $CH_3$.

17. A compound of claim 16 in which $R_2$ is

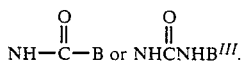

18. A compound of claim 3 in which $R_2$ is H, F, Cl, Br, $CH_3$, $CH_3O$ or $CF_3$.

19. A compound of claim 18 in which $R_1$ is

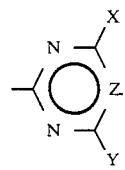

20. A compound of claim 19 in which X is $CH_3$, $CH_3O$, or $CH_2OCH_3$; and Y is $CH_3$, $CH_3O$ or $CH_3S$.

21. A compound of claim 20 in which $R_2$ is H; and X and Y are independently $CH_3$ or $CH_3O$.

22. A compound of claim 21 in which QR is

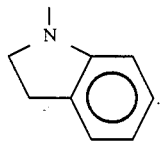

23. A compound of claim 5 in which $R_2$ is H, F, Cl, Br, $CH_3$, $CH_3O$ or $CF_3$.

24. A compound of claim 23 in which $R_1$ is

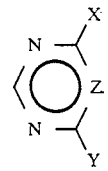

25. A compound of claim 24 in which X and Y are independently $CH_3$ or $CH_3O$.

26. A compound of claim 25 in which $R_2$ is H.

27. The compound of claim 1, methyl 2-[[(4,6-dimethylpyrimidin-2-yl)aminocarbonyl]aminosulfonyl]-5-[(methylamino)carbonylamino]benzoate.

28. The compound of claim 1, methyl 2-[[(4-methoxy-6-methylpyrimidin-2-yl)aminocarbonyl]aminosulfonyl]-5-[(methylamino)carbonylamino]benzoate.

29. The compound of claim 1, methyl 2-[[(4-methoxy-6-methyl-1,3,5-triazin-2-yl)aminocarbonyl]aminosulfonyl]-5-[(methylamino)carbonylamino]benzoate.

30. The compound of claim 1, methyl 5-[(1,1-dimethylethylamino)carbonylamino]-2-[[(4-methoxy-6-methylpyrimidin-2-yl)aminocarbonyl]aminosulfonyl]benzoate.

31. The compound of claim 1, methyl 5-[(1,1-dimethylethylamino)carbonylamino]-2-[[(4-methoxy-6-methyl-1,3,5-triazin-2-yl)aminocarbonyl]aminosulfonyl]benzoate.

32. The compound of claim 1, methyl 5-[(1,1-dimethylethylamino)carbonylamino]-2-[[(4-methoxy-6-methyl-1,3,5-triazin-2-yl)aminocarbonyl]aminosulfonyl]benzoate.

33. The compound of claim 1, methyl 5-[(1-methylethylamino)carbonylamino]-2-[[(4-methoxy-6-methyl-1,3,5-triazin-2-yl)aminosulfonyl]benzoate.

34. The compound of claim 1, methyl 2-[[(4,6-dimethoxypyrimidin-2-yl)aminocarbonyl]aminosulfonyl]-4-[(methylamino)carbonylamino]benzoate.

35. The compound of claim 1, methyl 4-(acetylamino)-2-[[(4,6-dimethoxypyrimidin-2-yl)aminocarbonyl]aminosulfonyl]benzoate.

36. The compound of claim 1, methyl 4-[(2-chloroethylamino)carbonylamino]-2-[[(4,6-dimethoxypyrimidin-2-yl)aminosulfonyl]benzoate.

37. The compound of claim 1, 1-[2-[[(4,6-dimethoxypyrimidin-2-yl)aminocarbonyl]aminosulfonyl]benzoyl]-2,3-dihydro-1H-indole.

38. The compound of claim 1, 1-[2-[[(4,6-dimethylpyrimidin-2-yl)aminocarbonyl]aminosulfonyl]benzoyl]-2,3-dihydro-1H-indole.

39. The compound of claim 1, 1-[2-[[(4-methoxy-6-methylpyrimidin-2-yl)aminocarbonyl]aminosulfonyl]benzoyl]-2,3-dihydro-1H-indole.

40. The compound of claim 1, 1-[2-[[(4,6-dimethoxy-1,3,5-triazin-2-yl)aminocarbonyl]aminosulfonyl]benzoyl]-2,3-dihydro-1H-indole.

41. The compound of claim 1, 1-[2-[[(4,6-dimethyl-1,3,5-triazin-2-yl)aminocarbonyl]aminosulfonyl]benzoyl]-2,3-dihydro-1H-indole.

42. The compound of claim 1, 1-[2-[[4-methoxy-6-methyl-1,3,5-triazin-2-yl)aminocarbonyl]aminosulfonyl]benzoyl]-2,3-dihydro-1H-indole.

43. The compound of claim 1, 2-oxiranylmethyl 2-[[(4,6-dimethylpyrimidin-2-yl)aminocarbonyl]aminosulfonyl]benzoate.

44. The compound of claim 1, 2-oxiranylmethyl 2-[[(4,6-dimethoxypyrimidin-2-yl)aminocarbonyl]aminosulfonyl]benzoate.

45. The compound of claim 1, 2-oxiranylmethyl 2-[[(4,6-dimethoxypyrimidin-2-yl)aminocarbonyl]aminosulfonyl]benzoate.

46. The compound of claim 1, 2-oxiranylmethyl 2-[[(4-methoxy-6-methylpyrimidin-2-yl)aminocarbonyl]aminosulfonyl]benzoate.

47. The compound of claim 1, 2-oxiranylmethyl 2-[[(4,6-dimethoxy-1,3,5-triazin-2-yl)aminocarbonyl]aminosulfonyl]benzoate.

48. The compound of claim 1, 2-oxiranylmethyl 2-[[(4,6-dimethyl-1,3,5-triazin-2-yl)aminocarbonyl]aminosulfonyl]benzoate.

49. The compound of claim 1, 2-oxiranylmethyl 2-[[(4-methoxy-6-methyl-1,3,5-triazin-2-yl)aminocarbonyl]aminosulfonyl]benzoate.

50. The compound of claim 1, methyl 2-[[(4-methoxymethyl-6-methylthio-1,3,5-triazin-2-yl)aminocarbonyl]aminosulfonyl]benzoate.

* * * * *